United States Patent
Stief

(10) Patent No.: US 7,510,879 B2
(45) Date of Patent: Mar. 31, 2009

(54) DETECTION PROCEDURES FOR FIBRINOGEN AND/OR FIBRINOGEN DERIVATIVES

(76) Inventor: Thomas W. Stief, Limesstrasse 15, 35415 Pohlheim (DE)

( * ) Notice: Subject to any disclaimer, the term of this patent is extended or adjusted under 35 U.S.C. 154(b) by 890 days.

(21) Appl. No.: 10/858,683

(22) Filed: Jun. 2, 2004

(65) Prior Publication Data

US 2004/0253739 A1    Dec. 16, 2004

(30) Foreign Application Priority Data

Jun. 4, 2003    (DE) .............................. 103 25 173

(51) Int. Cl.
 *G01N 33/86* (2006.01)
 *G01N 33/48* (2006.01)
(52) U.S. Cl. .............................. 436/69; 436/63; 436/88; 436/164; 436/166; 422/73; 435/13
(58) Field of Classification Search ................. 436/63, 436/69, 164, 166, 88; 422/73; 435/2, 13; 252/408.1
See application file for complete search history.

(56) References Cited

U.S. PATENT DOCUMENTS

| | | | |
|---|---|---|---|
| 4,692,406 A | 9/1987 | Becker | |
| 5,292,664 A | 3/1994 | Fickenscher | |
| 5,851,836 A * | 12/1998 | Enomoto | ..................... 436/69 |
| 6,448,024 B1 | 9/2002 | Bruegger | |
| 6,670,177 B2 * | 12/2003 | Williams | ..................... 435/325 |
| 2002/0168398 A1 * | 11/2002 | Delmotte | ..................... 424/443 |

FOREIGN PATENT DOCUMENTS

| | | |
|---|---|---|
| DE | 41 33 946 | 4/1993 |
| EP | 0 137 269 | 4/1985 |
| EP | 0 699 909 A2 | 3/1996 |
| WO | WO-92/01065 | 1/1992 |
| WO | 03/069984 * | 8/2003 |

OTHER PUBLICATIONS

Coller, B. S., et al, "Effects of Vancomycin on Platelets, Plasma Protein and Hepatitis B Surface Antigen," Thrombos. Diathes. Haemorrh. (Stuttg.), 34:pp. 83-93 (1975).
Ts-ao, Chung-Hsin, et al, "Some factors affecting fibrinogen precipitation by ristocetin: ultrastructure of precipitates," Blood 45 (5):pp. 621-629 (May 1975).
Marx, G., et al, "Albumin indirectly modulates fibrin and protofibrin ultrastructure," Biochemistry 28 (20):pp. 8242 (Oct. 3, 1989) [Abstract only].
European Patent Office Search Report for EP App. No. 04010893.8, mailed Oct. 29, 2004 (5 pages).
Faur, Y.C. et al. "Lincomycin versus vancomycin in New York City (NYC) medium for the cultural diagnosis of gonorrhoea." *The British Journal of Venereal Diseases*, Feb. 1982, 58(1), p. 66.

* cited by examiner

*Primary Examiner*—Maureen M Wallenhorst
(74) *Attorney, Agent, or Firm*—Connolly Bove Lodge & Hutz

(57) ABSTRACT

Described are determination procedures for fibrinogen and/or fibrinogen-derivatives by matrix-independent turbidimetry. In the FIFTA called procedure the fibrinogen activity is preferably determined in an undiluted sample by addition of thrombin and/or albumin, as well as polybrene if appropriate, in PBS and determination of the increase in absorbance at 405 nm. In the FIATA called procedure the fibrinogen-concentration and/or the concentration of fibrinogen-derivatives is preferably determined by addition of vancomycin and determination of the increase in turbidity at 405 nm. It is standardized by usage of plasma standards of known fibrinogen-activity and/or fibrinogen-concentration.

16 Claims, 76 Drawing Sheets

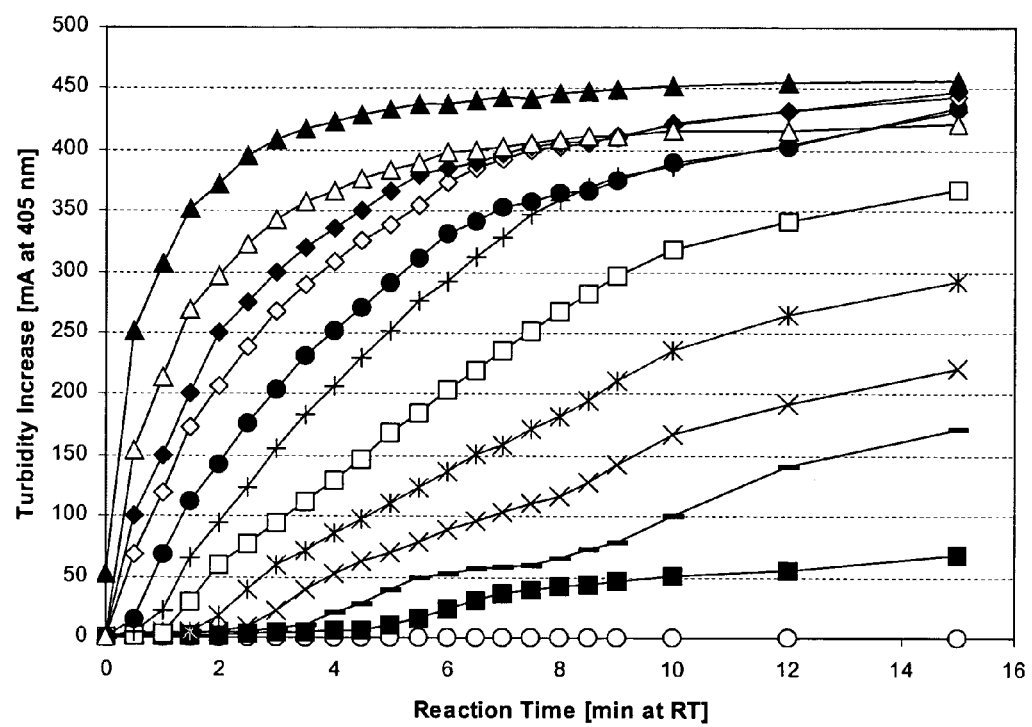
Fig. 1a: Optimization of thrombin concentration

Fig. 1b: Optimization of thrombin concentration
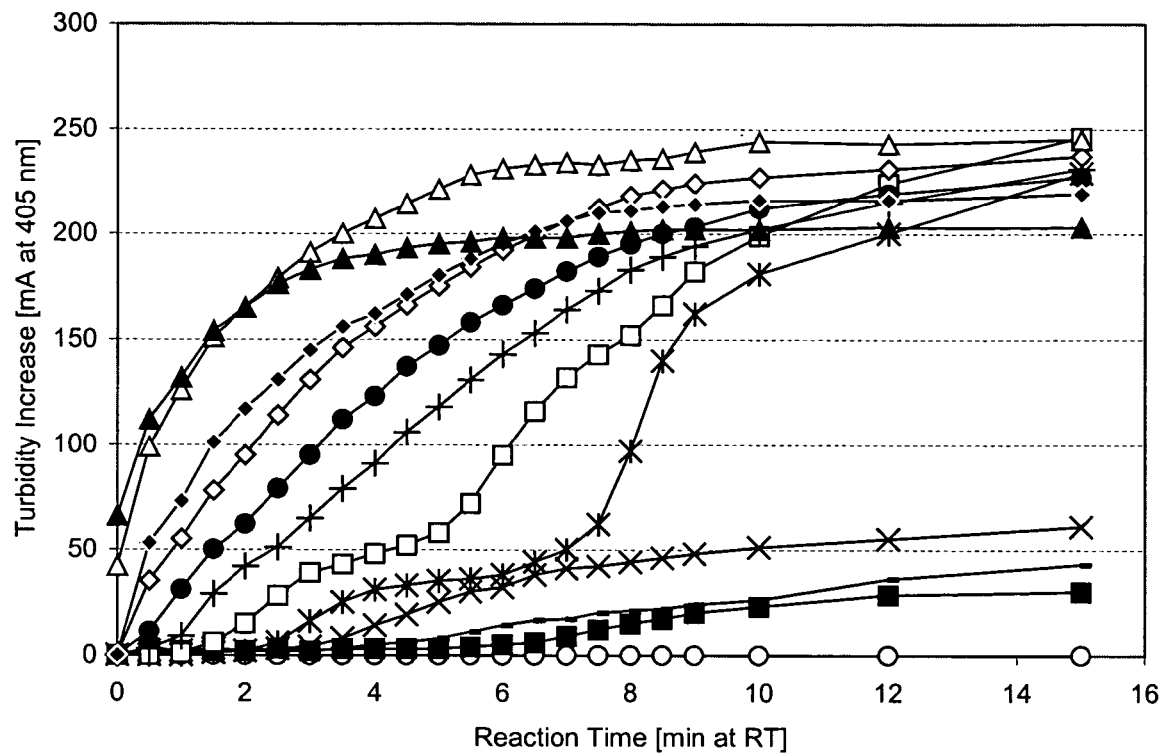
Fig. 1c: Optimization of thrombin concentration
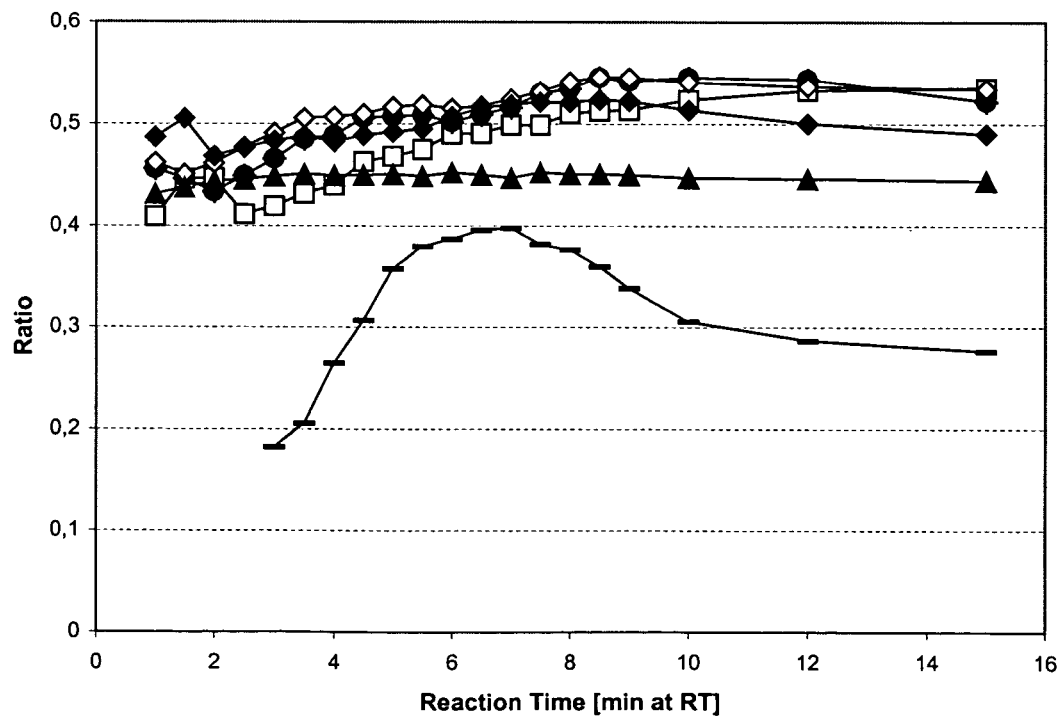

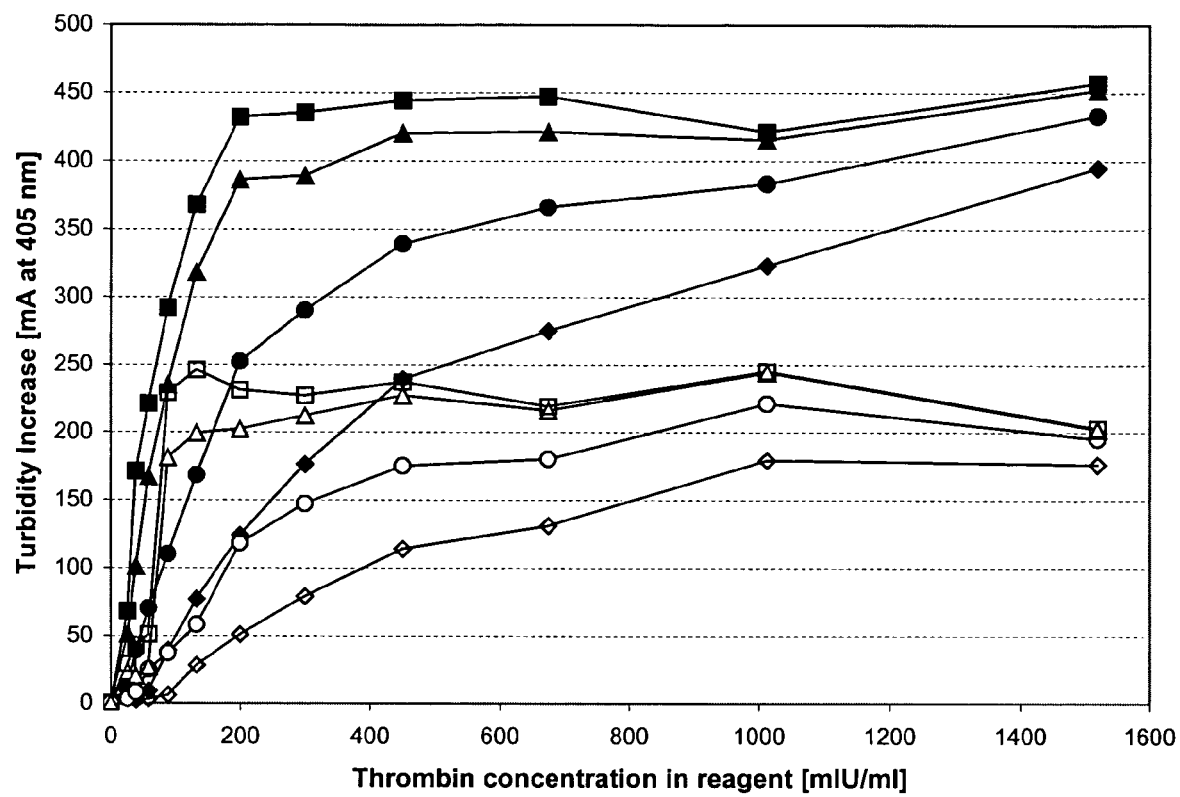
Fig. 1d: Optimization of thrombin concentration

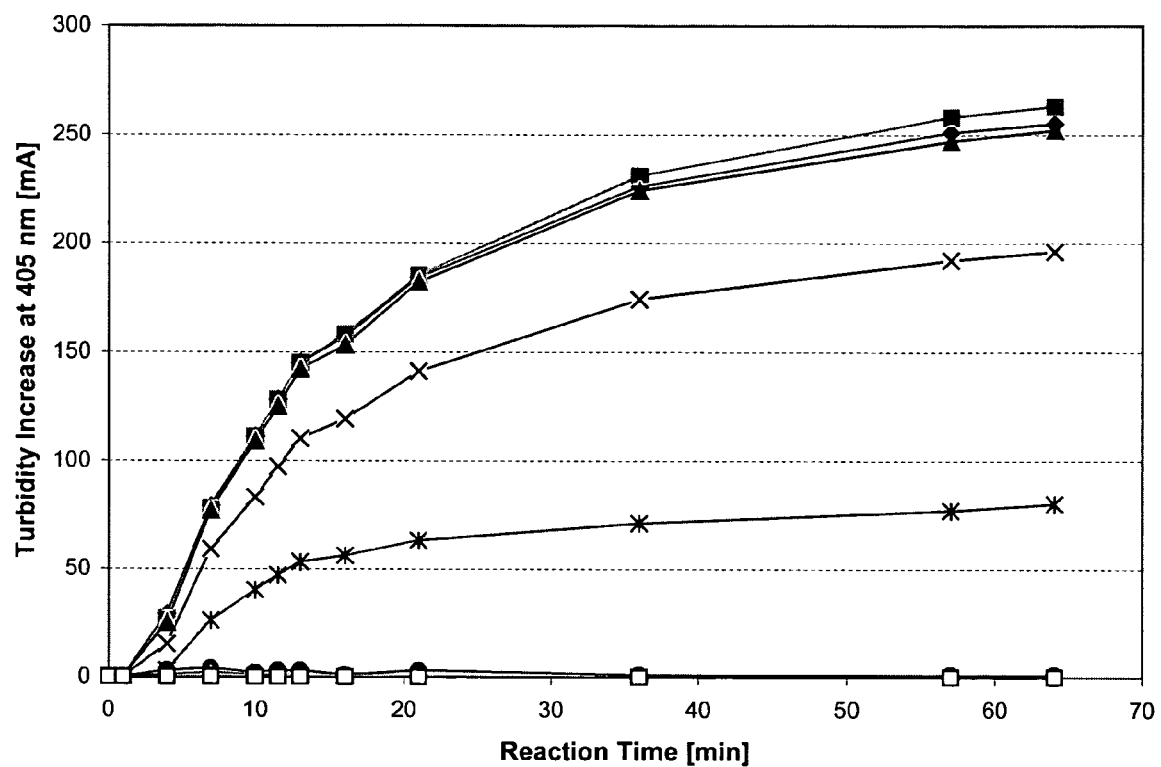
Fig. 2a: Optimization of polybrene concentration

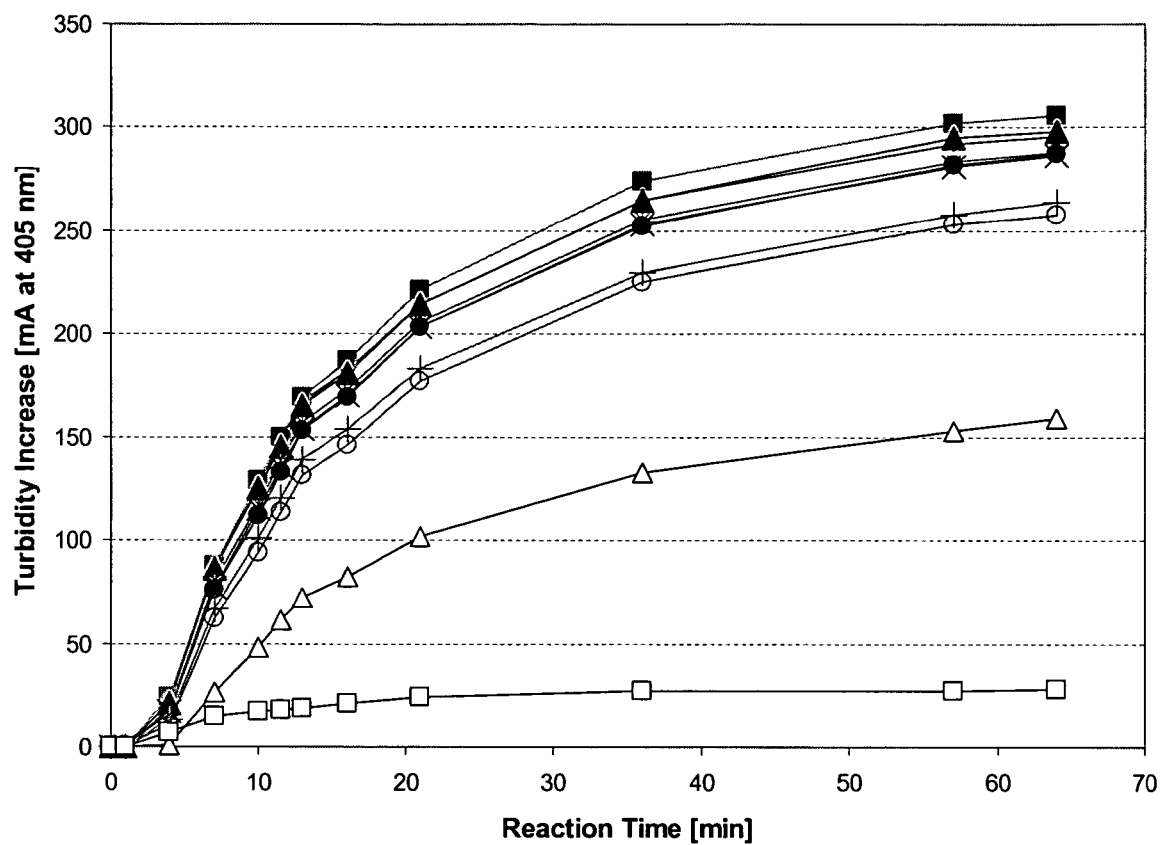
Fig. 2b: Optimization of polybrene concentration

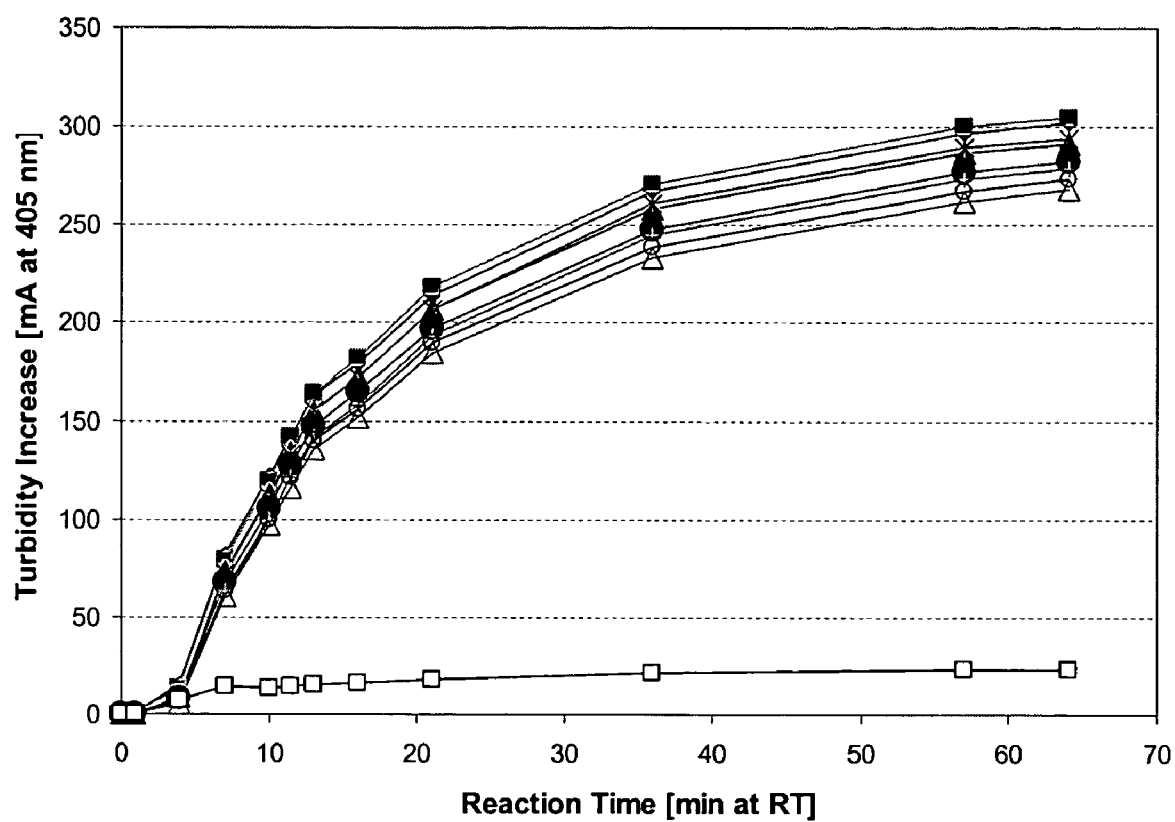
Fig. 2c: Optimization of polybrene concentration

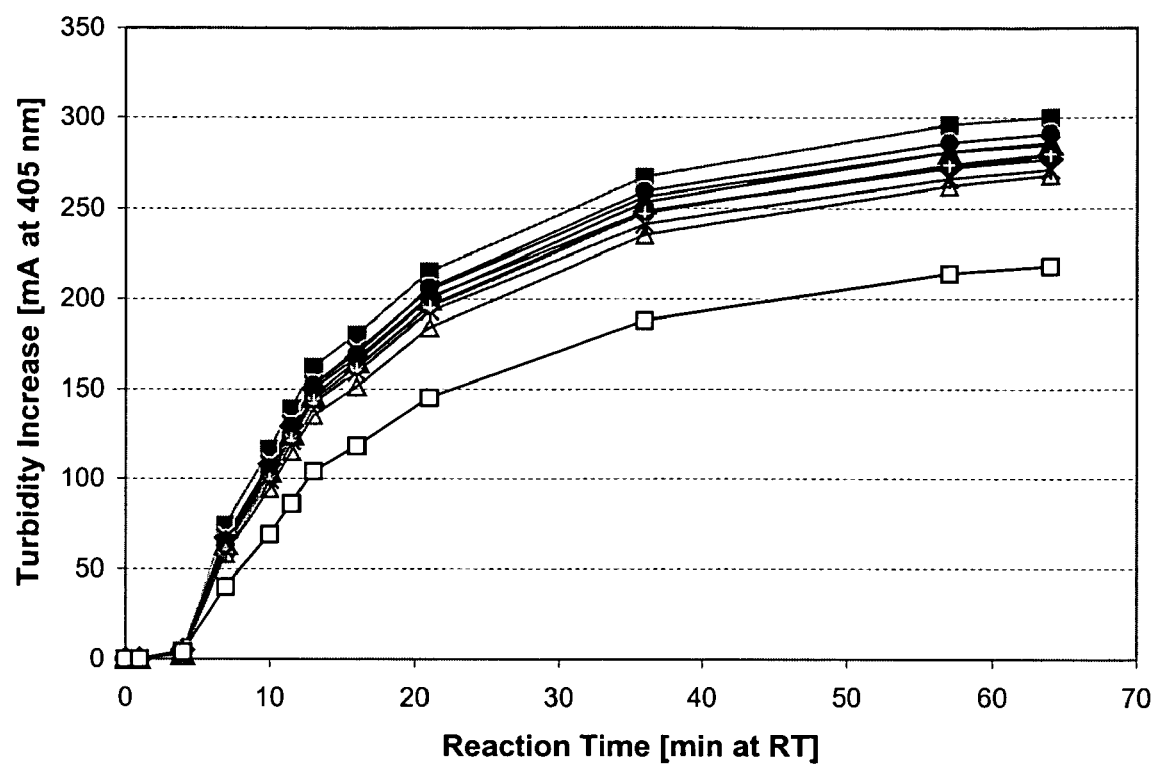
Fig. 2d: Optimization of polybrene concentration

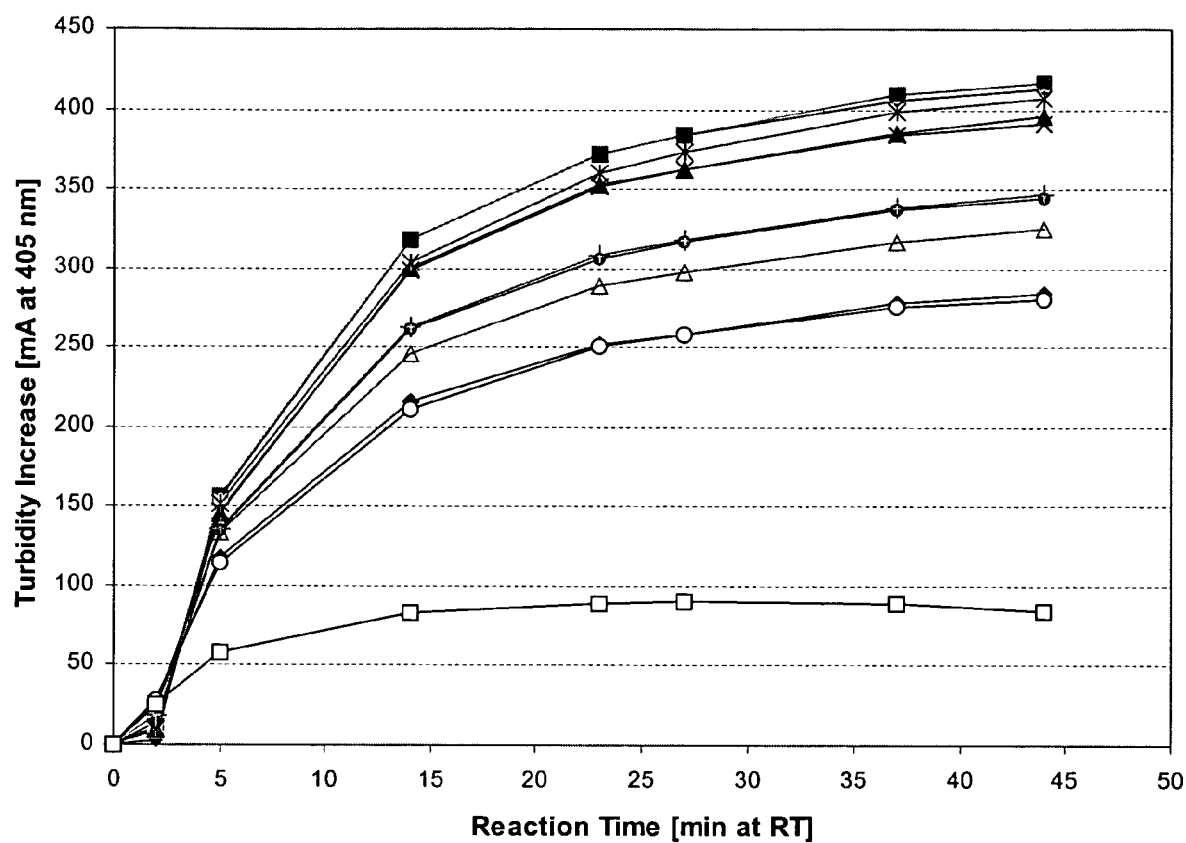
Fig. 2e: Optimization of polybrene concentration

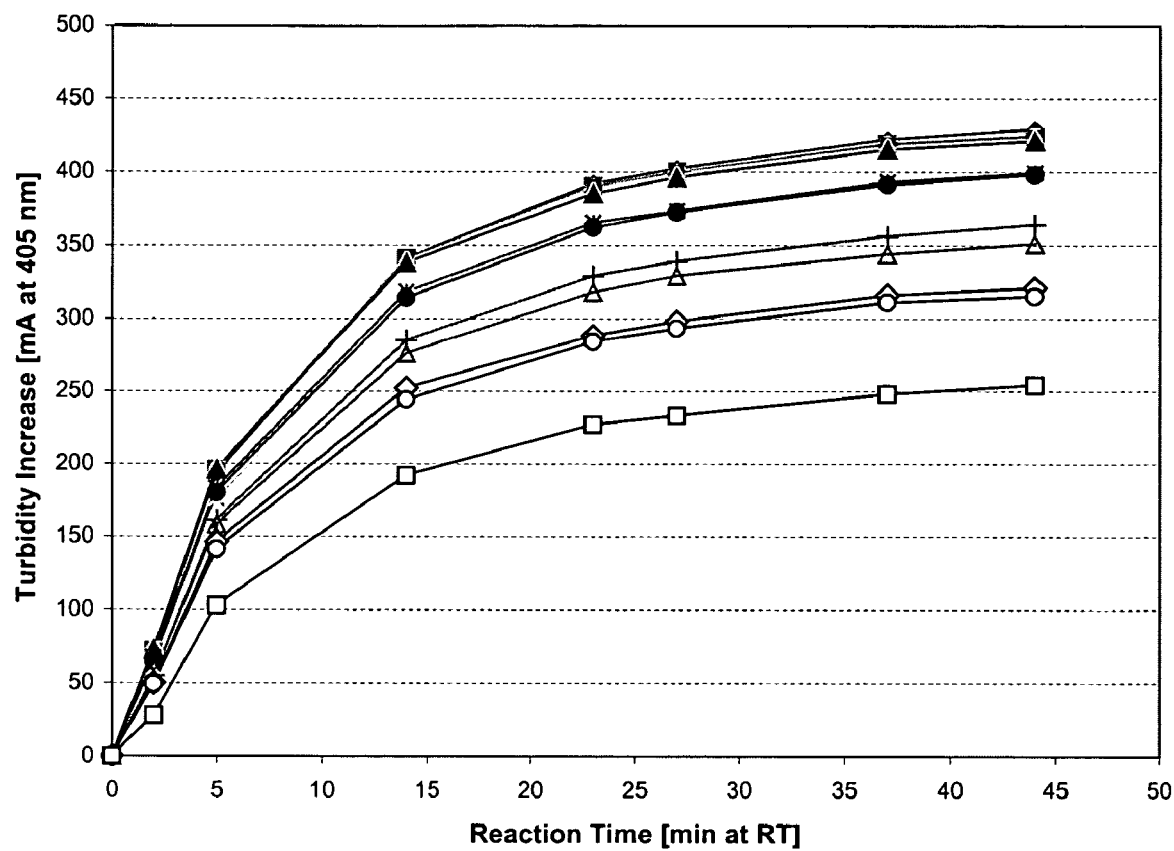
Fig. 2f: Optimization of polybrene concentration

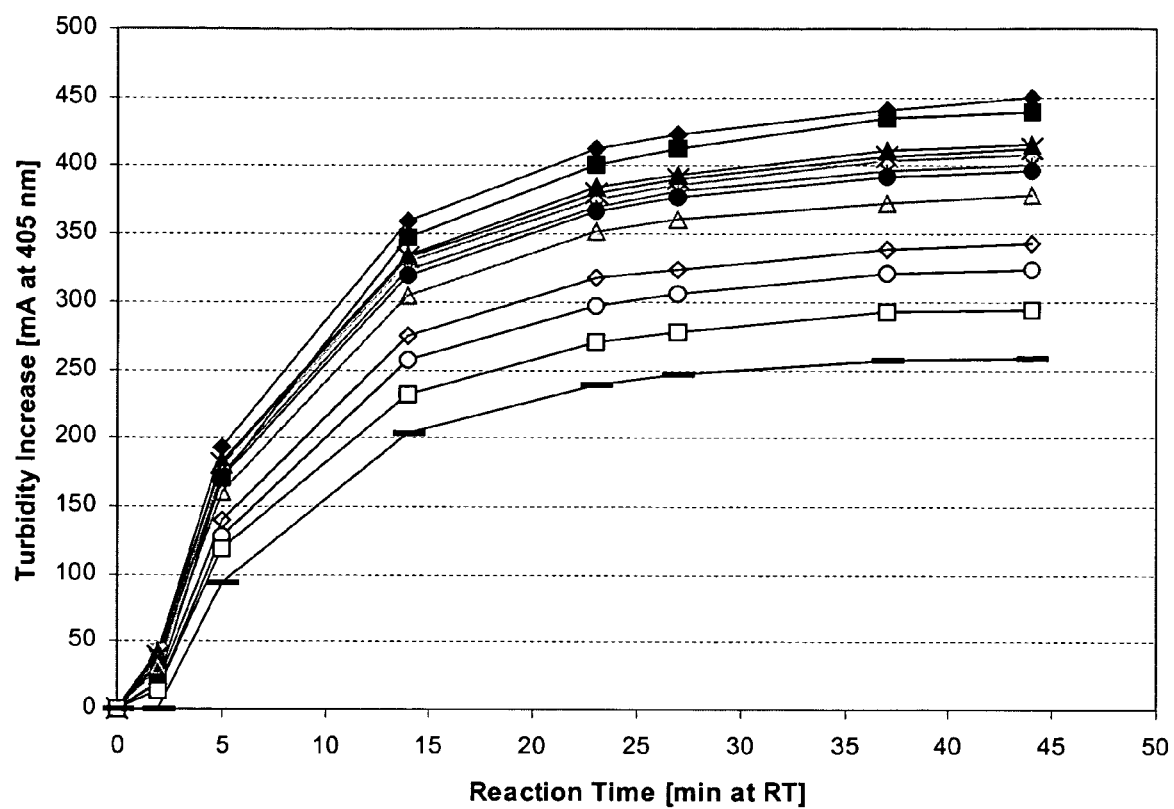
Fig. 2g: Optimization of polybrene concentration

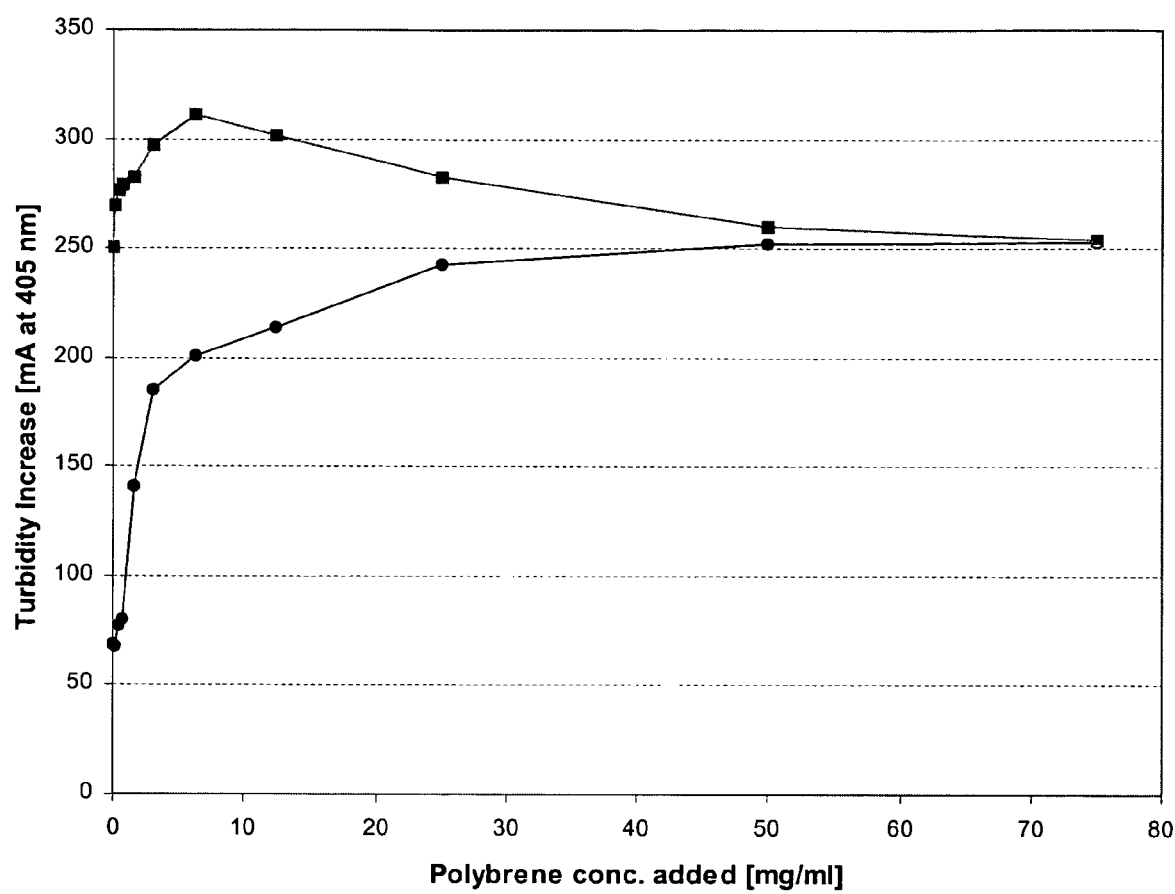
Fig. 3: Heparin neutralization by polybrene

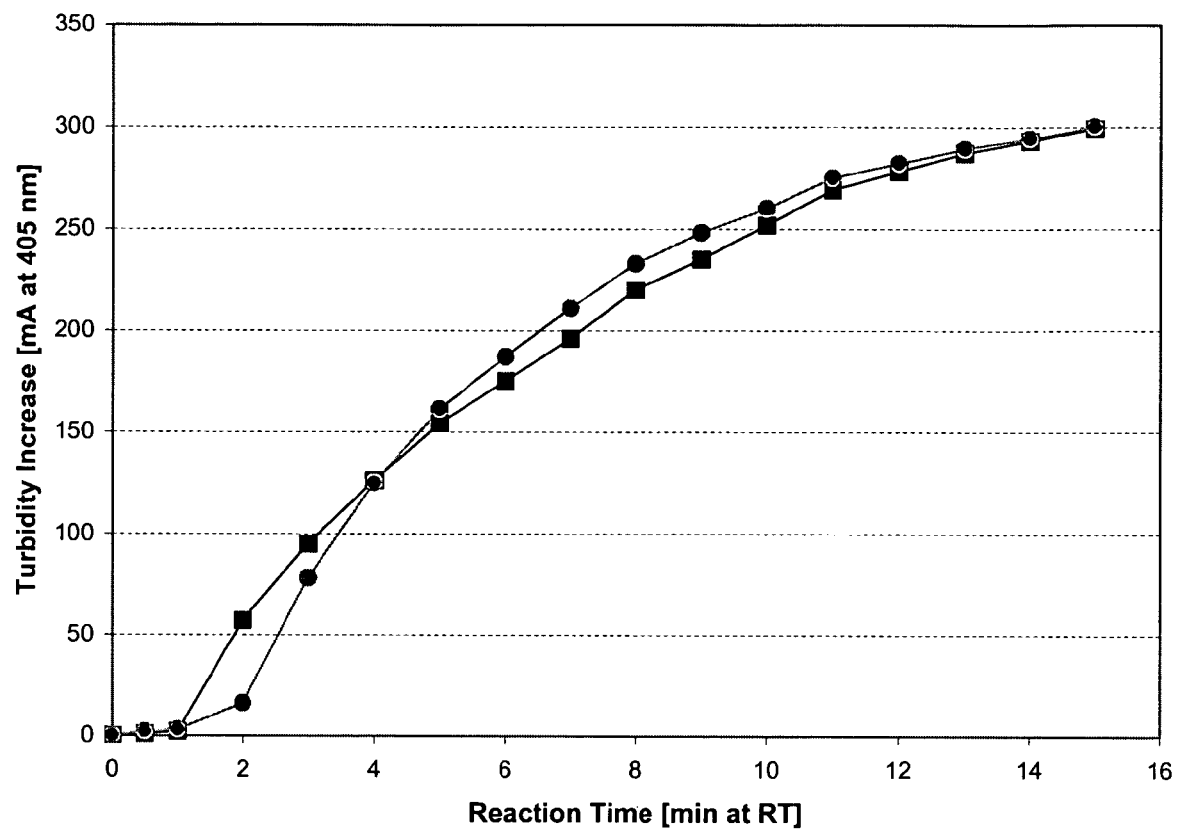
Fig. 4: FIFTA for PB neutralized heparinized plasma

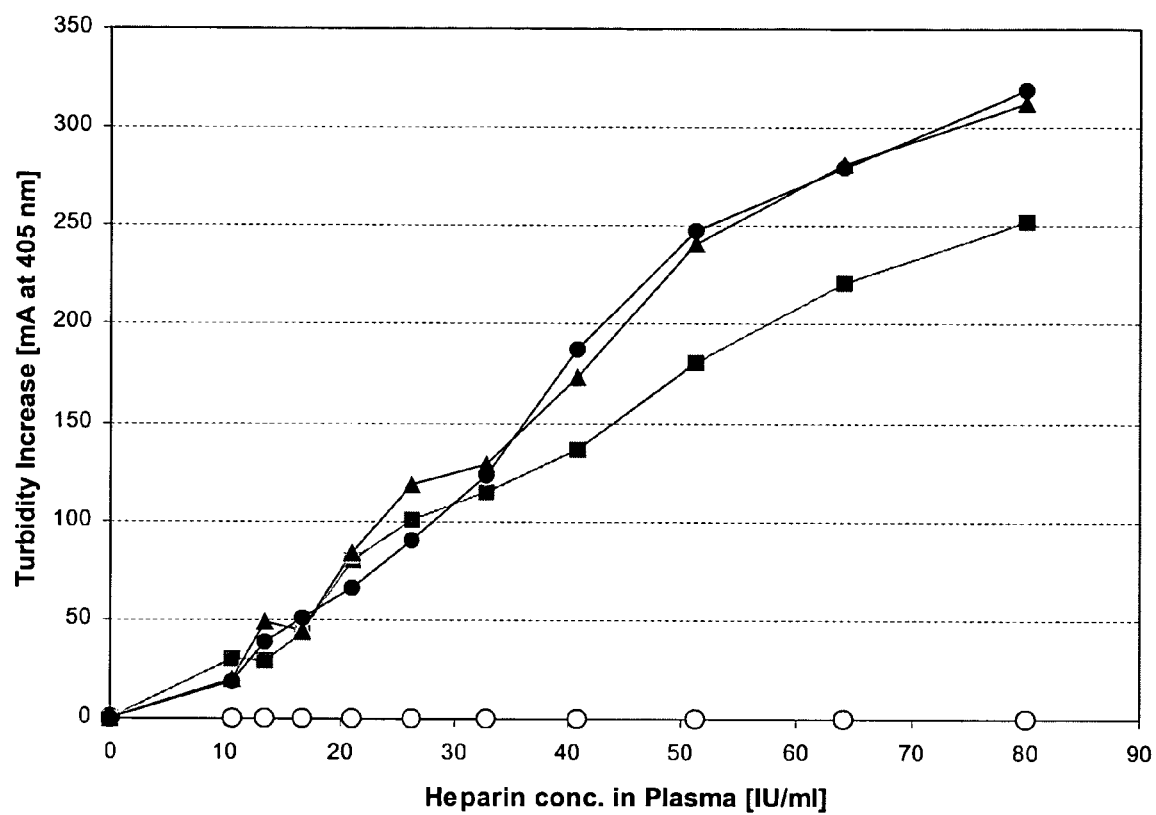
Fig. 5: Turbidity increase by PB/heparin complexes

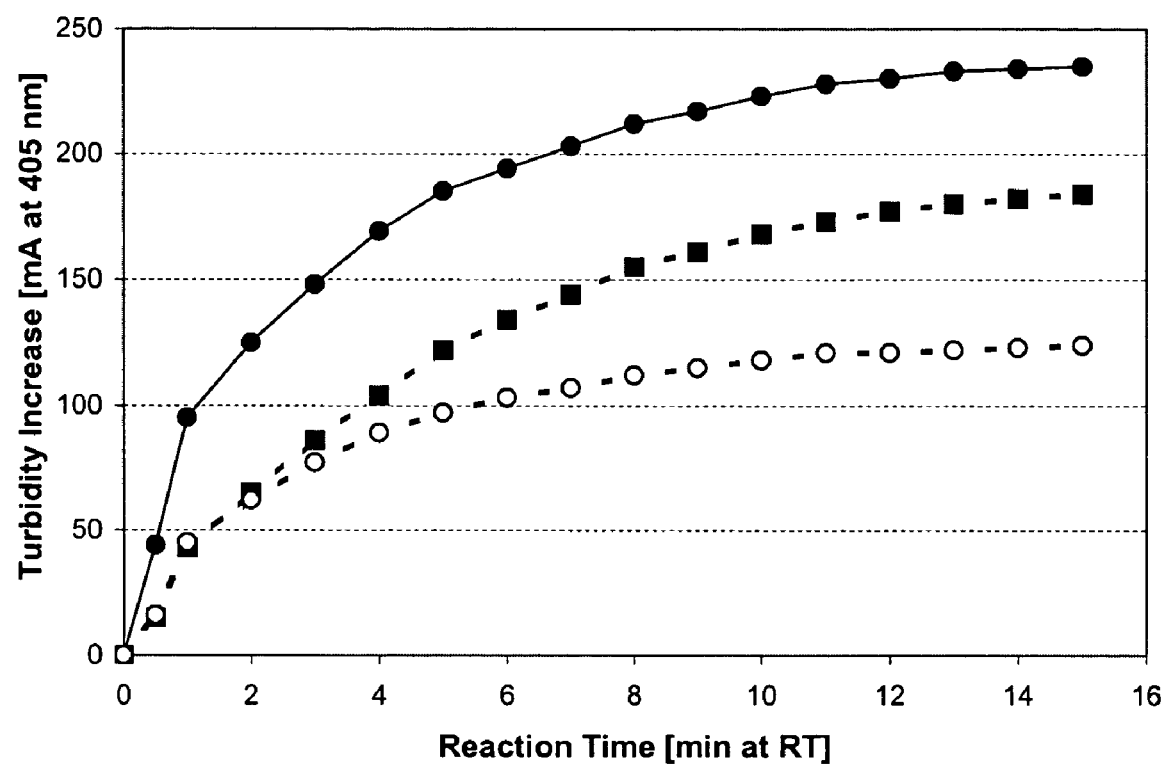
Fig. 6a: Albumin dependence

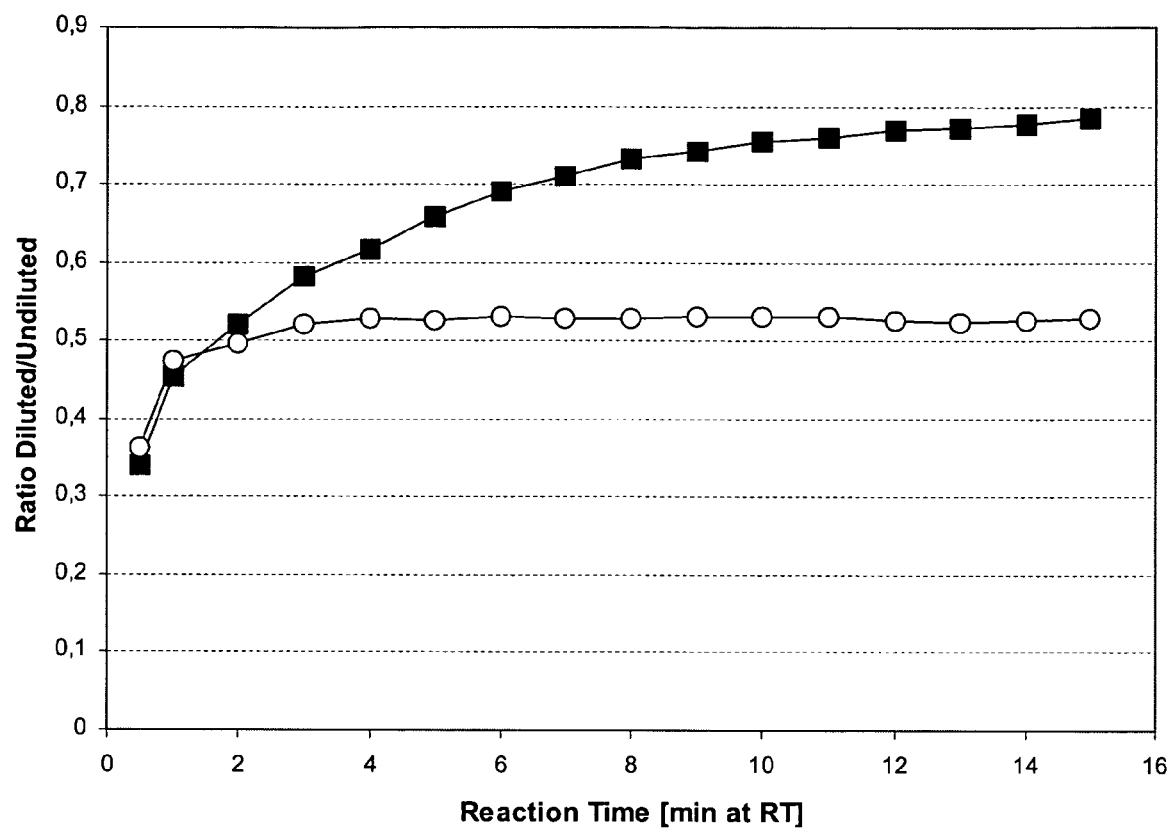
Fig. 6b: Albumin dependence

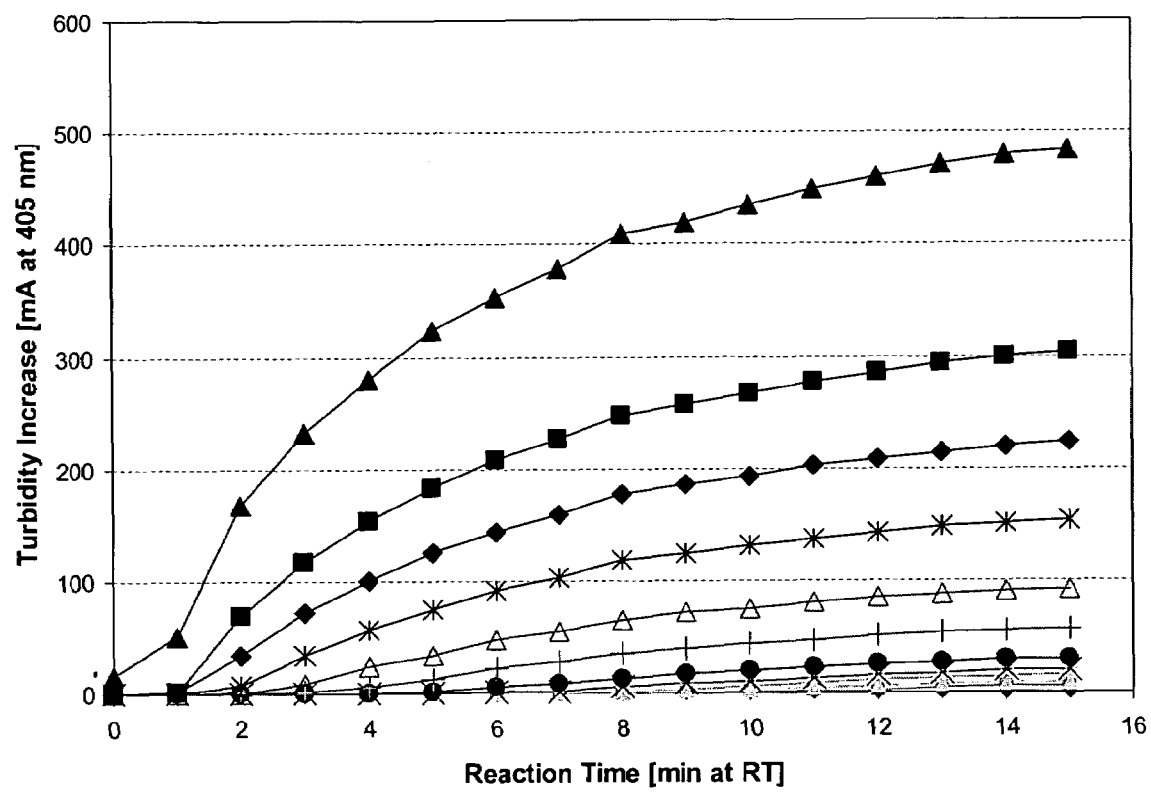
Fig. 7a: Reaction kinetic

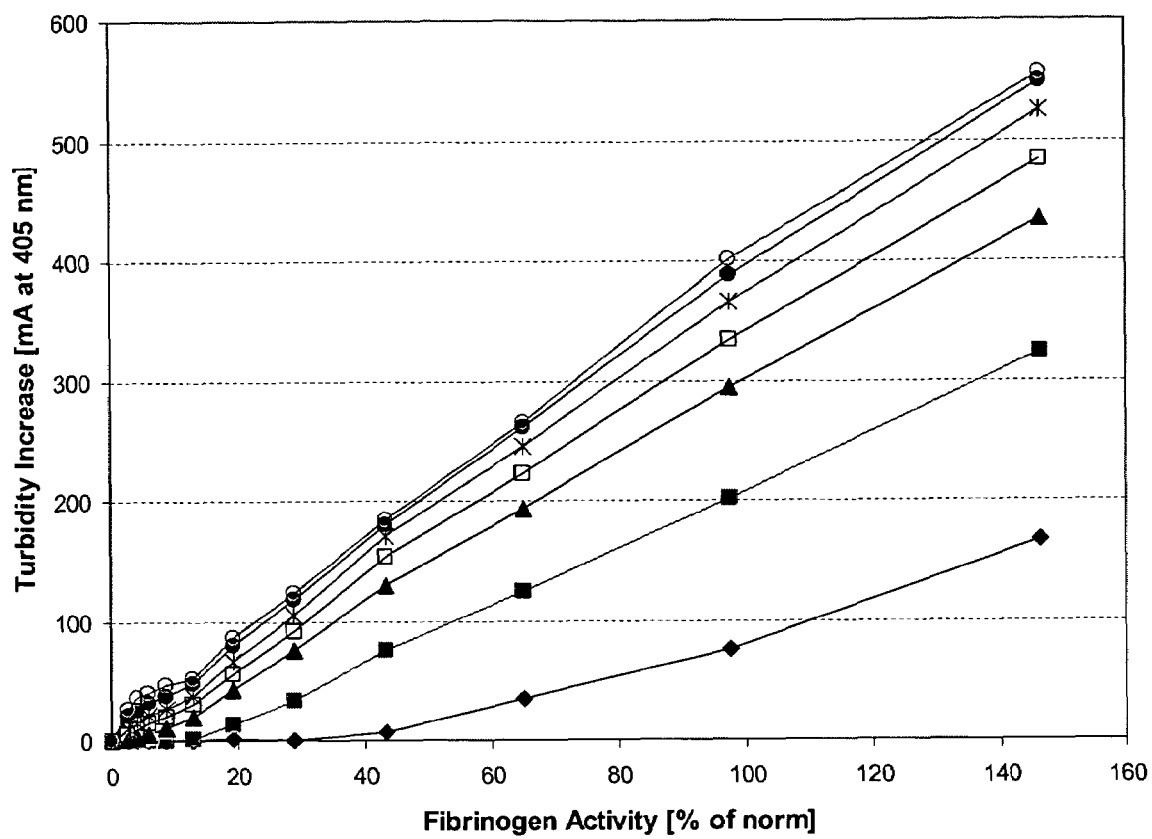
Fig. 7b: Reaction kinetic

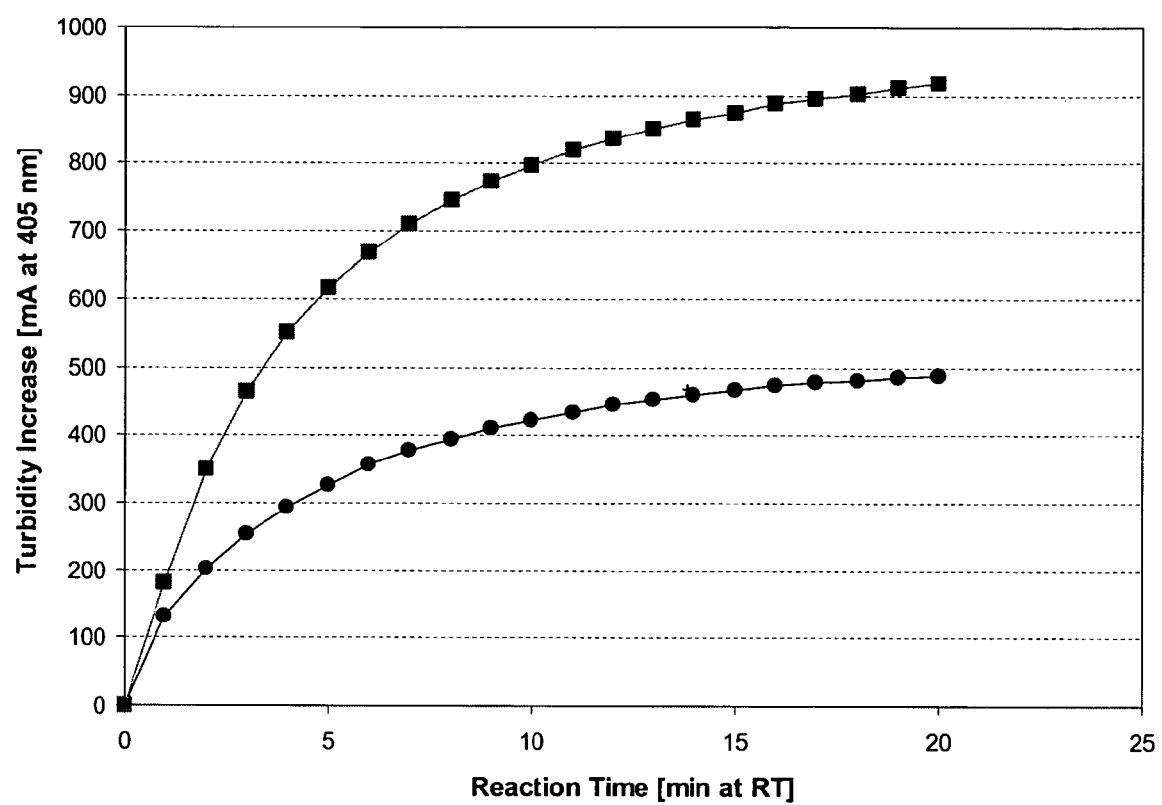
Fig. 7c: Reaction kinetic

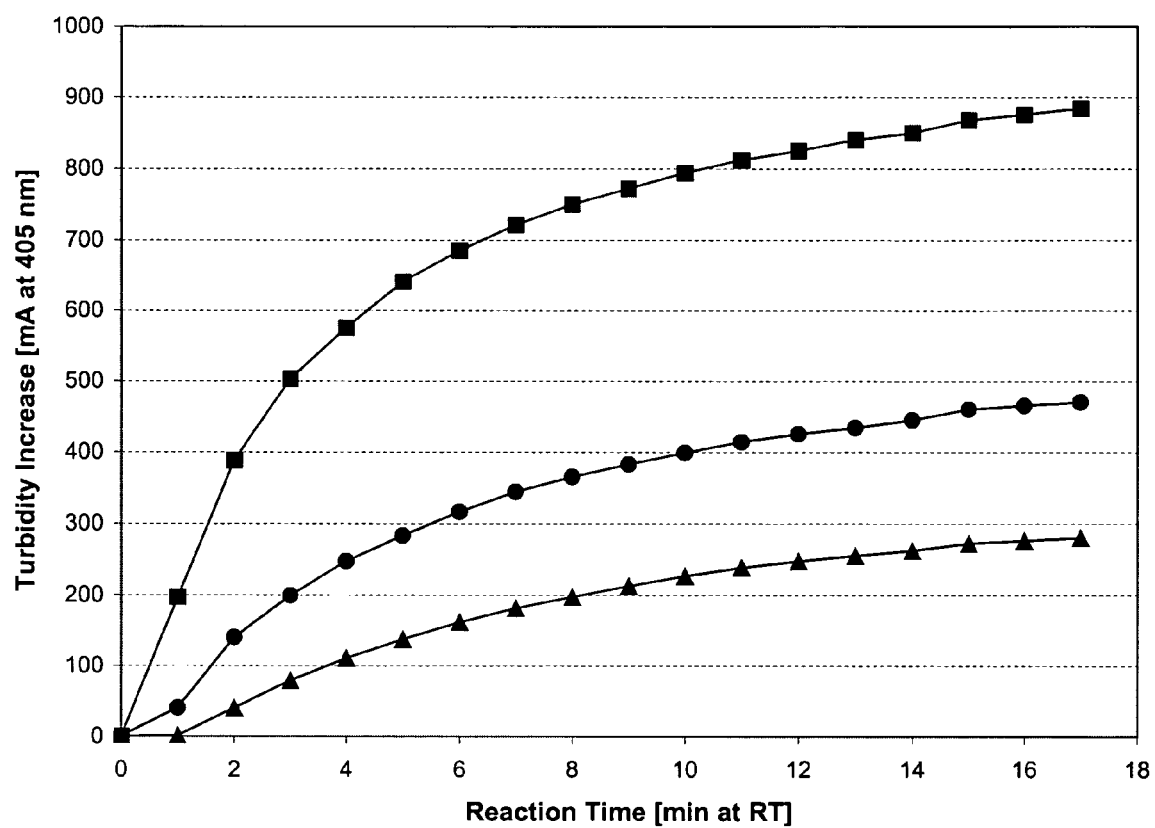
Fig. 7d: Reaction kinetic

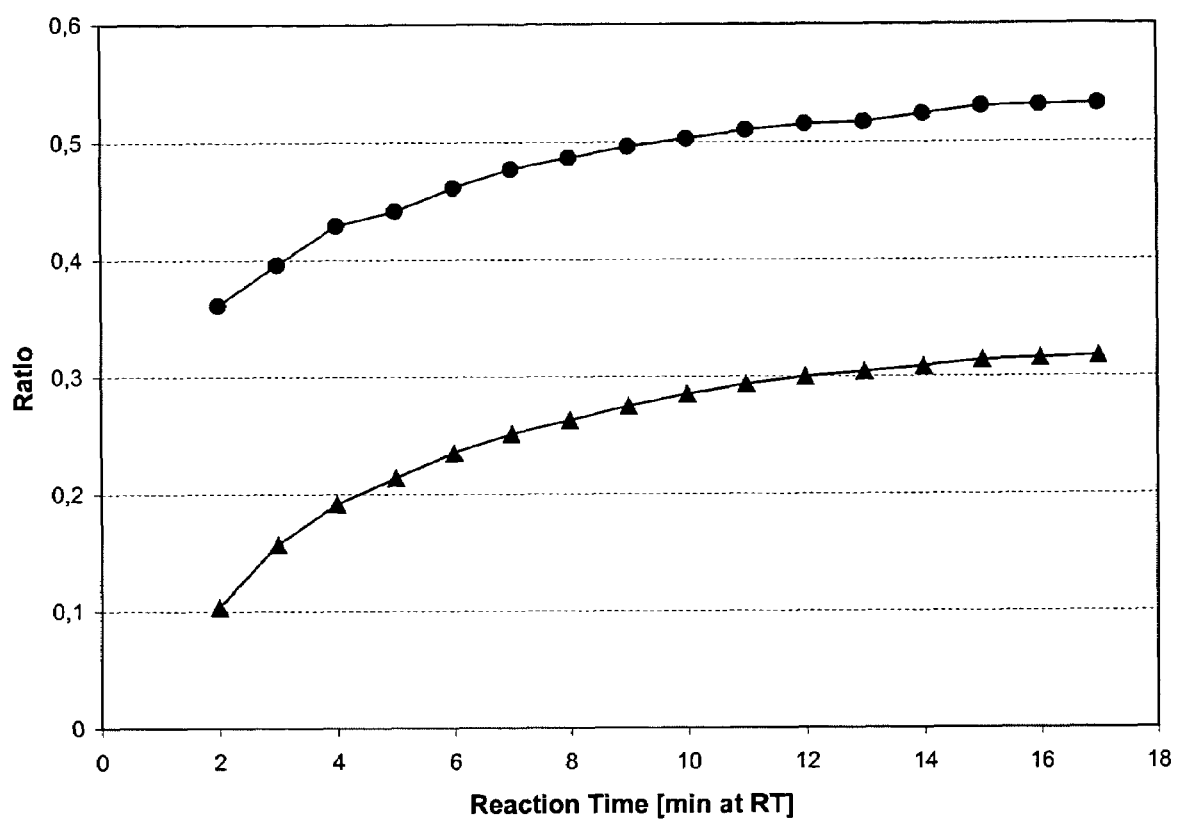
Fig. 7e: Reaction kinetic

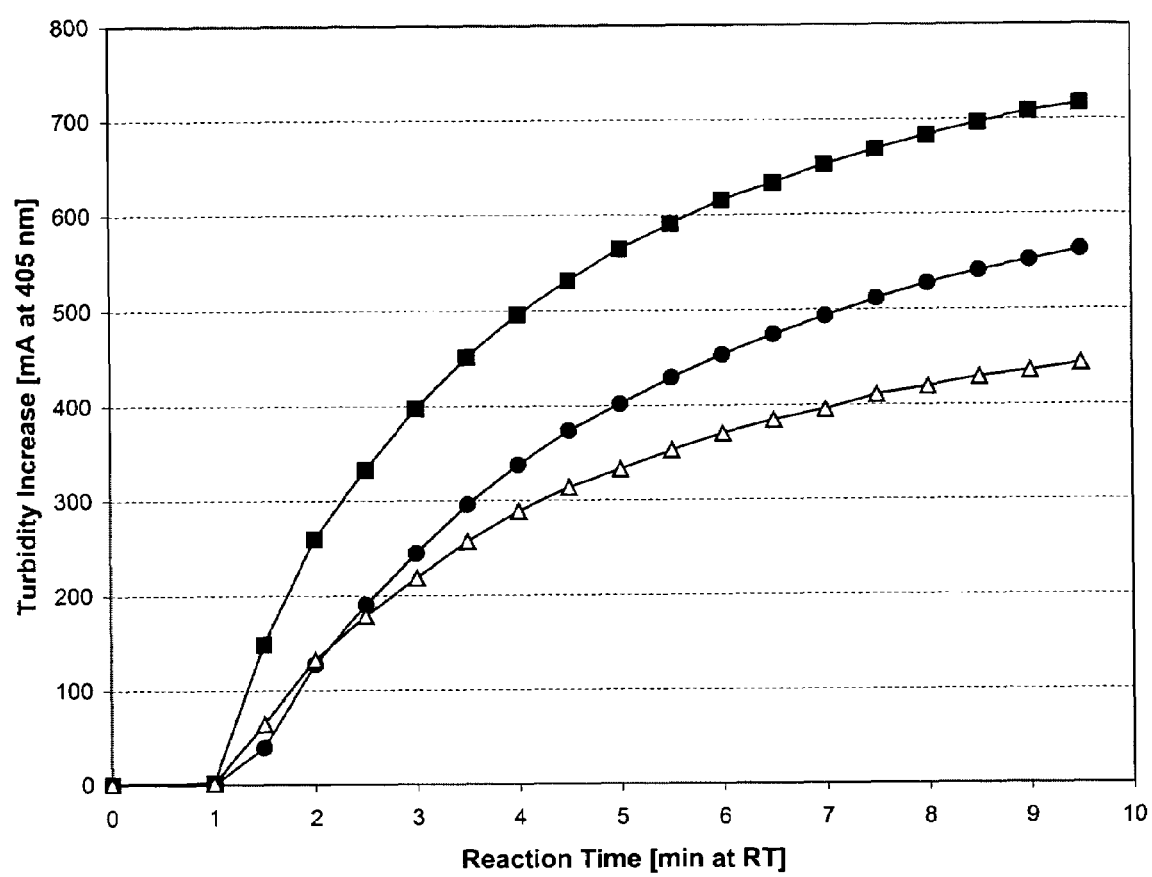
Fig. 7f: Reaction kinetic

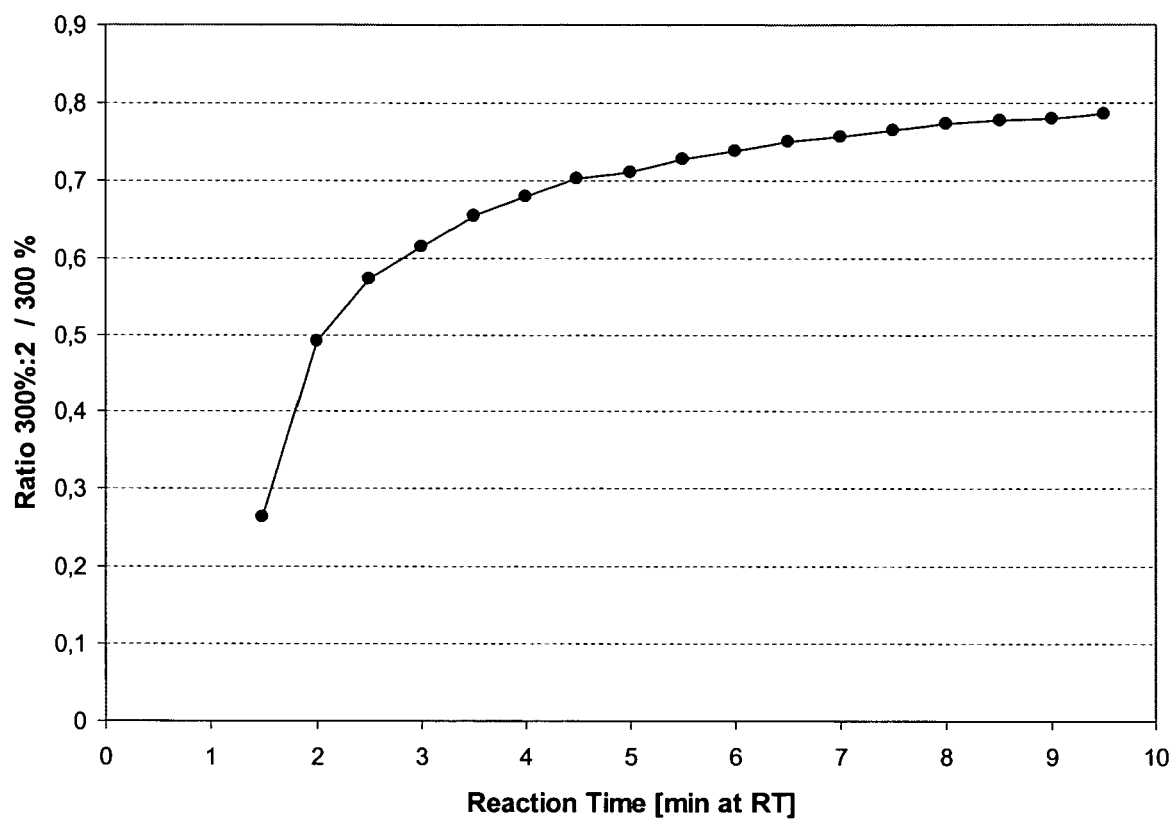
Fig. 7g: Reaction kinetic

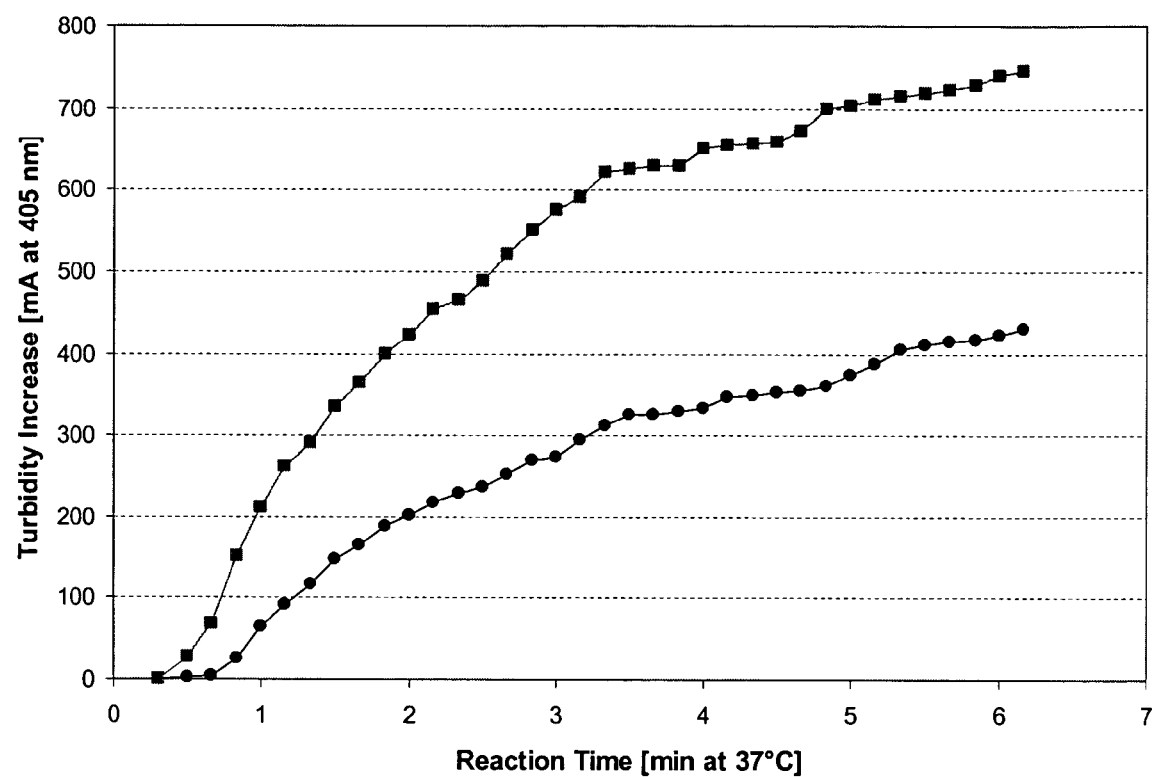
Fig. 8a: Reaction kinetic at 37°C

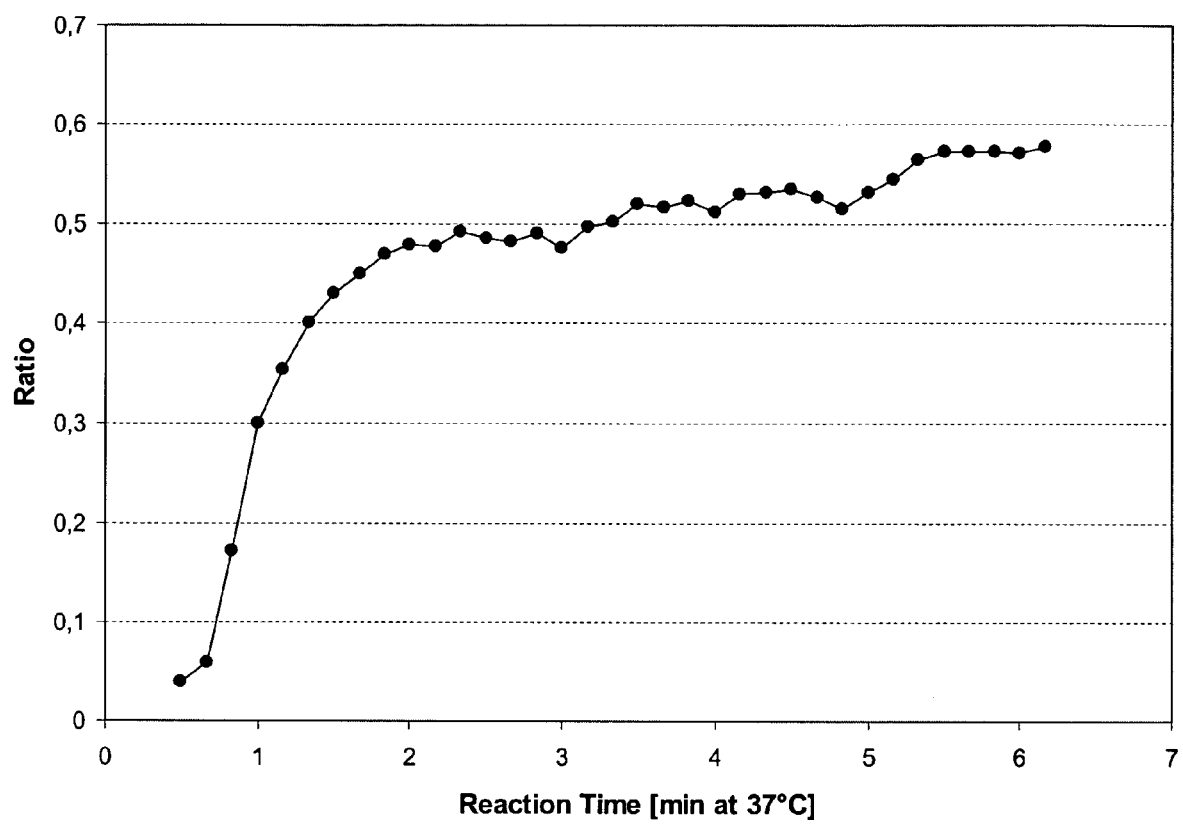
Fig. 8b: Reaction kinetic at 37°C

Fig. 9a: FIFTA linearity
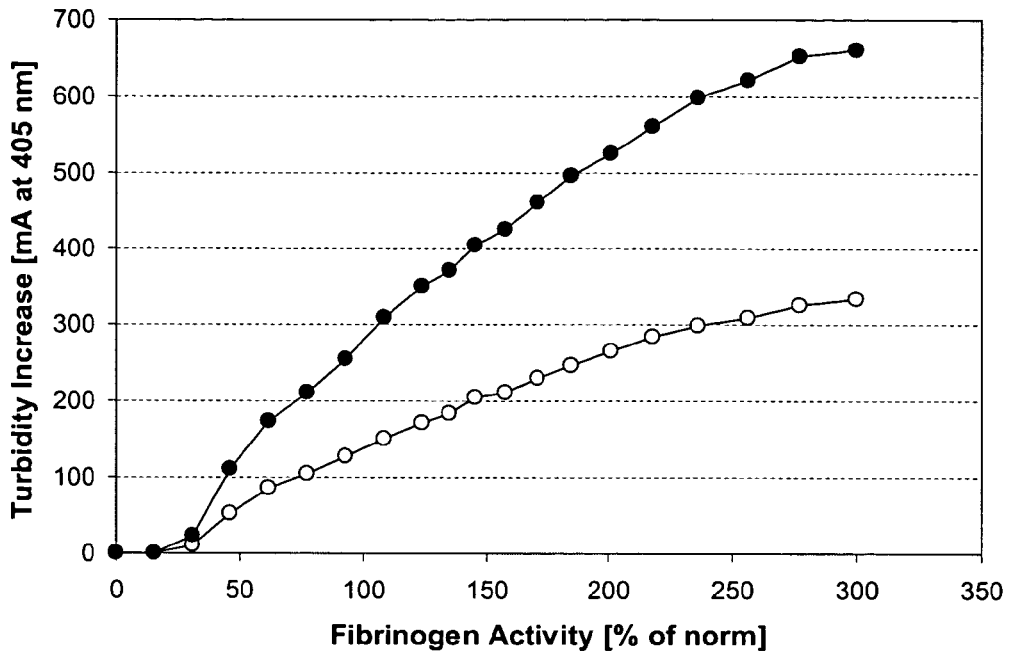
Fig. 9b: FIFTA Linearity
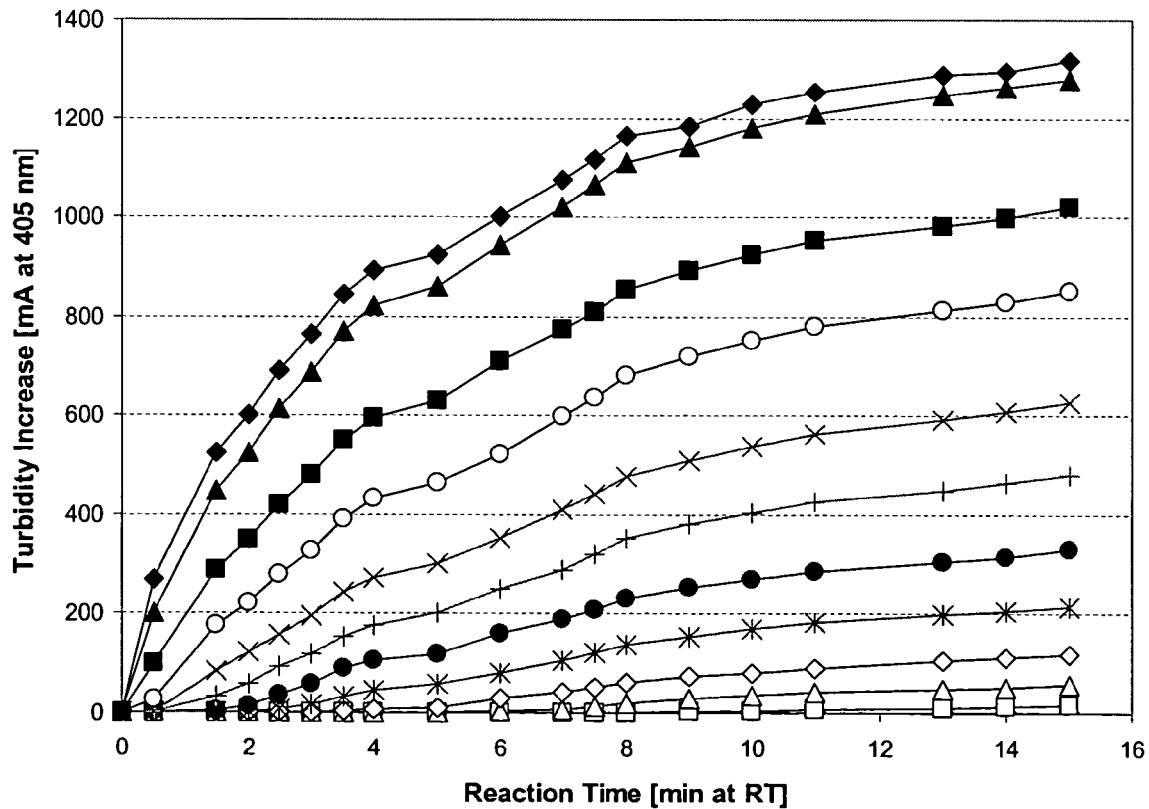

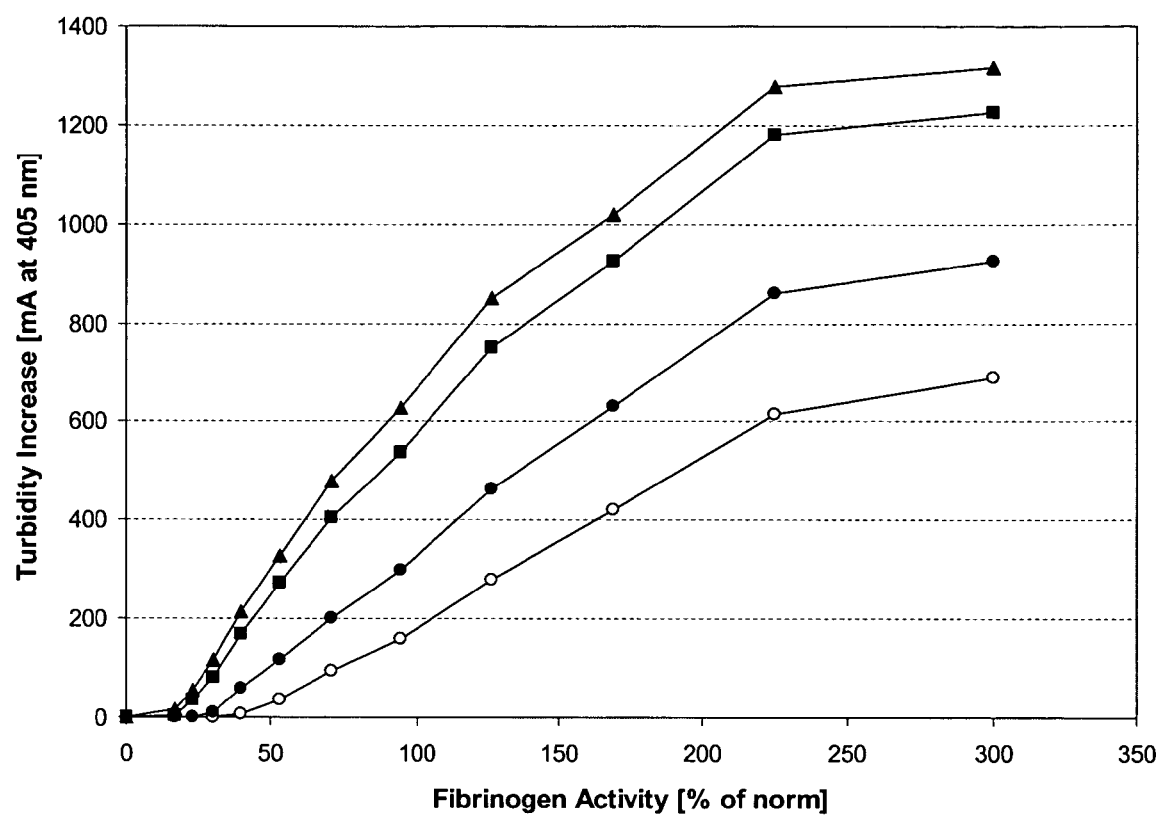
Fig. 9c: FIFTA-linearity

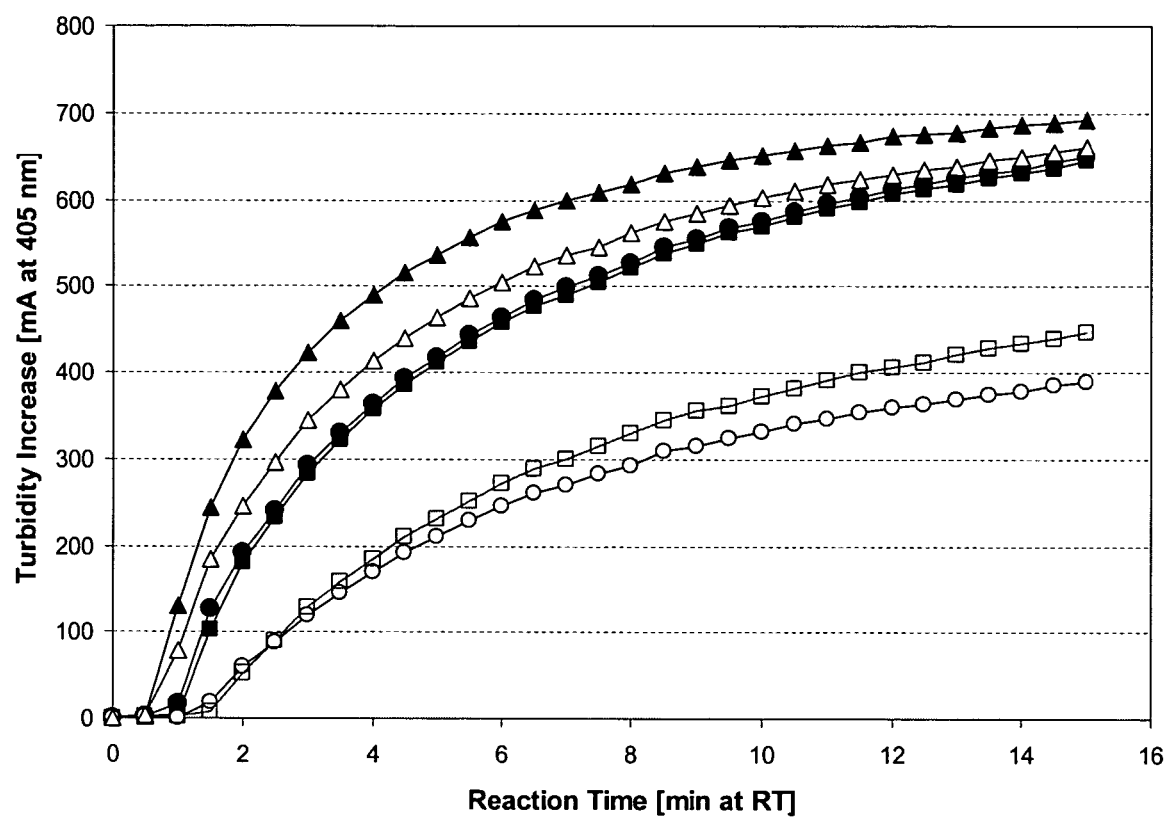
Fig. 10a: Variation of assay volumina

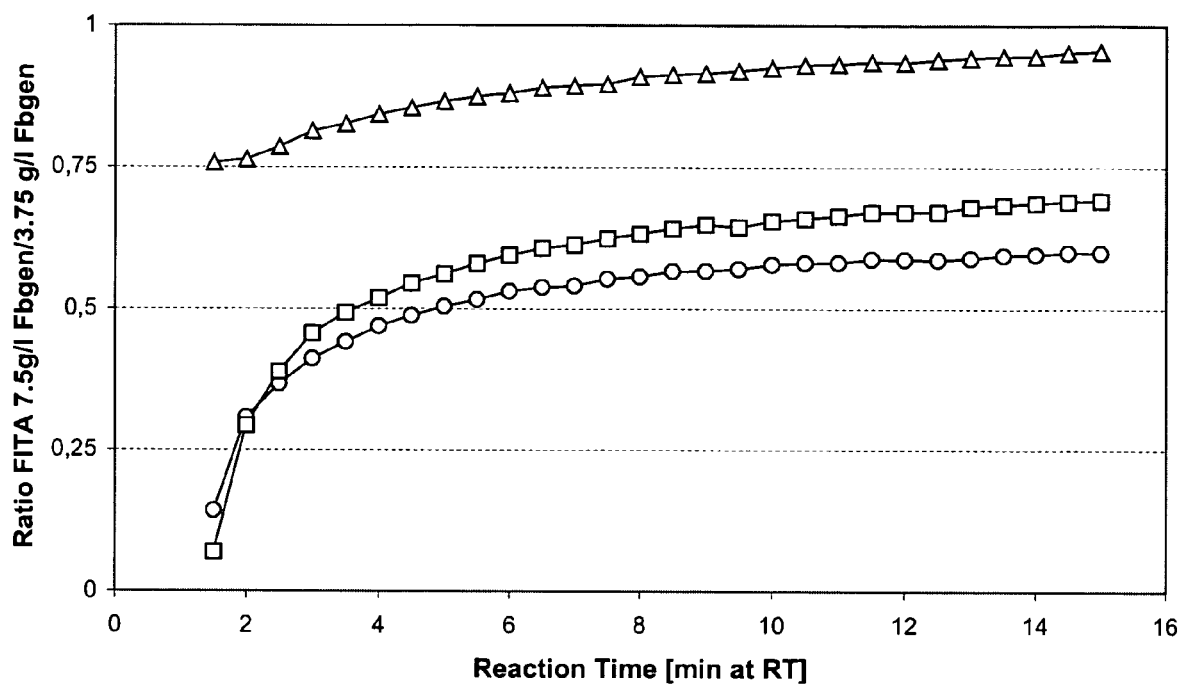
Fig. 10b: Variation of assay volumina

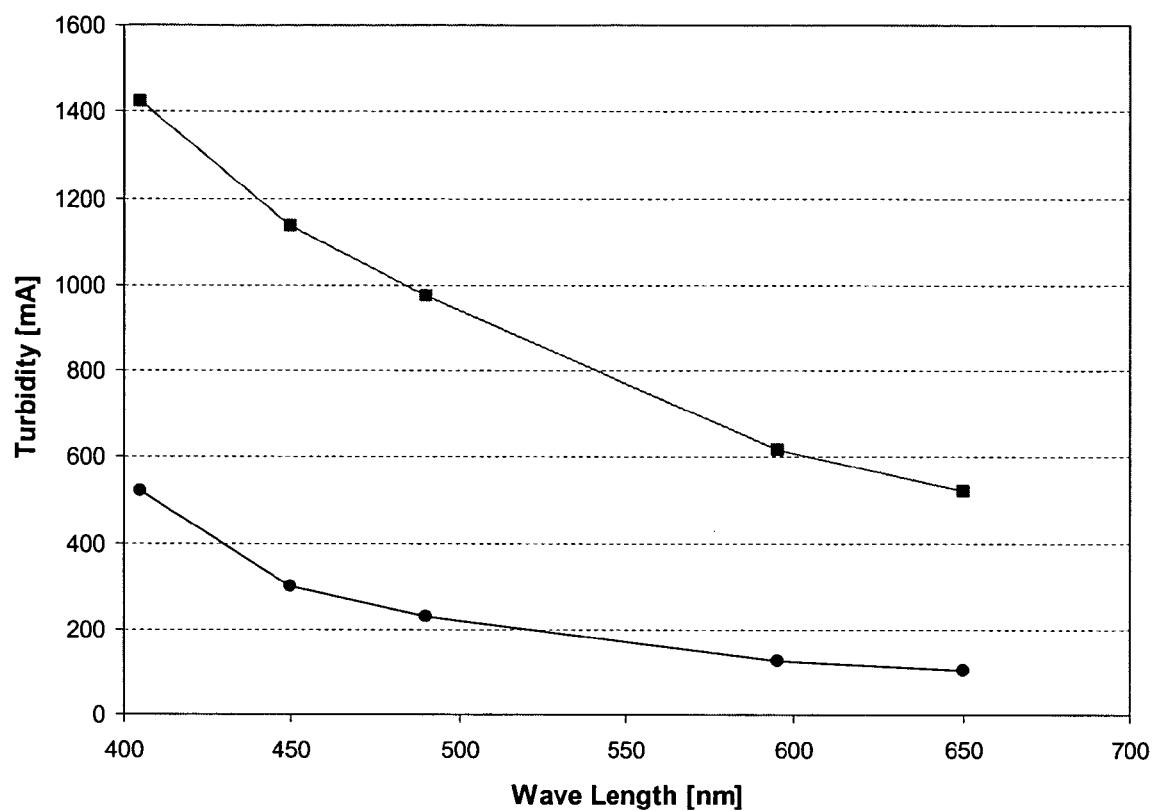
Fig. 11: Absorbance wavelength for turbidity

Fig. 12a: FIFTA calibration with purified fibrinogen
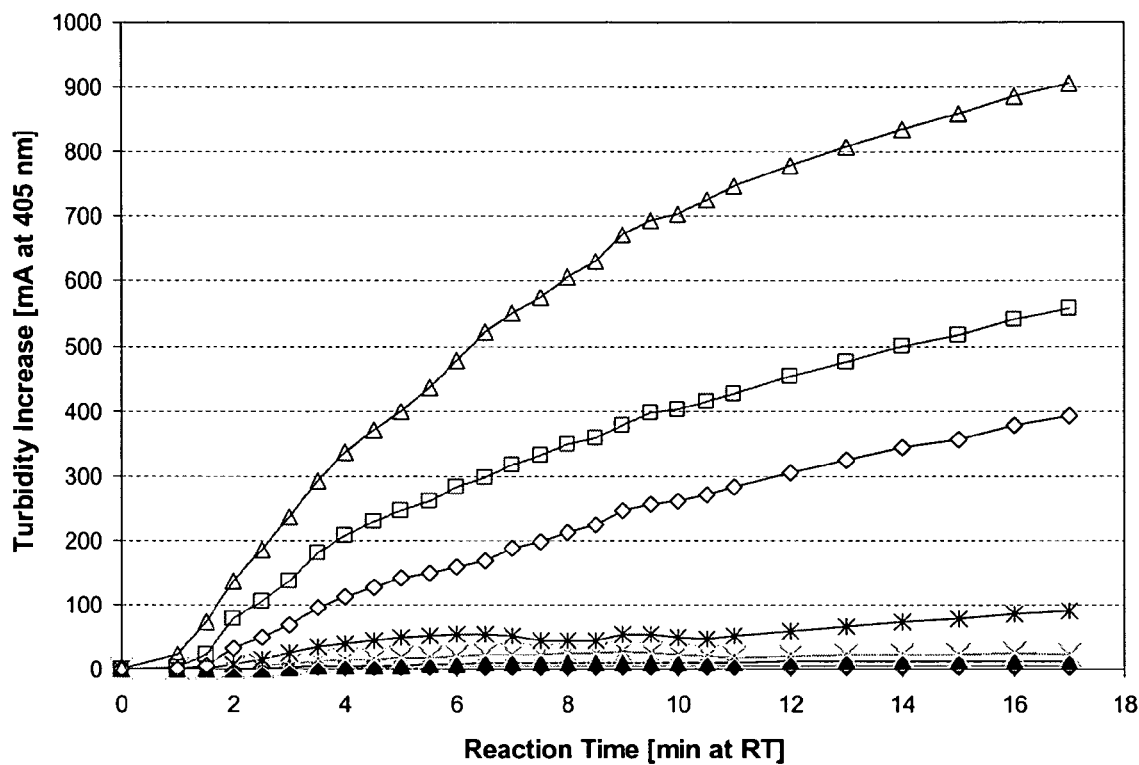
Fig. 12b: FIFTA calibration with purified fibrinogen
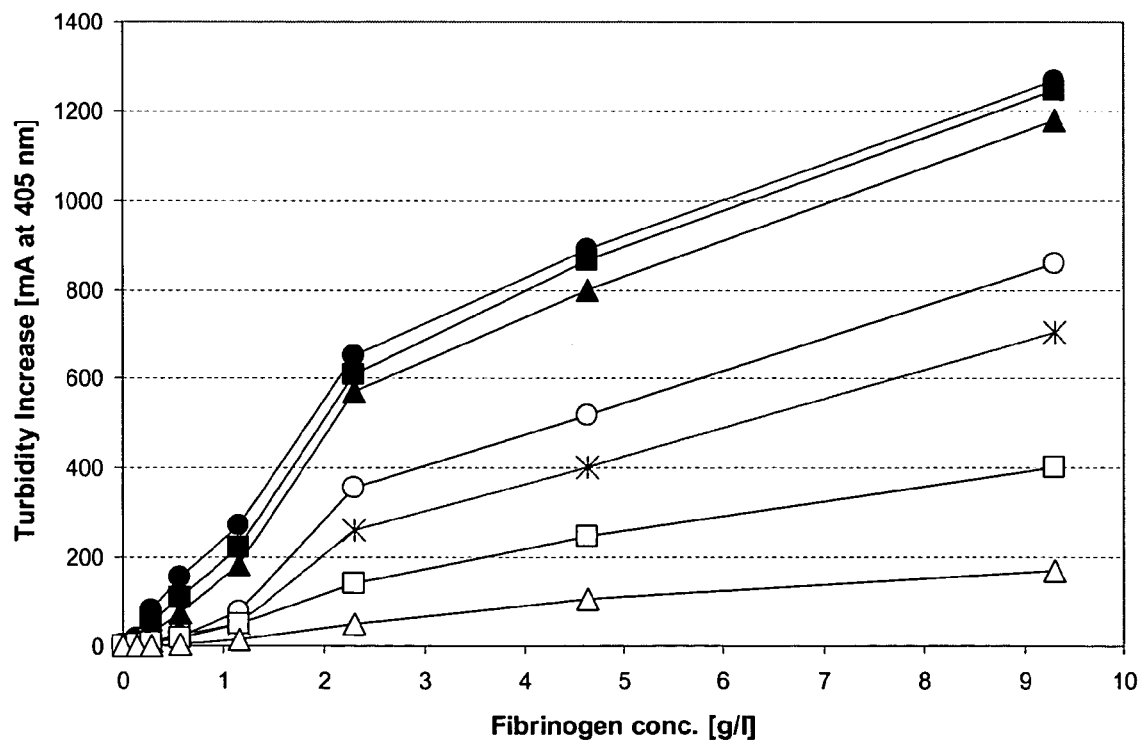

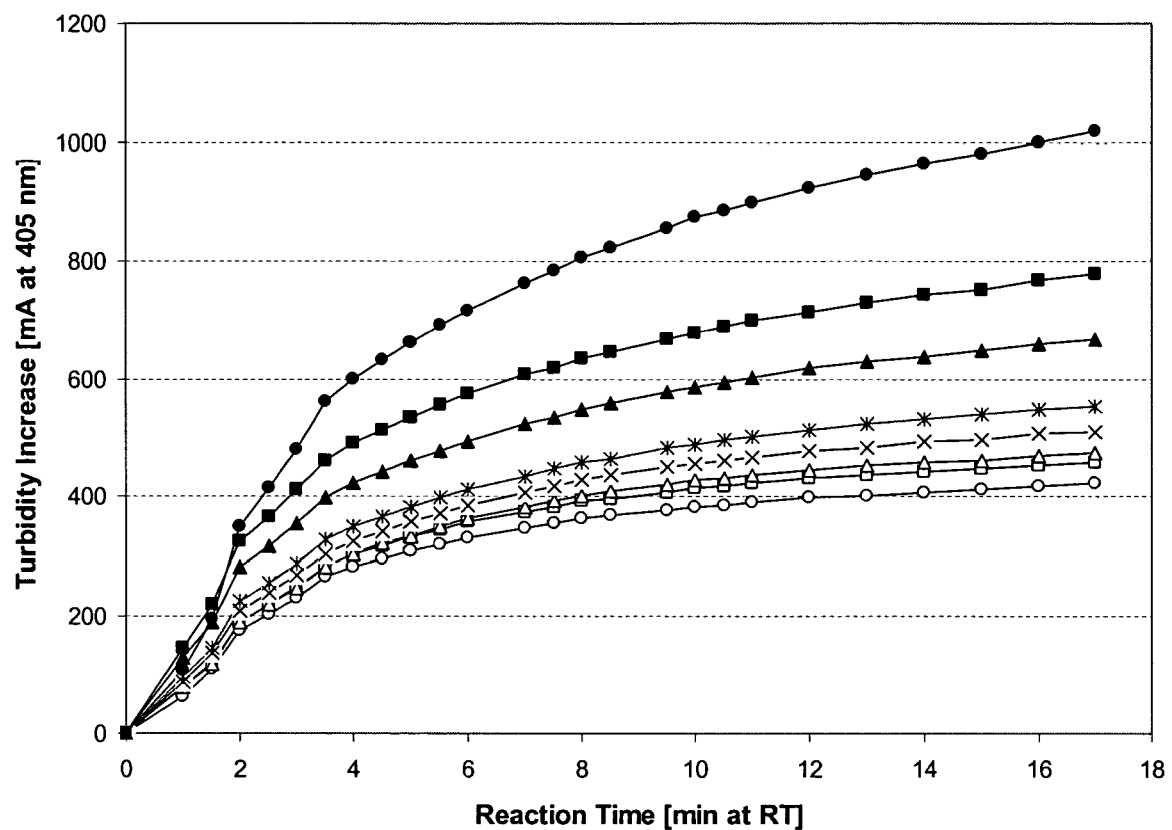
Fig. 12c: FIFTA calibration with purified fibrinogen

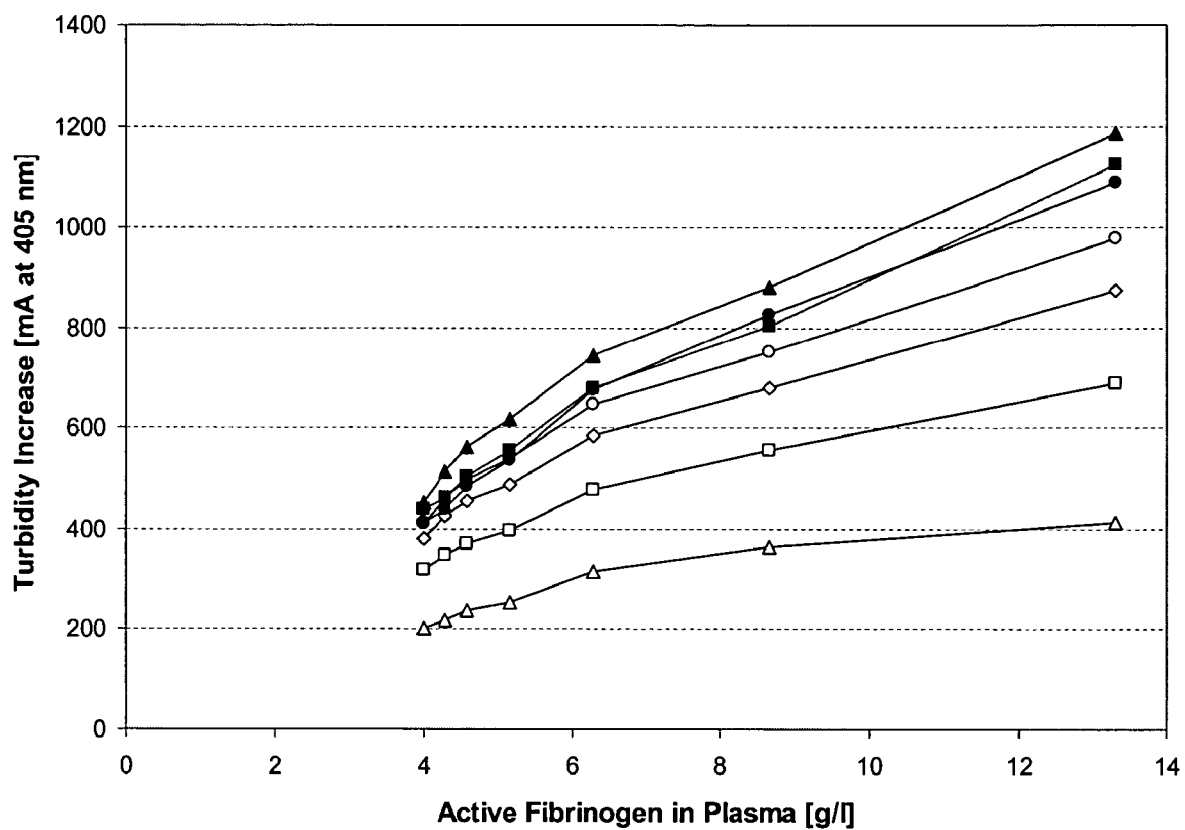
Fig. 12d: FIFTA calibration with purified fibrinogen

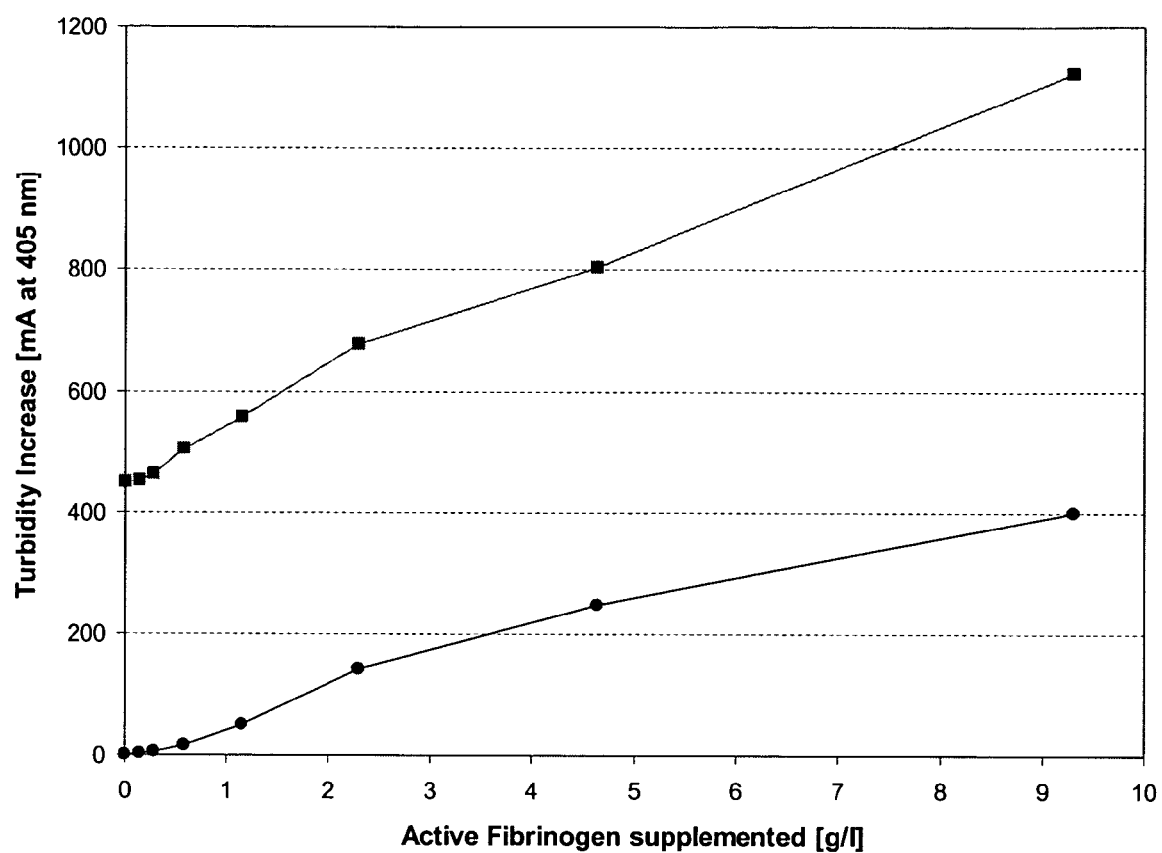
Fig. 12e: FIFTA calibration with purified fbgen

Fig. 13a: Correlation with Clauss-method
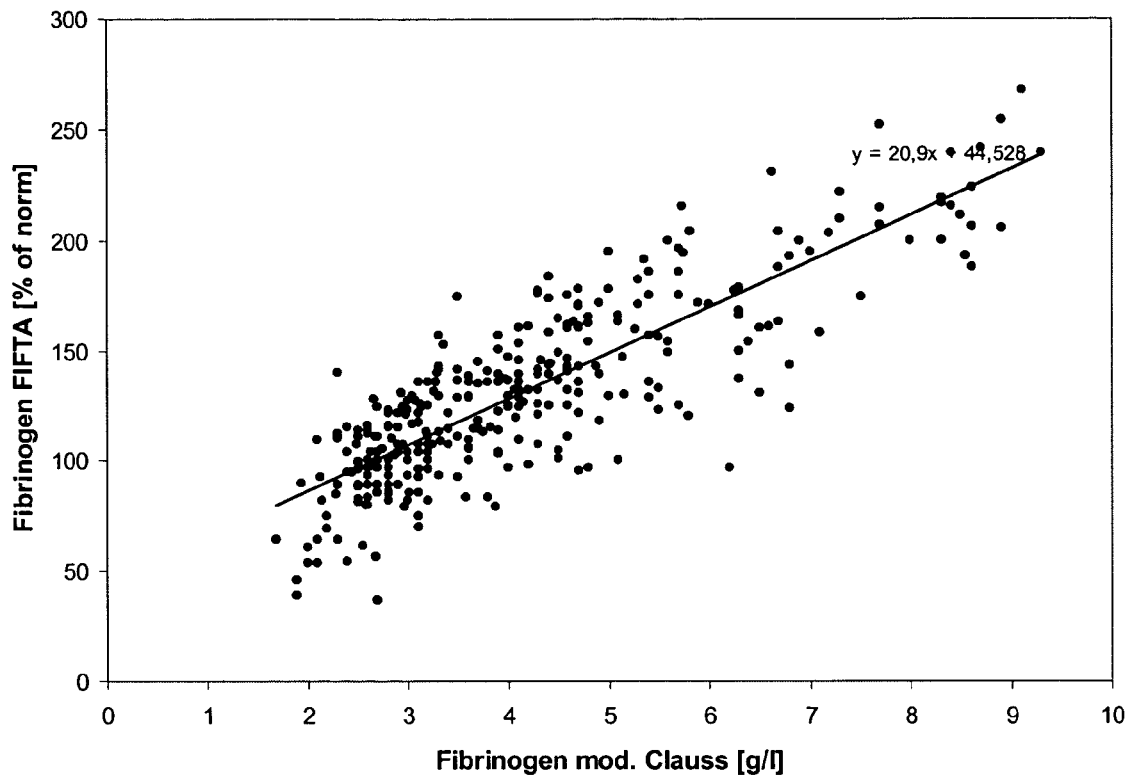
Fig. 13b: FIFTA distribution in patients
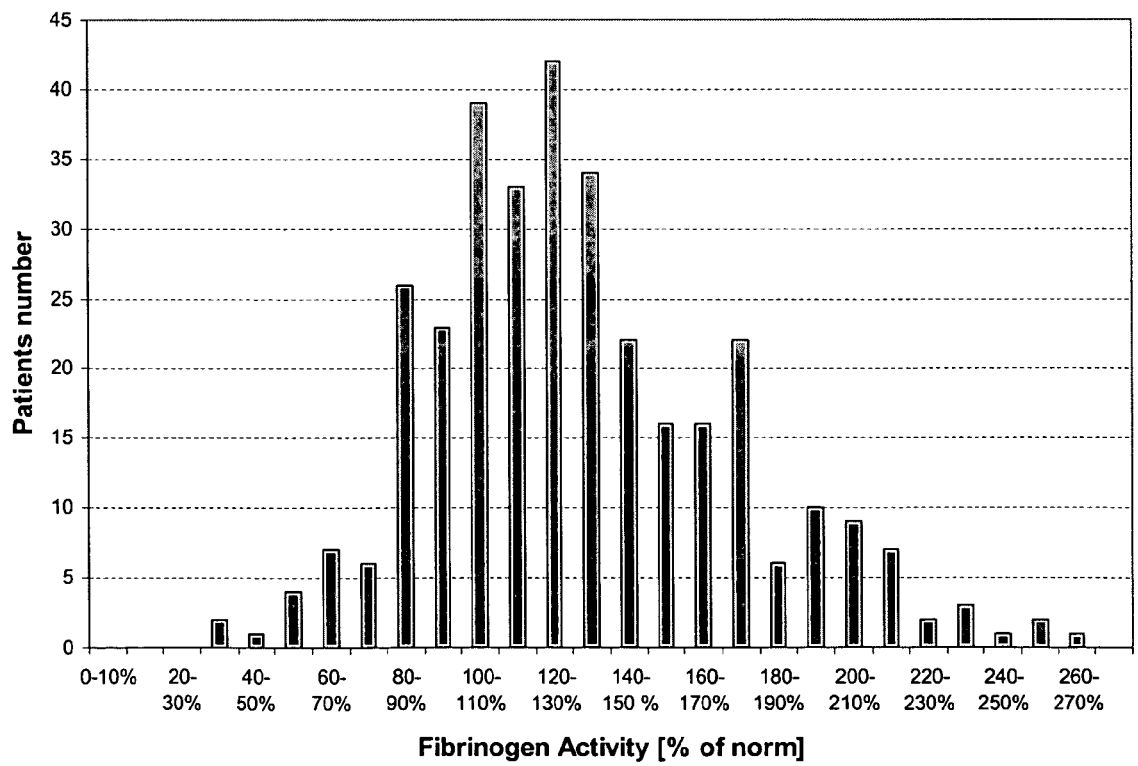

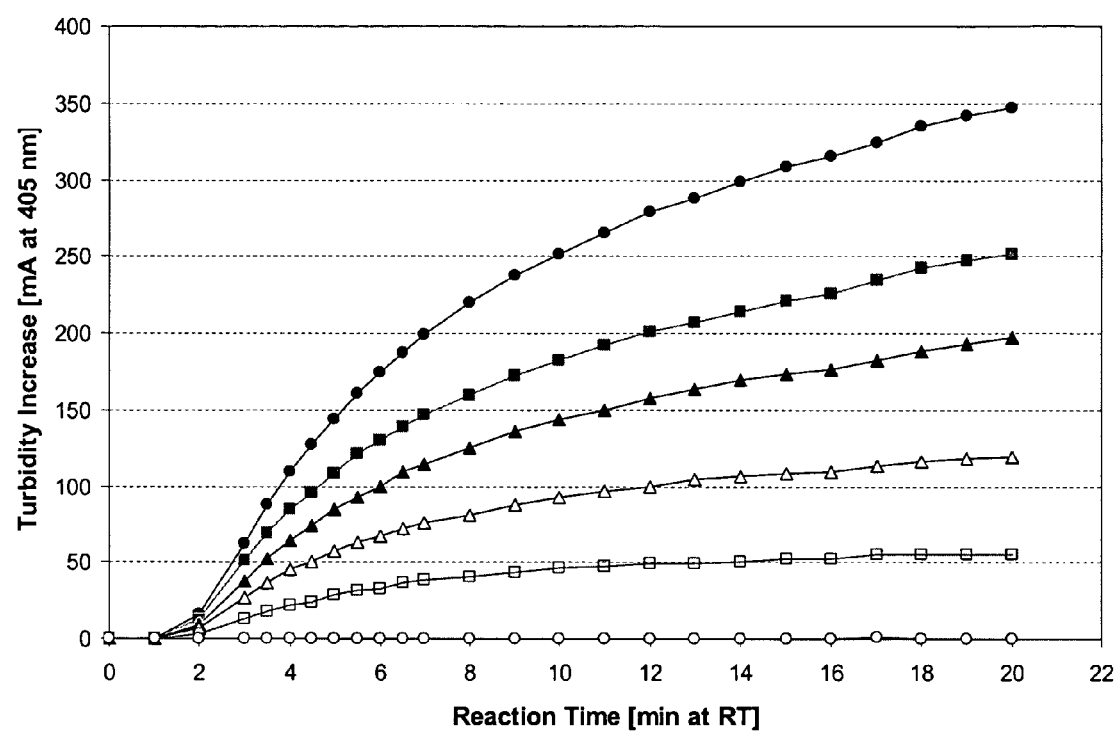
Fig. 14a: IC50 of heparin in the FIFTA

Fig. 14b: IC50 of heparin in the FIFTA
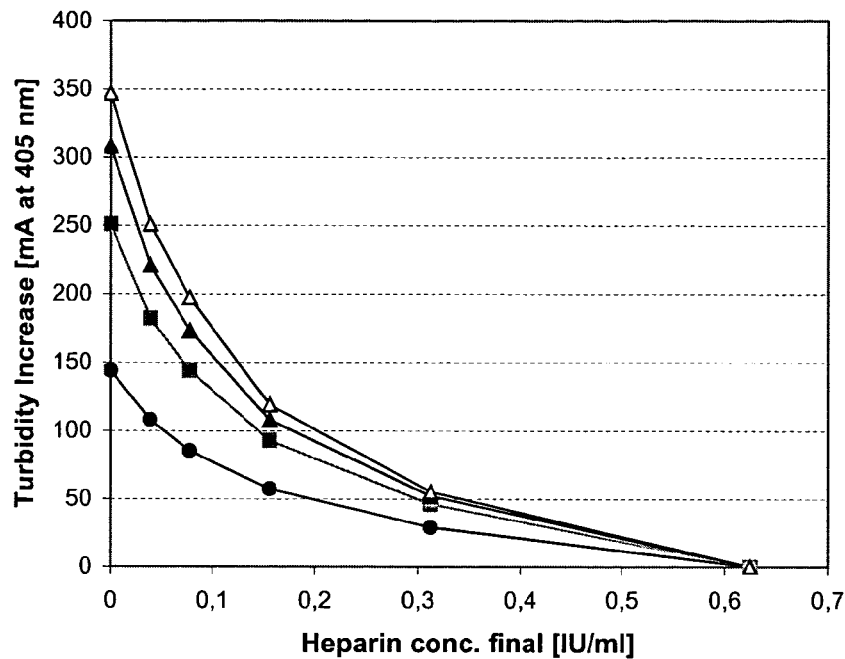
Fig. 15a: Inhibitory time point 50 % for heparin in the FIFTA
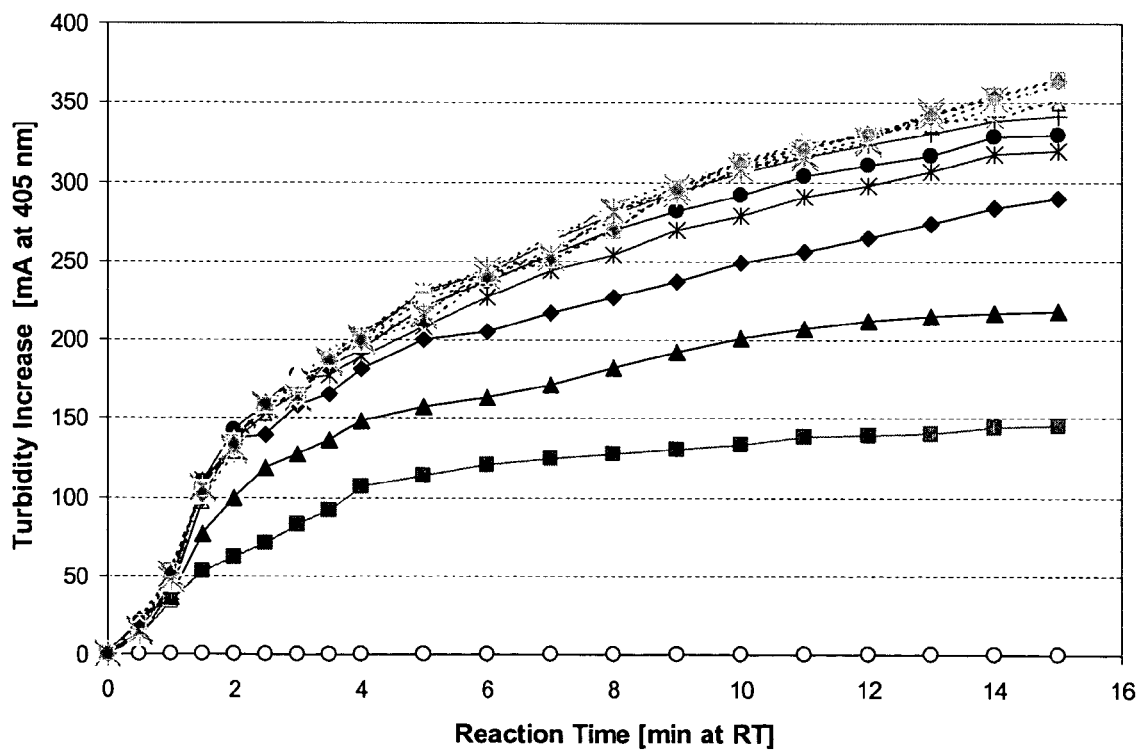

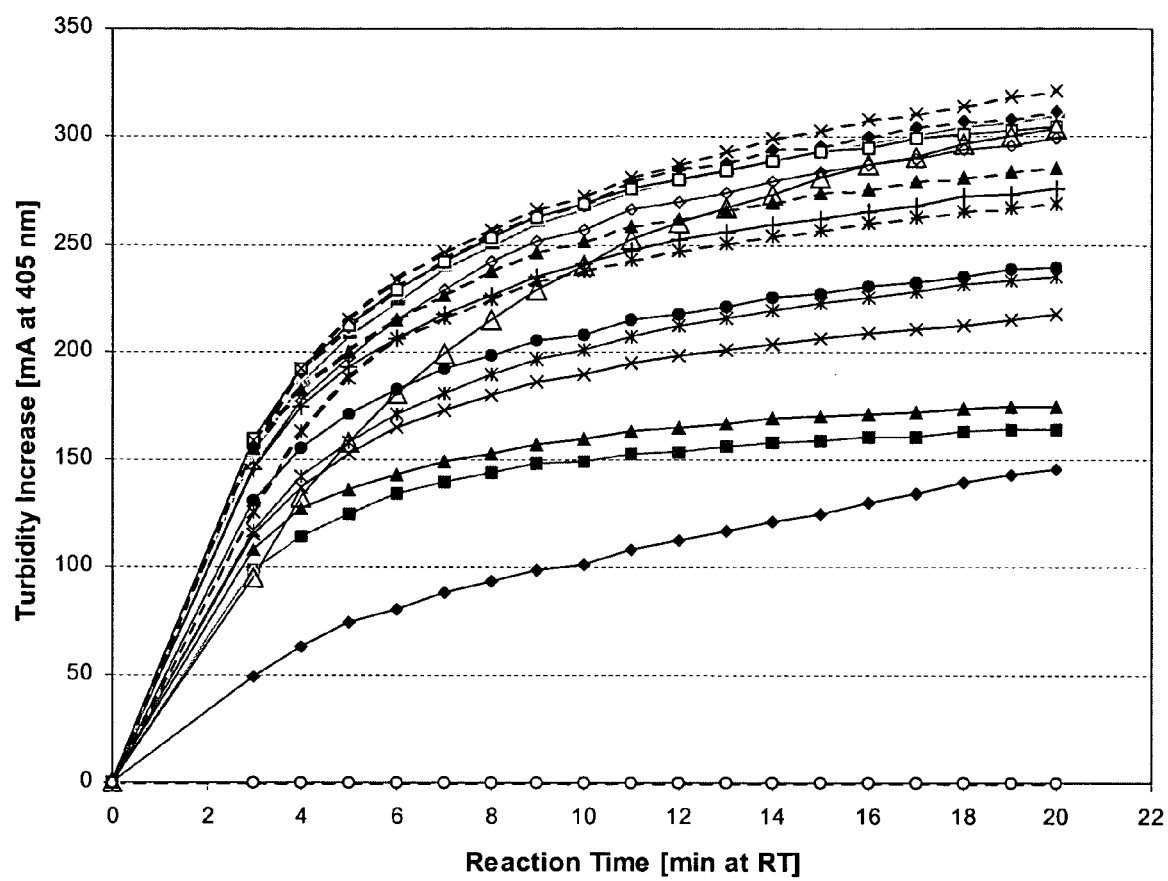
Fig. 15b: Inhibitory time point 50 %

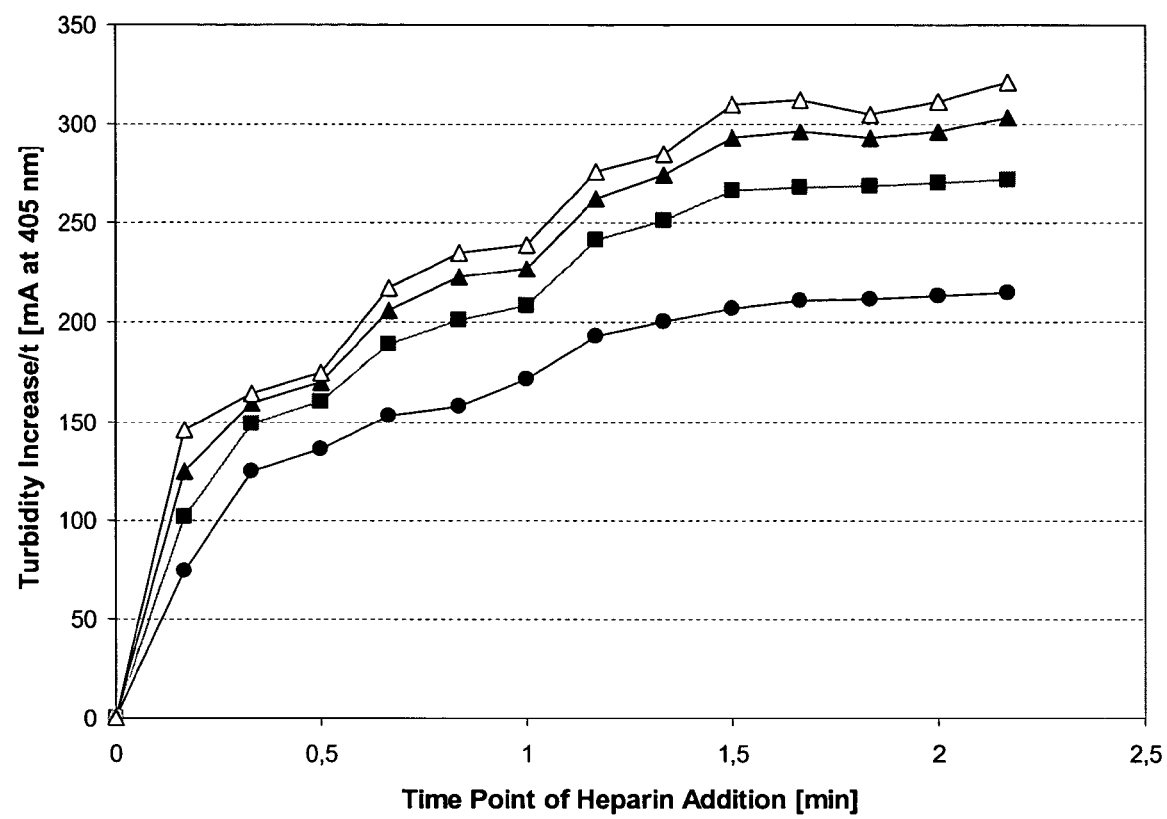
Fig. 15c: Inhibitory time point 50 %

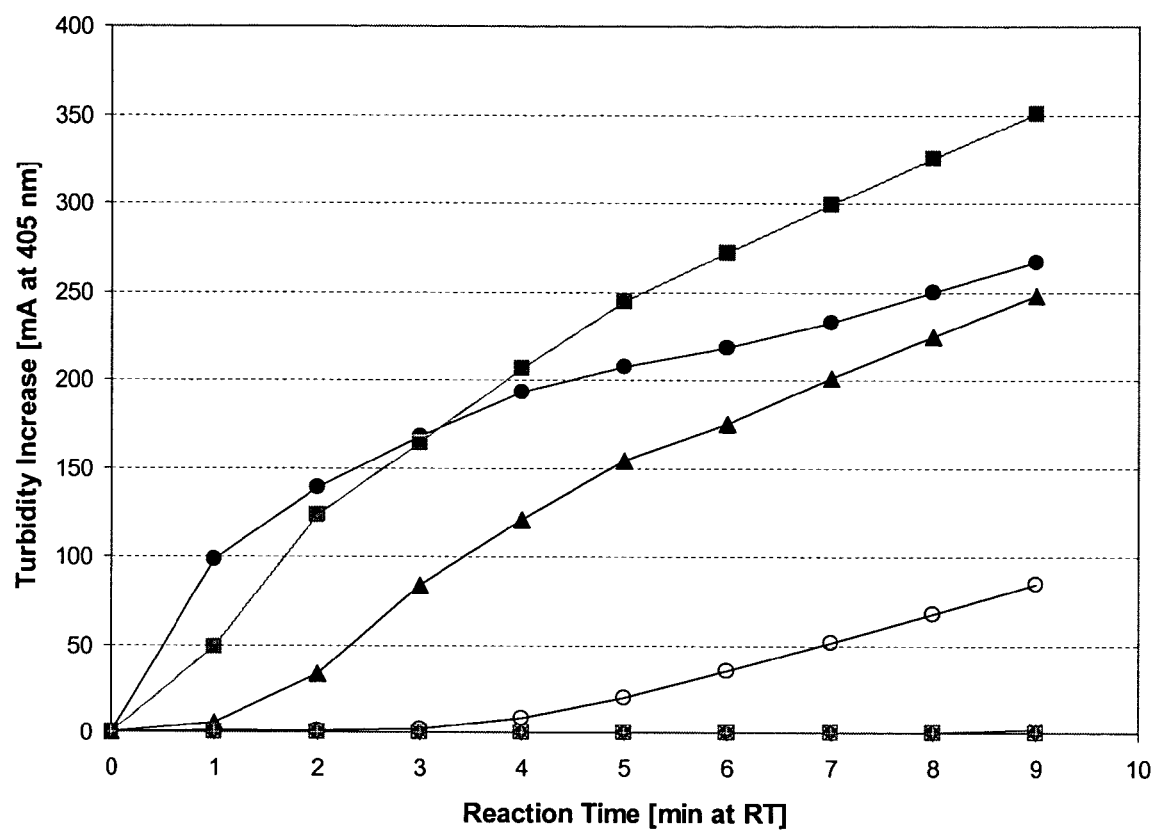
Fig. 16a: Inhibition of fibrin generation by arginine

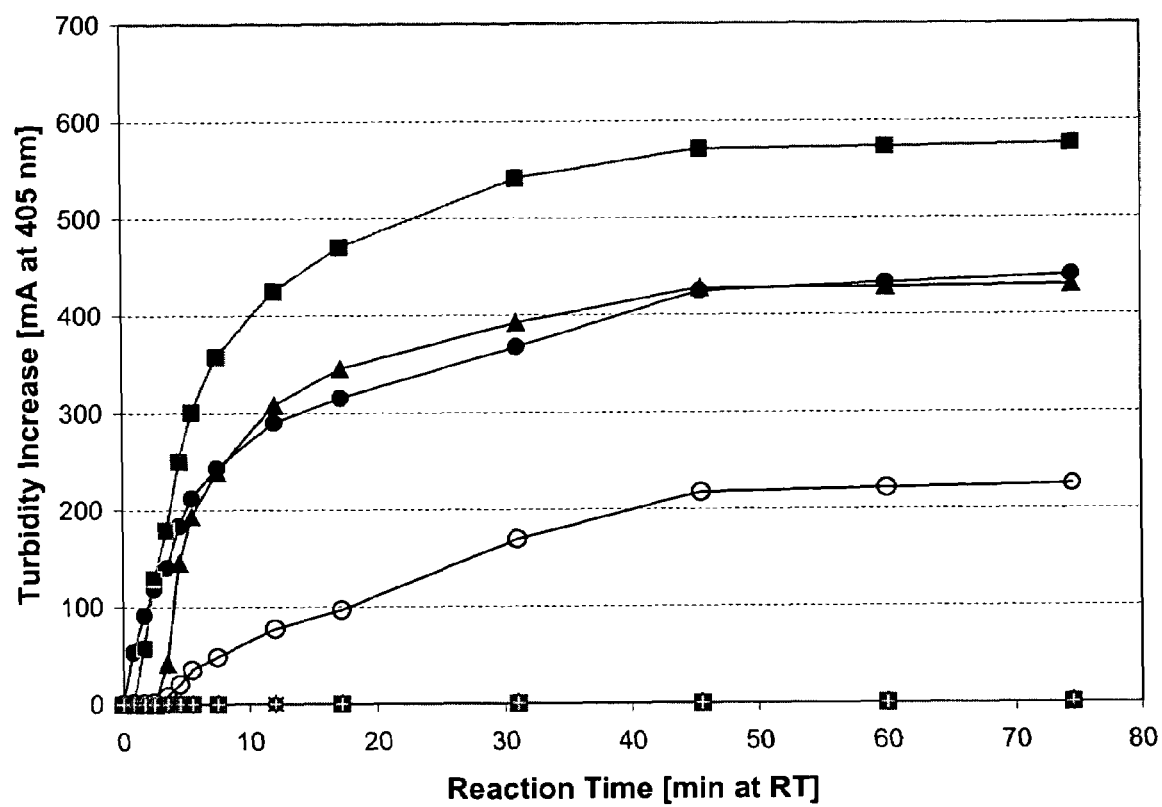
Fig. 16b: Inhibition of fibrin generation by arginine

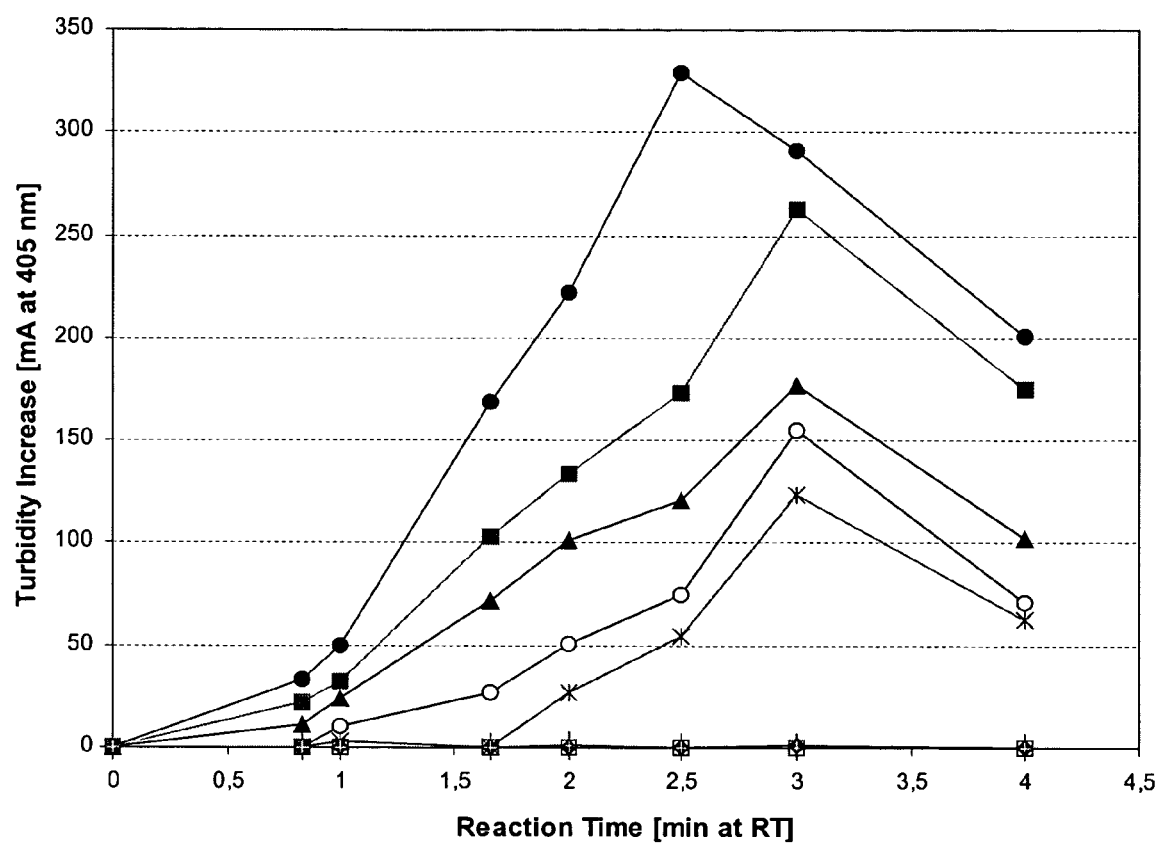
Fig. 16c: Inhibition of fibrin generation by arginine

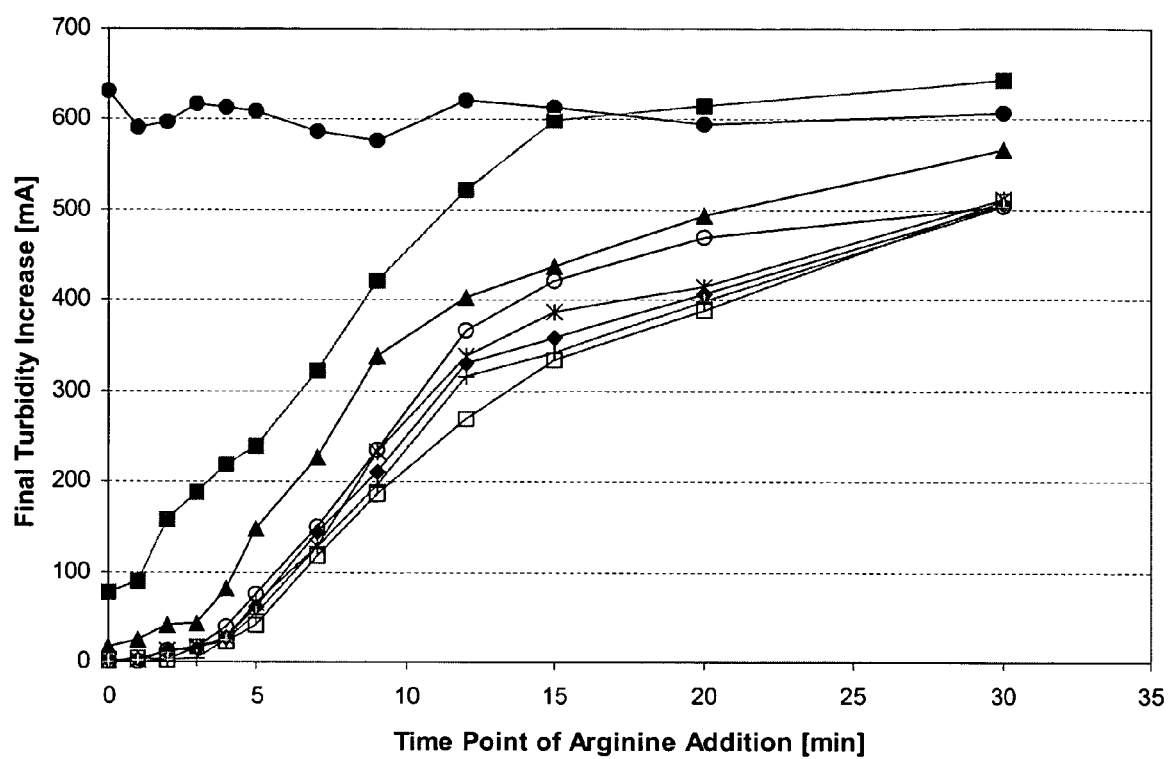
Fig. 16d: Inhibition of fibrin generation by arginine

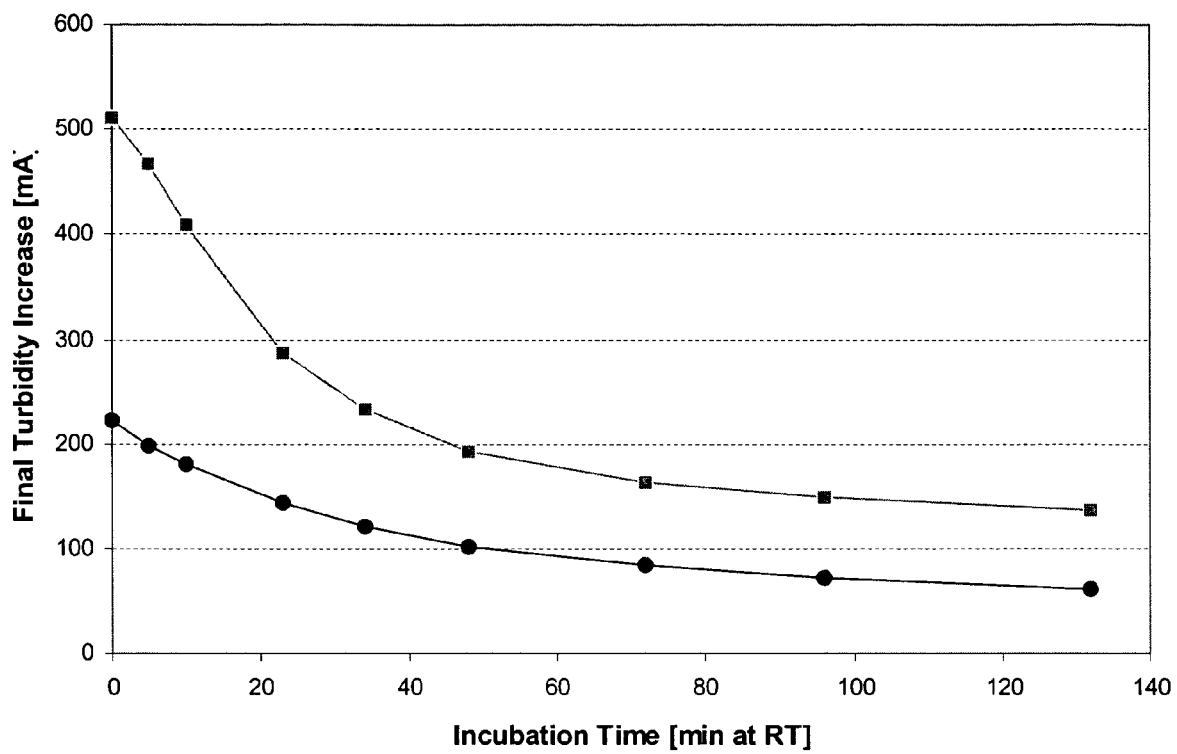
Fig. 17: Fibrin dissolution by arginine

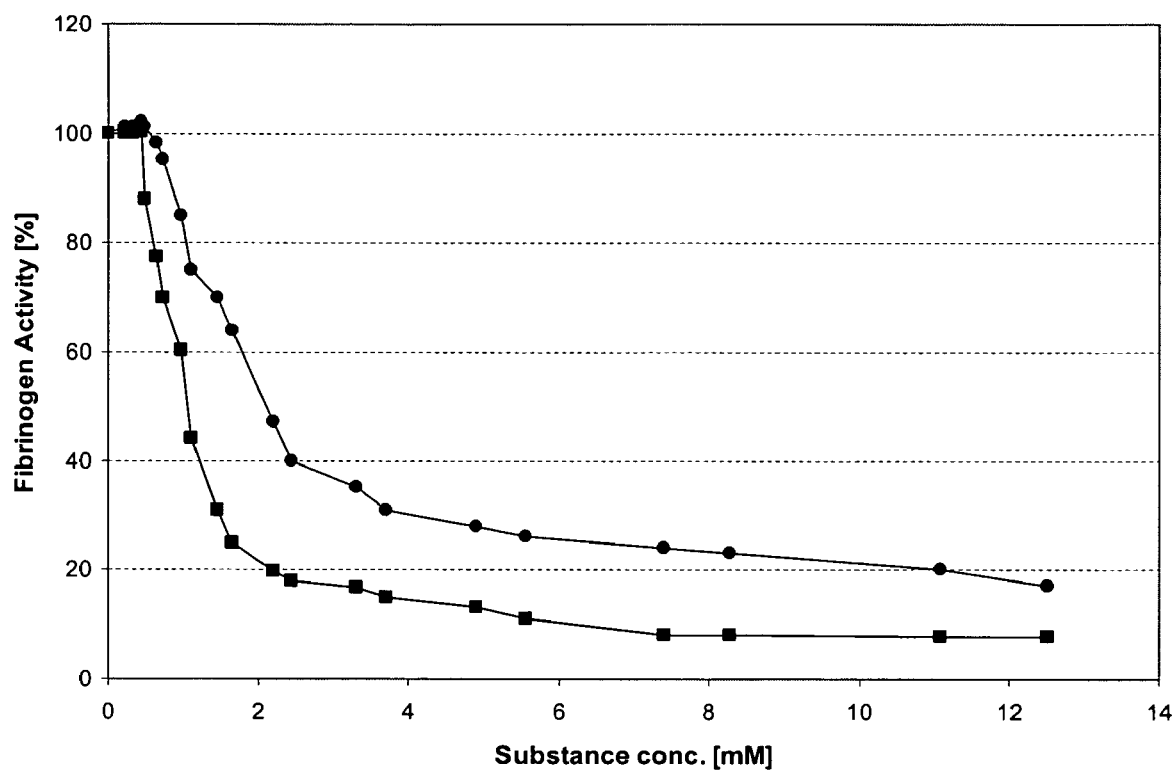
Fig. 18: Inactivation of fibrinogen by vancomycin

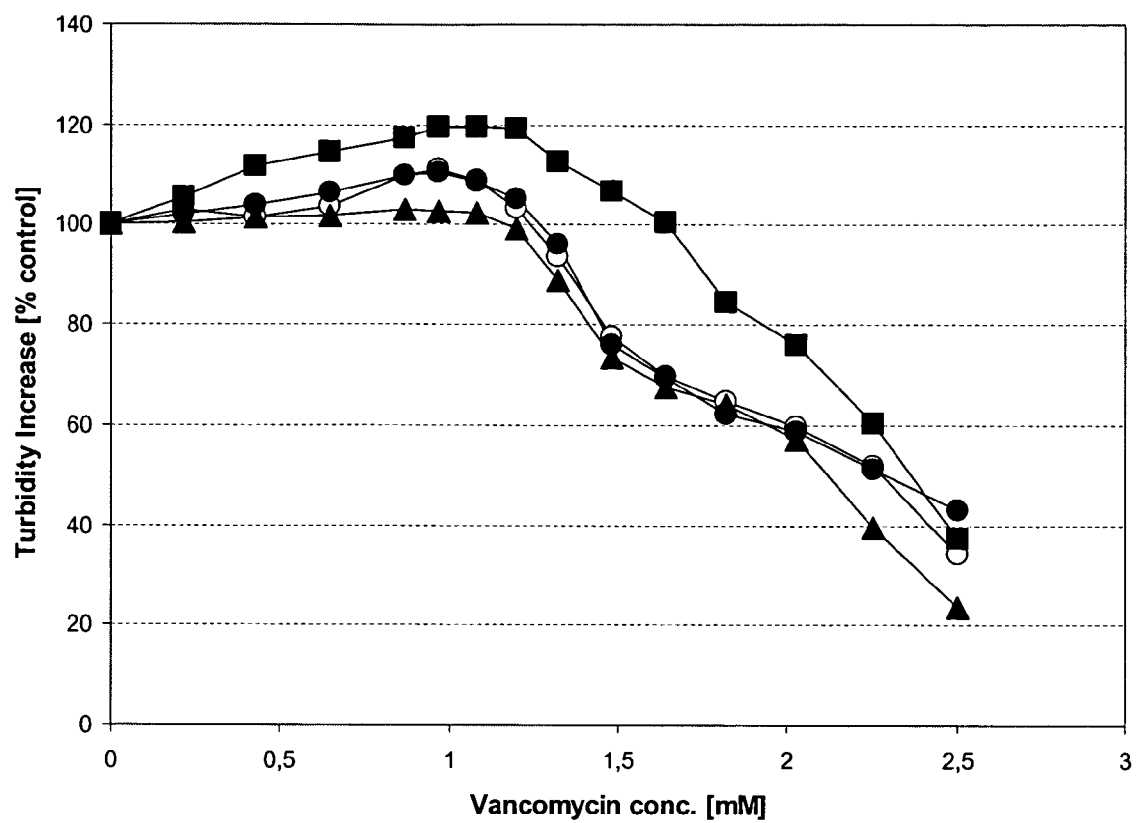
Fig. 19a: Is the reaction between vancomycin and fibrinogen quenchable by antioxidants ?

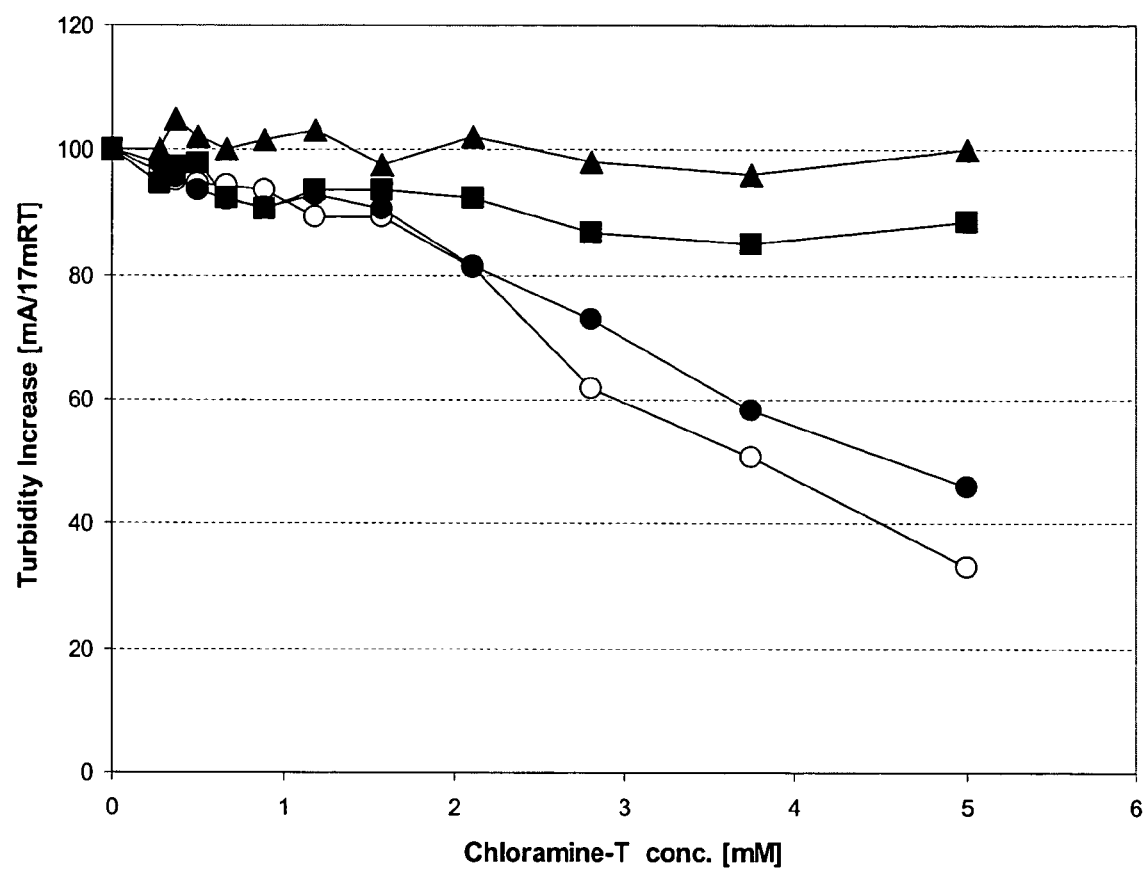
Fig. 19b: Quenching of the reaction between fibrinogen and chloramine-T

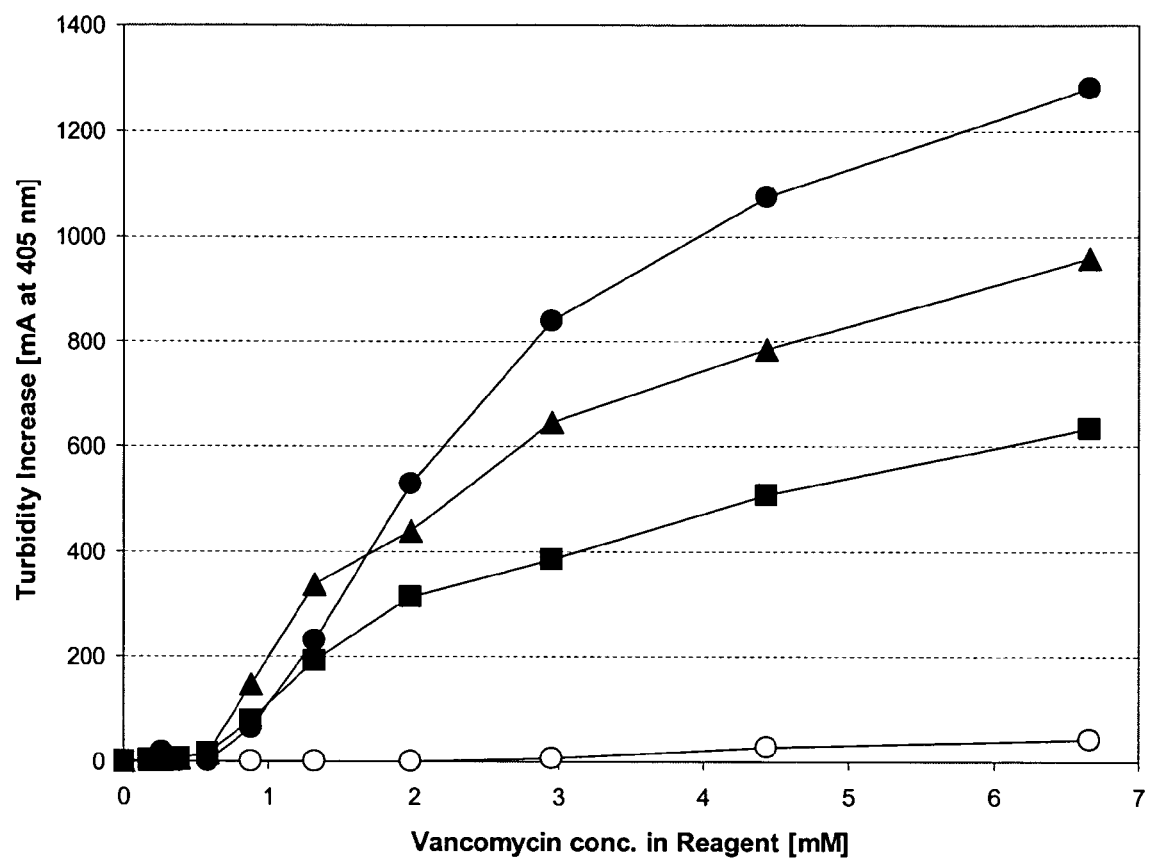
Fig. 20a: Turbidity increase in dependence of vancomycin-concentration

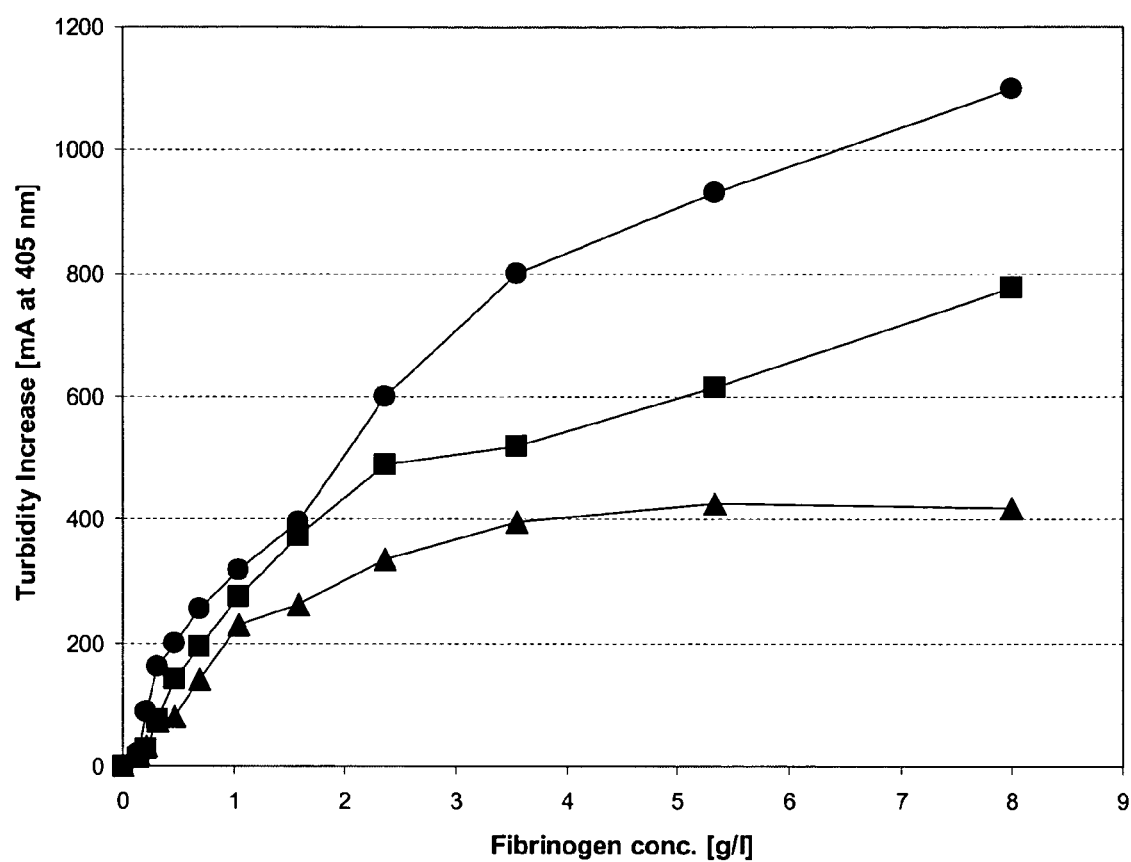
Fig. 20b: Turbidity increase in dependence of fibrinogen concentration

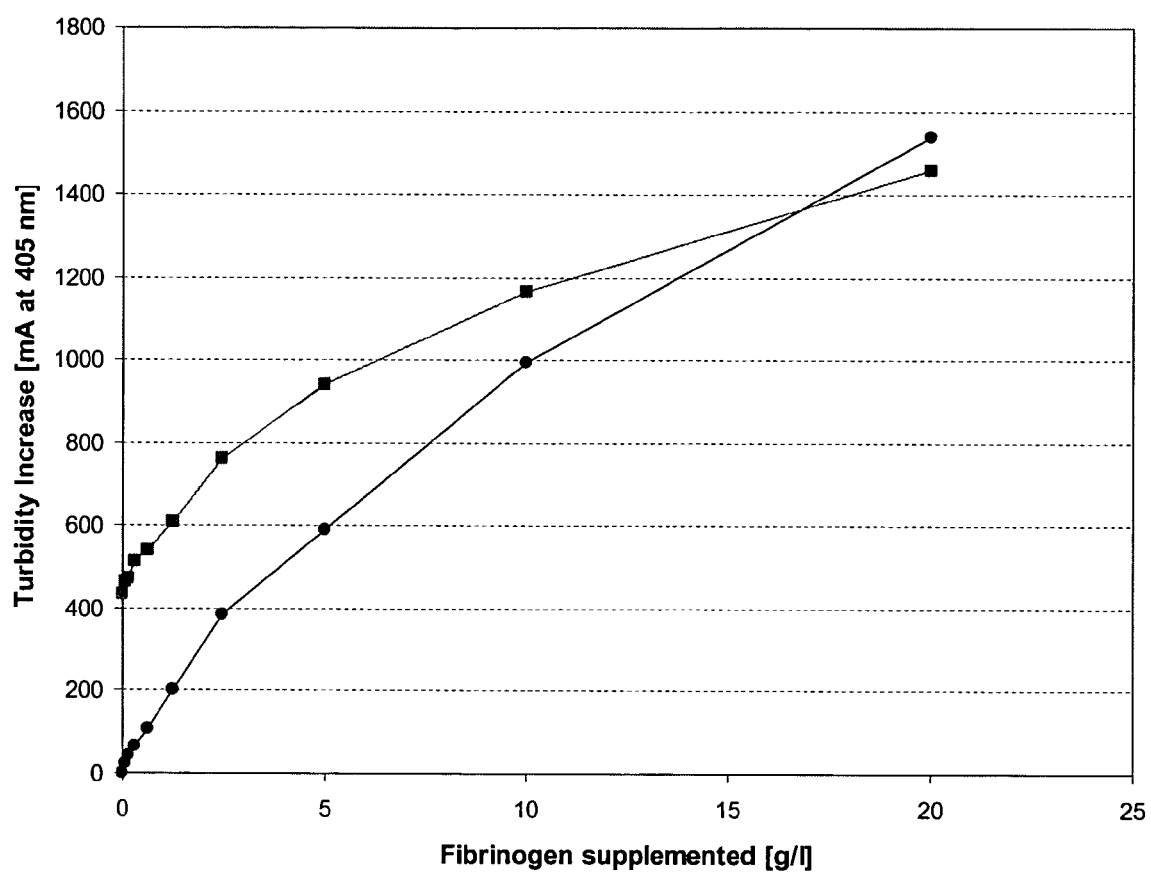
Fig. 21: FIATA calibration with purified fibrinogen

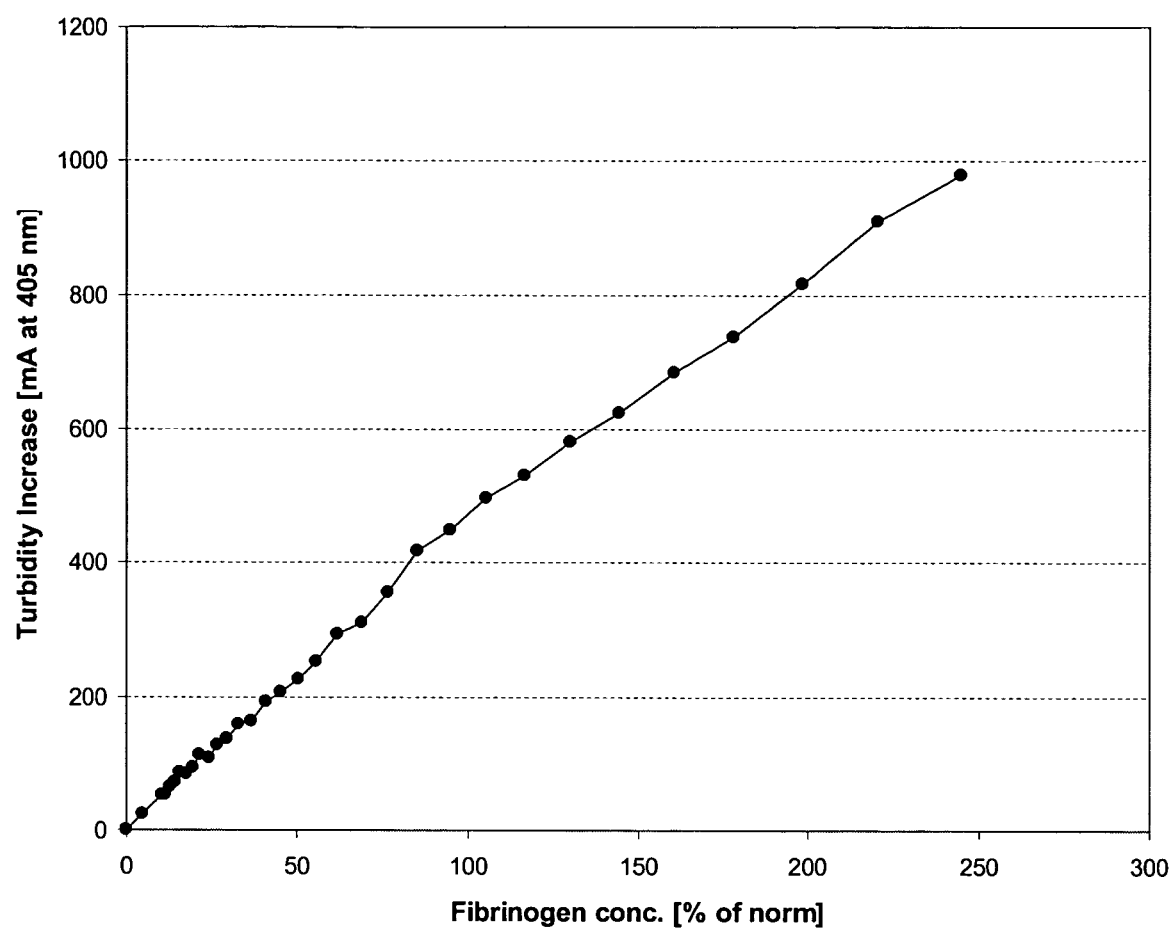
Fig.22a: FIATA linearity

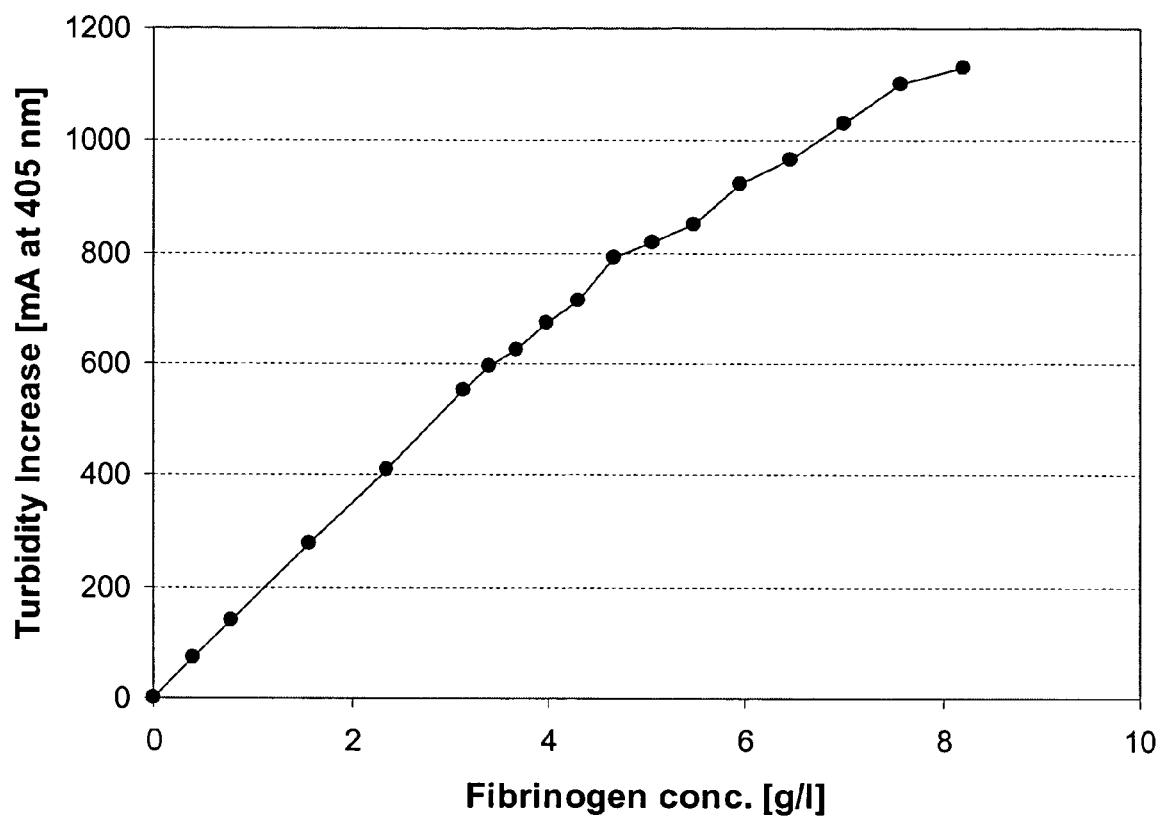
Fig. 22b: FIATA linearity; dilutions with serum

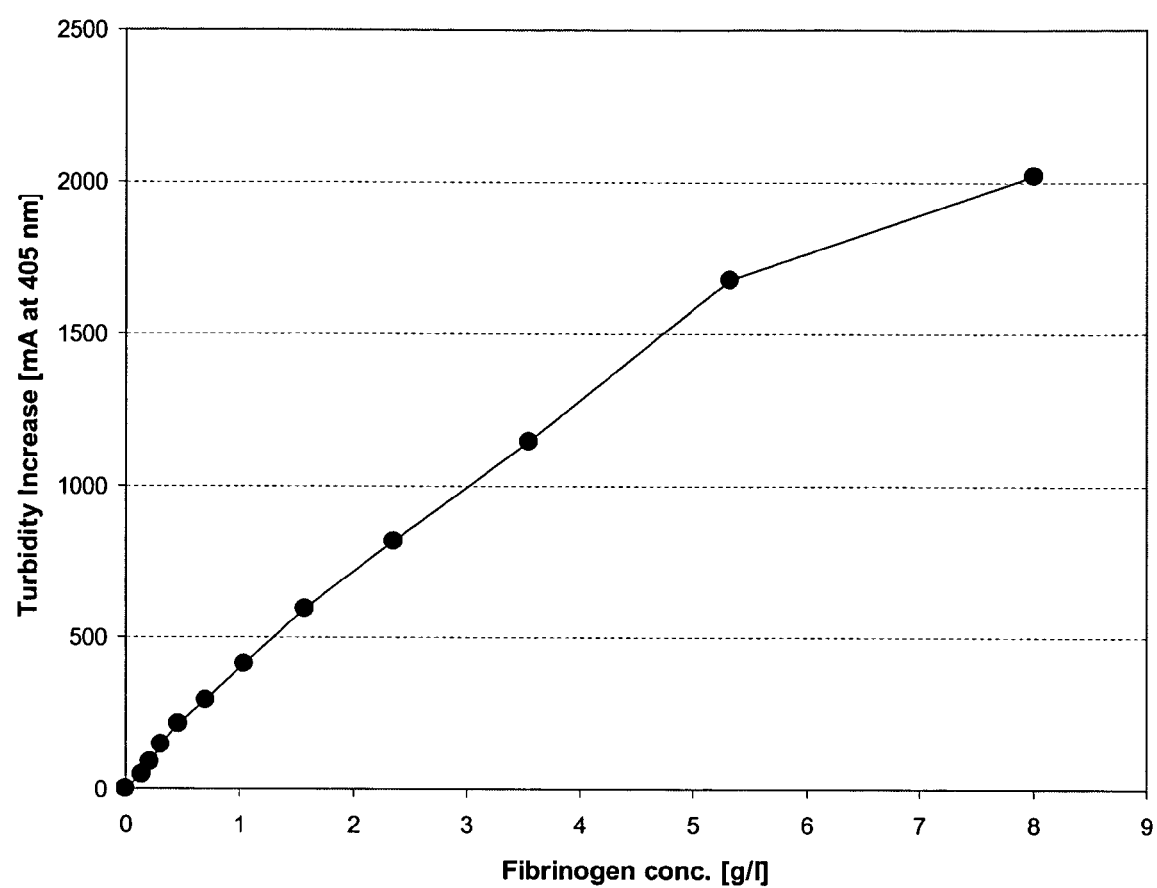
Fig. 22c: FIATA linearity

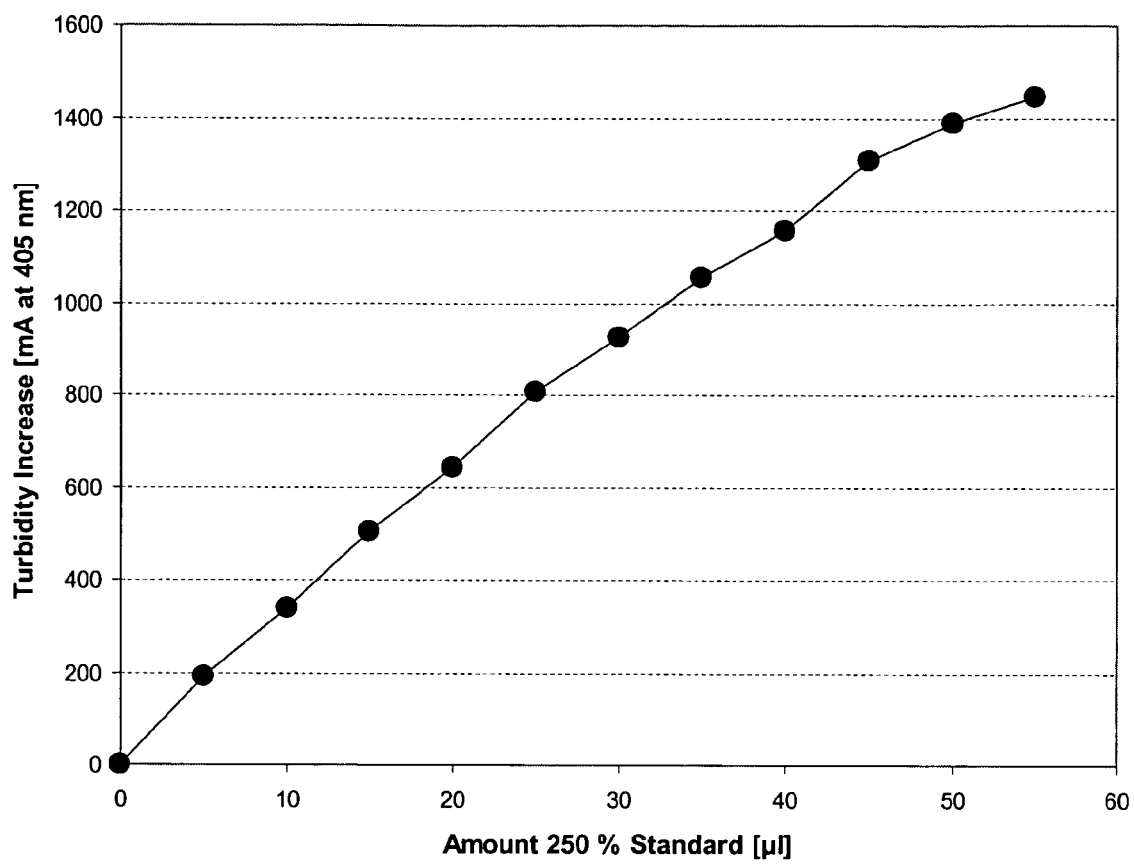
Fig. 22d: FIATA linearity

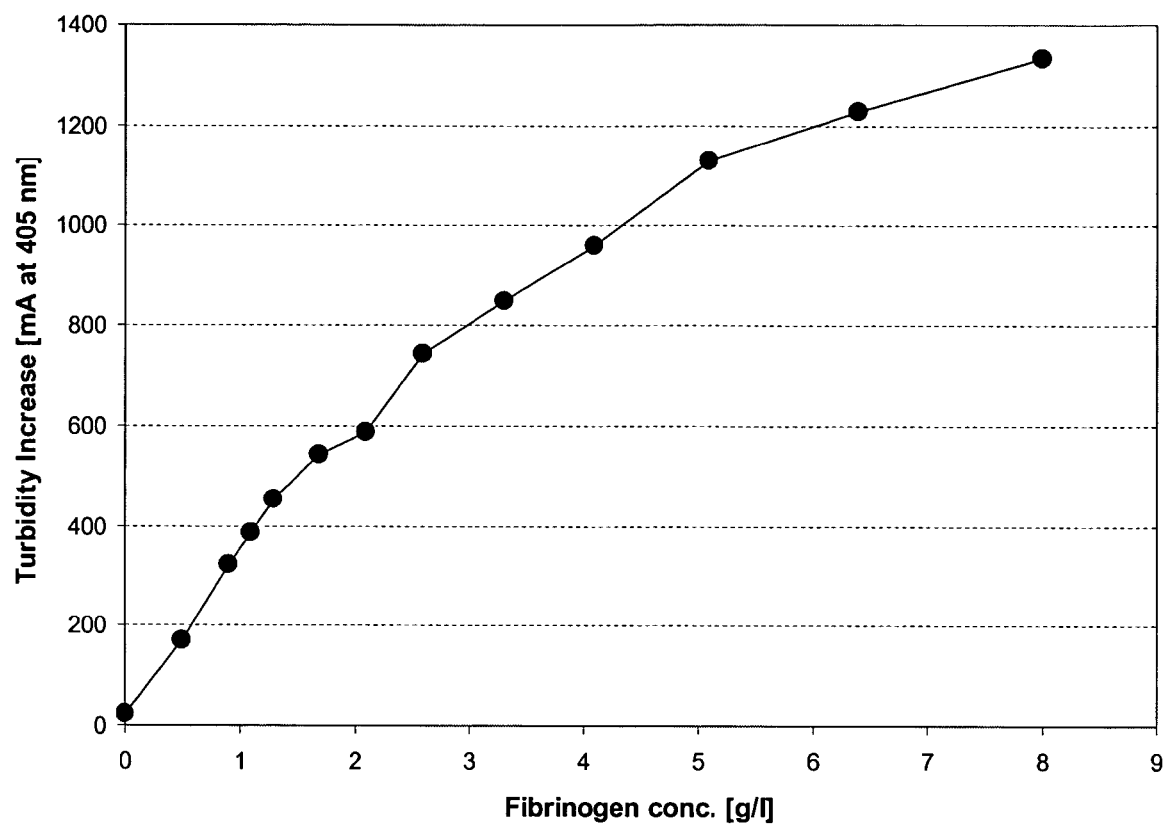
Fig. 22e: FIATA linearity

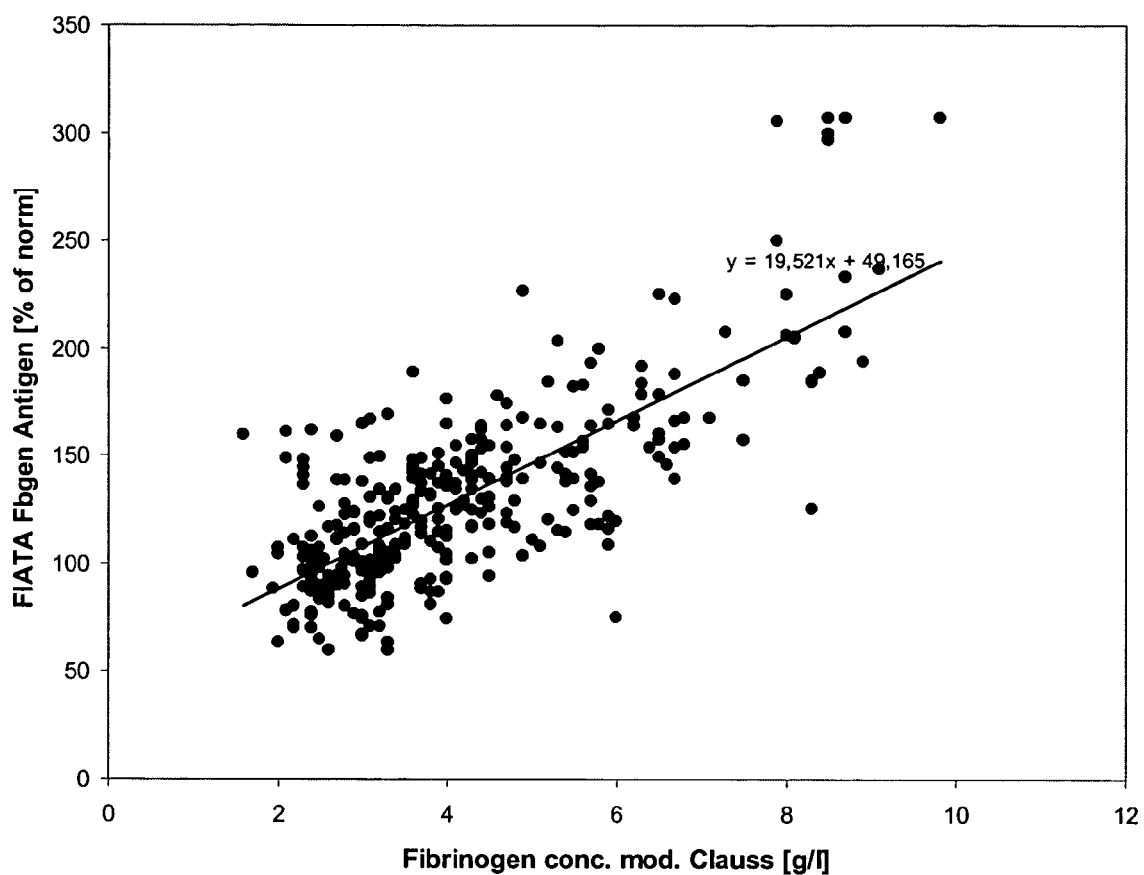
Fig. 23a: FIATA correlation with mod. Clauss-method

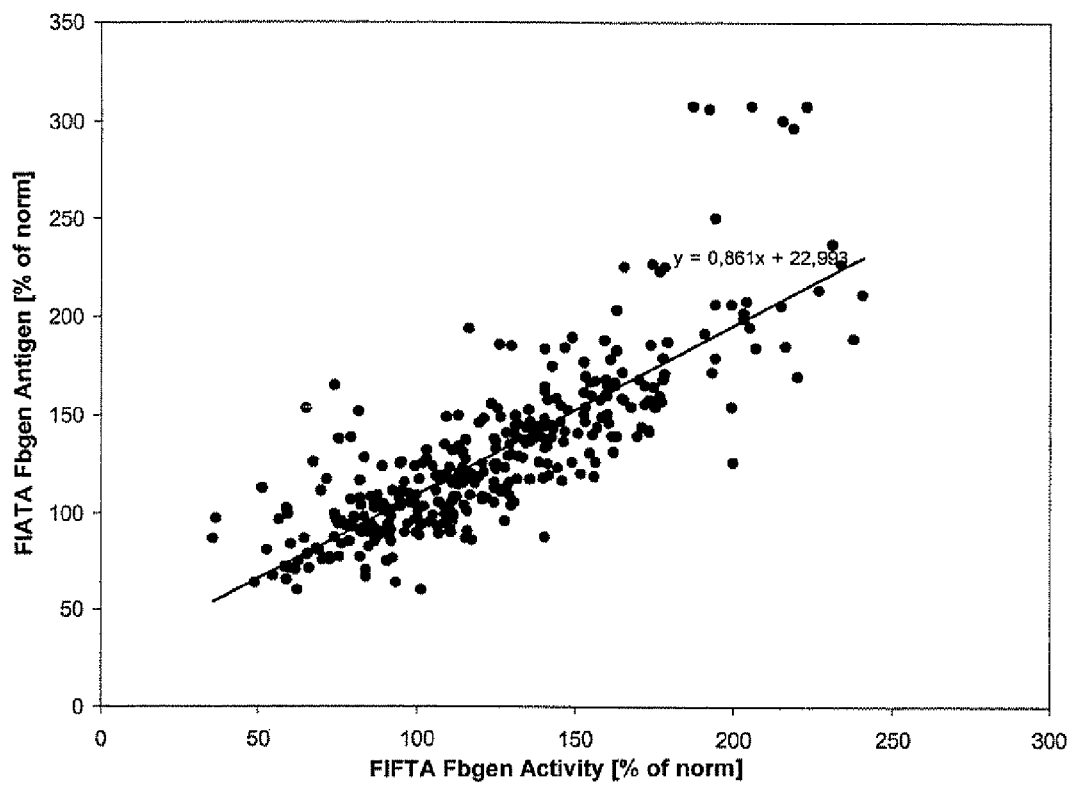
Fig. 23b: FIATA correlation with FIFTA

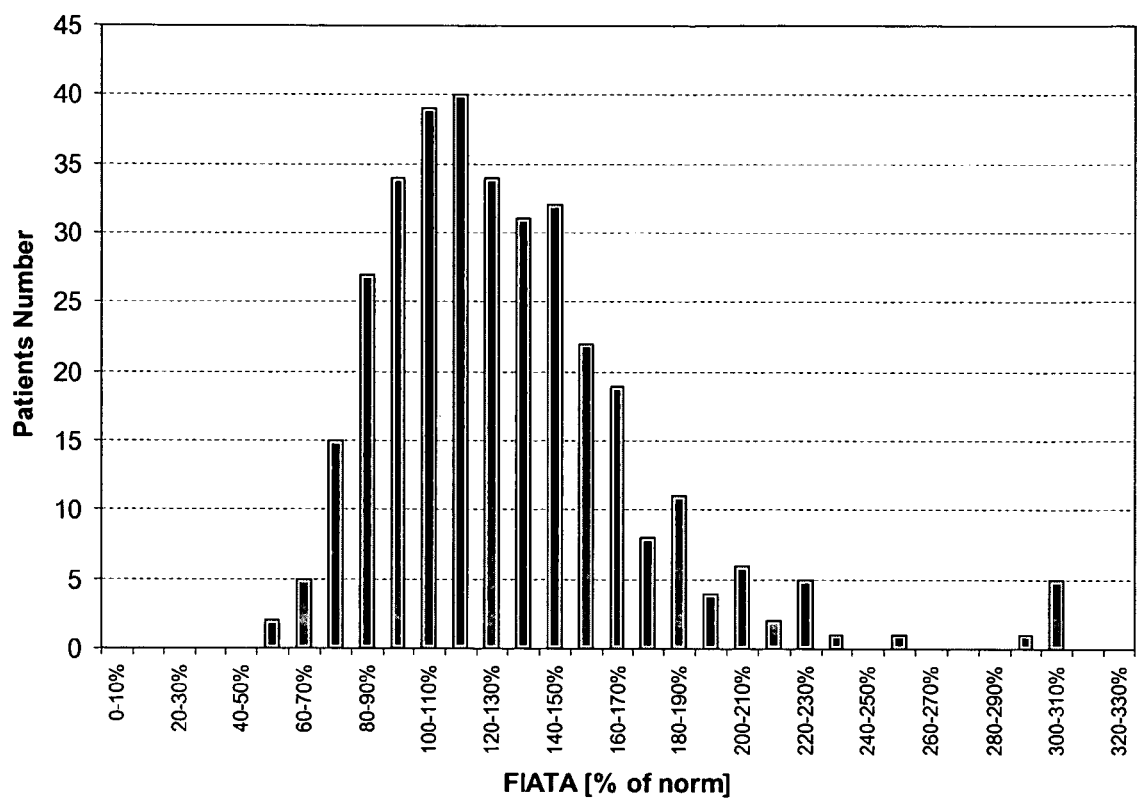
Fig. 23c: Gaussian Distribution of FIATA among patients

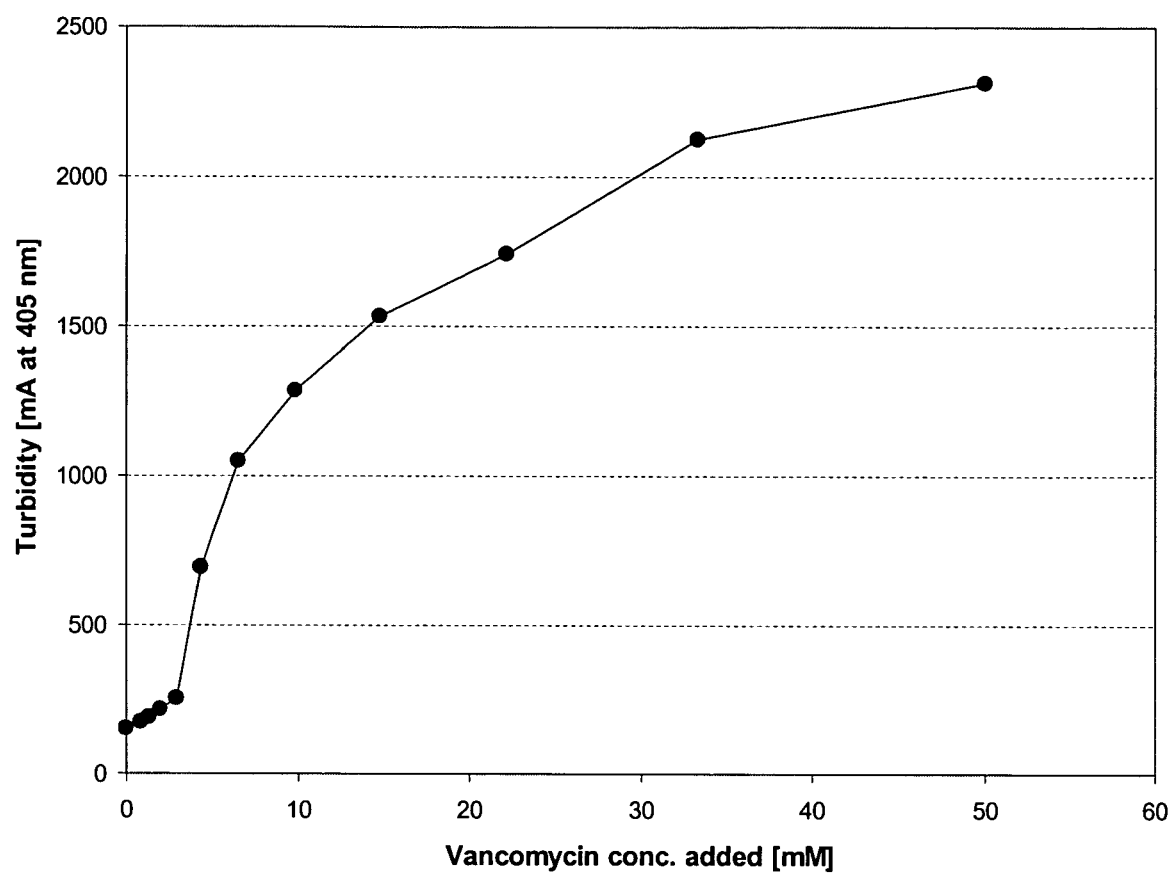
Fig. 24a: Precipitation of plasmatic fibrinogen by vancomycin

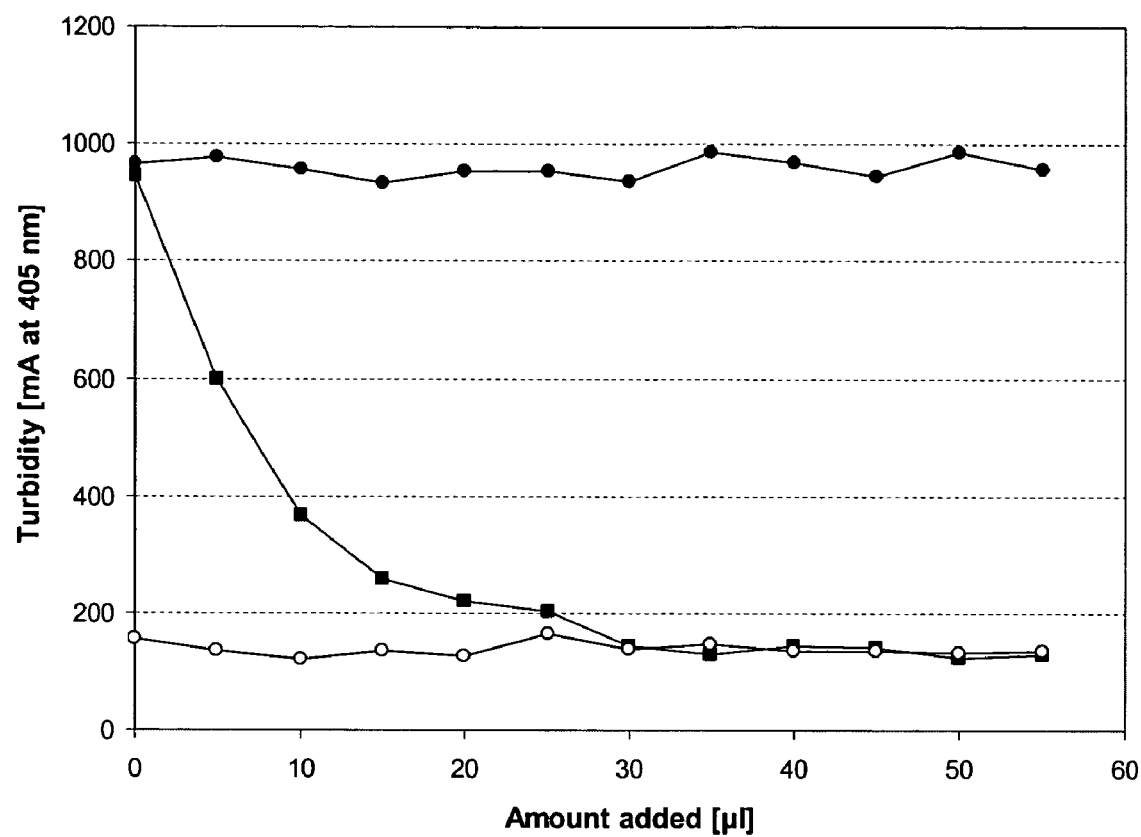
Fig. 24b: Reversal of vancomycin-induced fibrinogen precipitation by NaHCO3

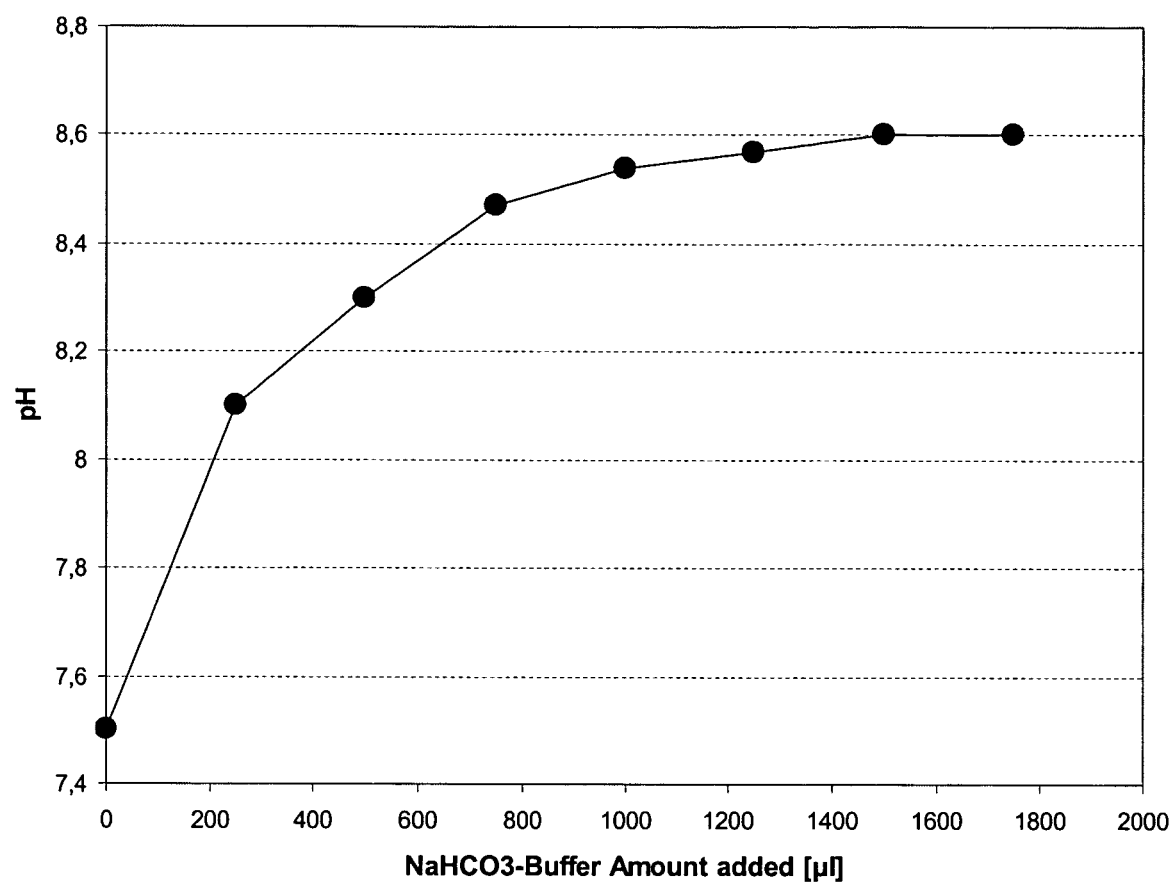
Fig. 24c: Determination of assay pH

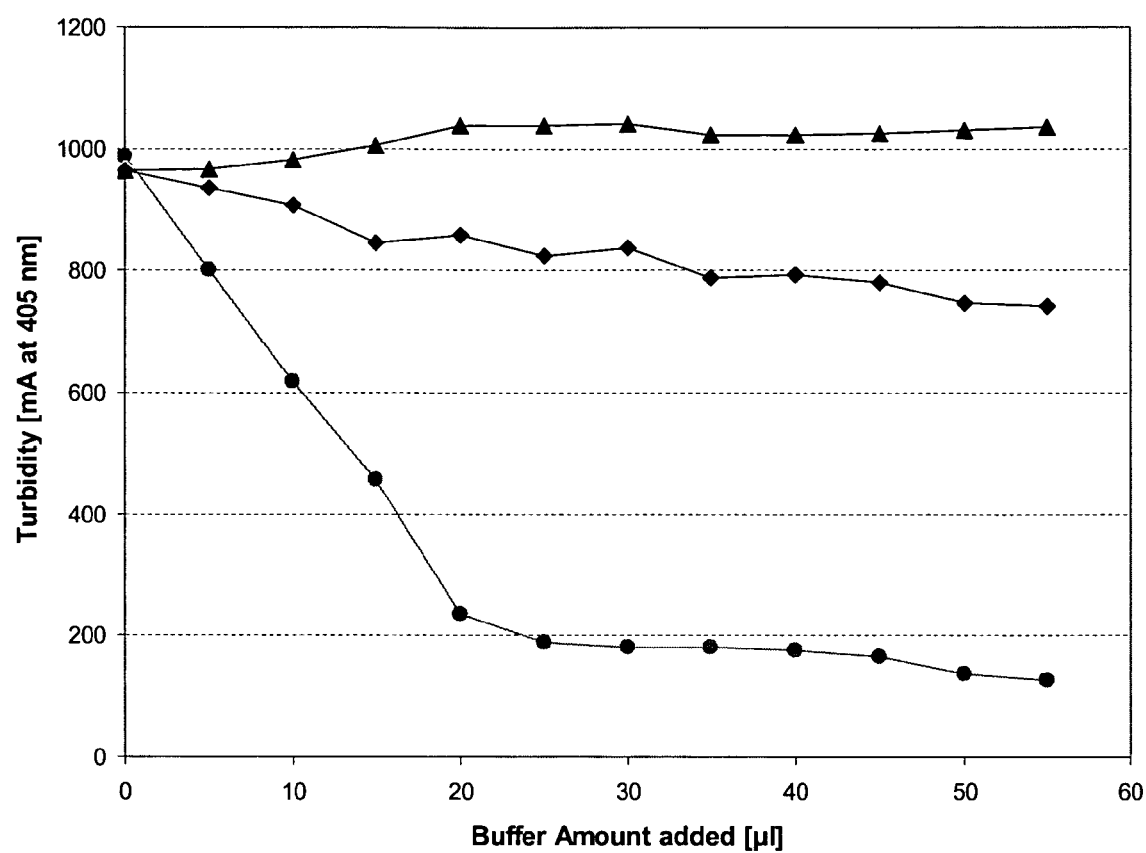
Fig. 24d: Reversal of vancomycin-induced fibrinogen precipitation by arginine Fig. 25: Electrophoresis of plasma that had been incubated with vancomycin
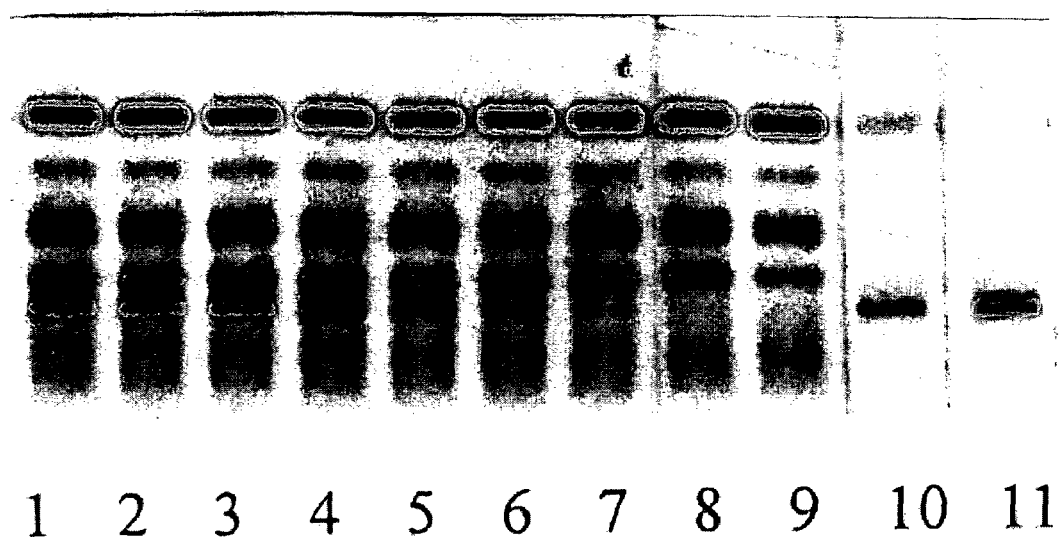

Fig. 25a: 0 mM vanco in P-Pool
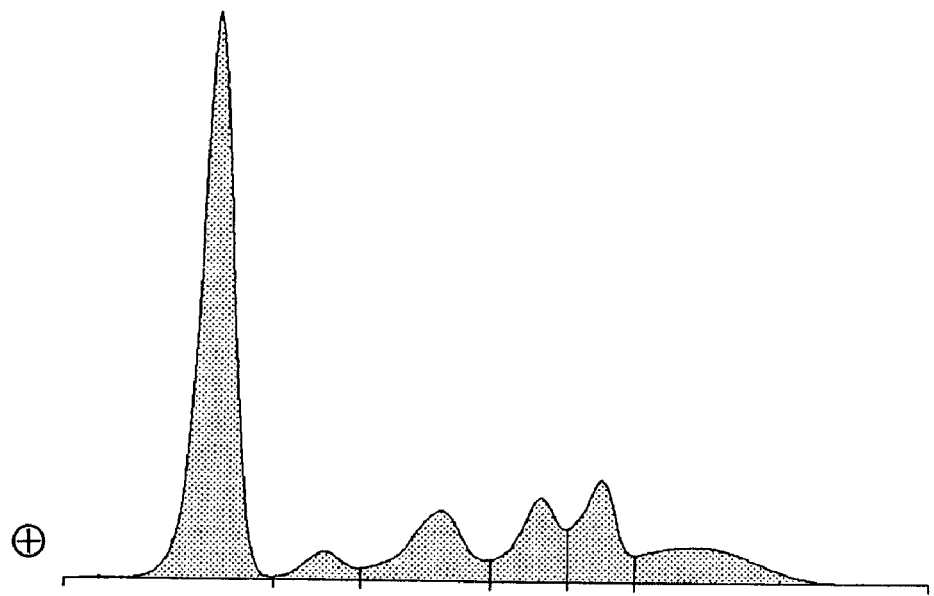
Fig. 25b: 0,29 mM vanco in P-Pool
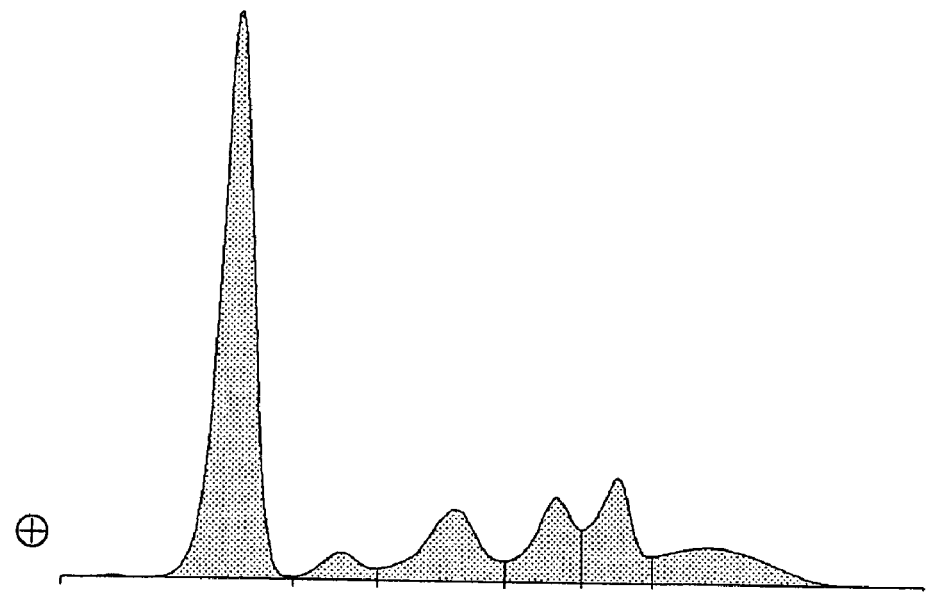

Fig. 25c: 0,44 mM vanco in P-Pool
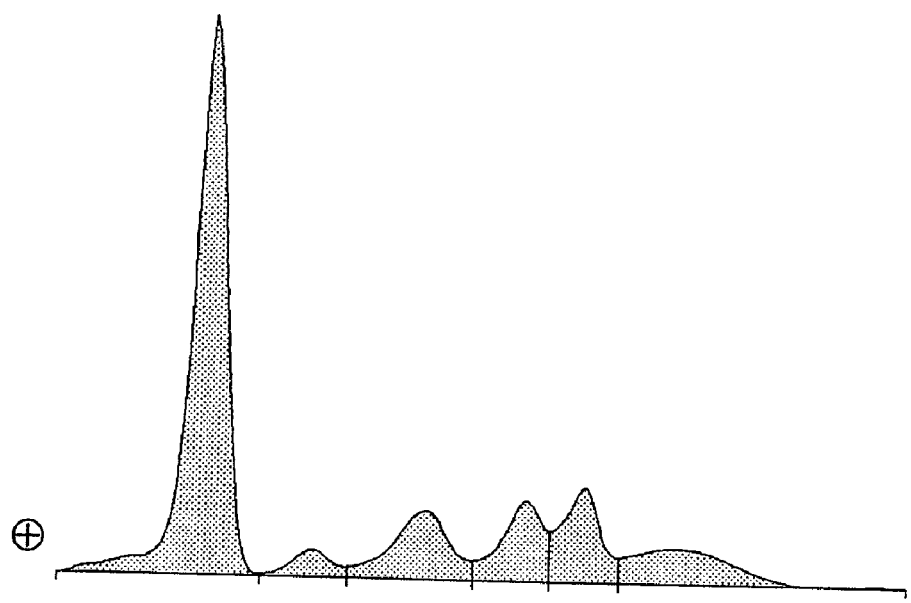
Fig. 25d: 0,66 mM vanco in P-Pool
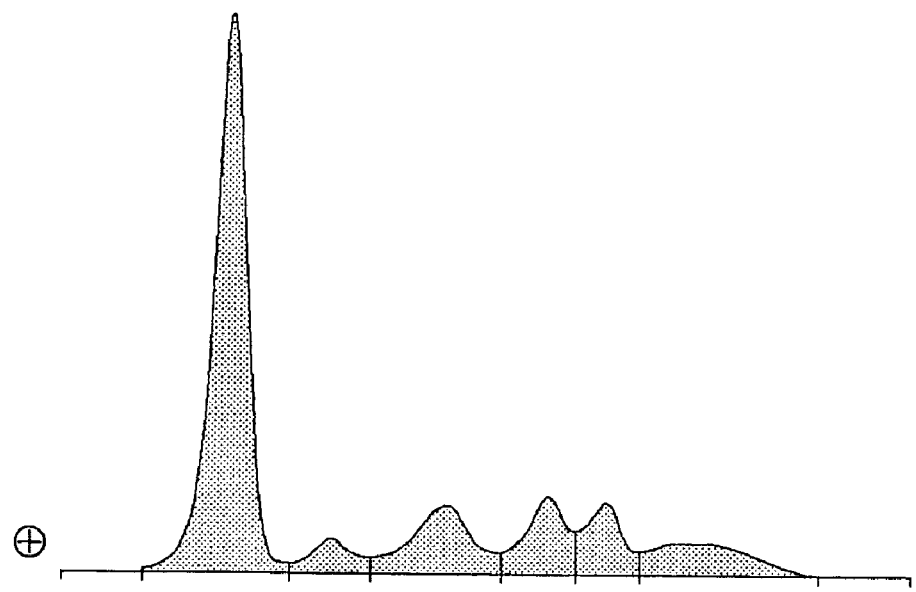

Fig 25e: 0,99 mM vanco in P-Pool
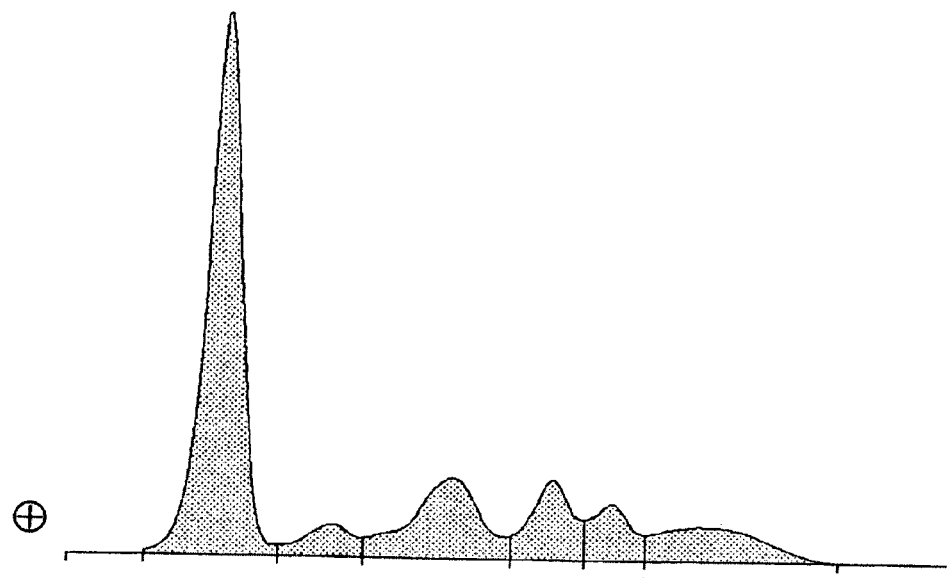
Fig. 25f: 1,48 mM vanco in P-Pool
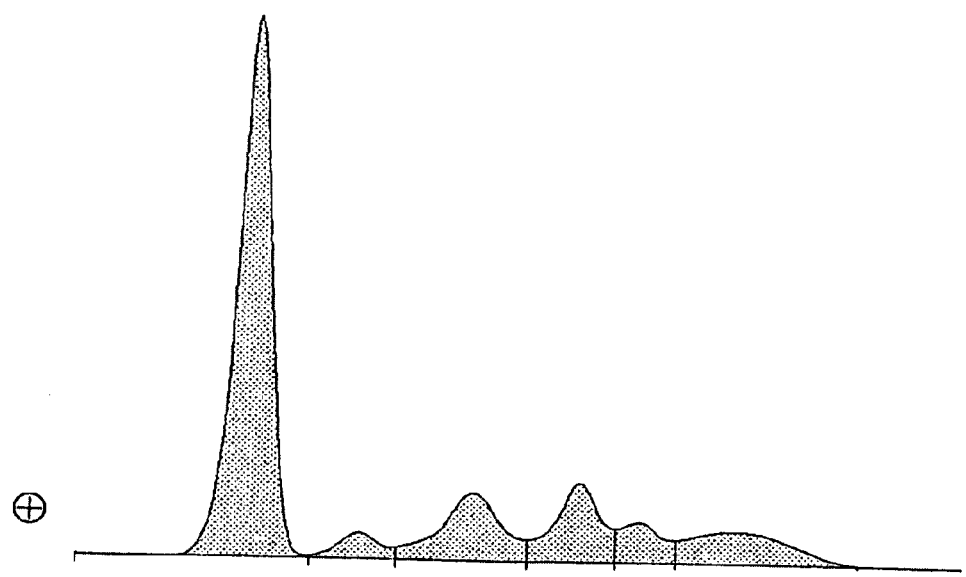

Fig. 25g: 2,22 mM vanco in P-Pool
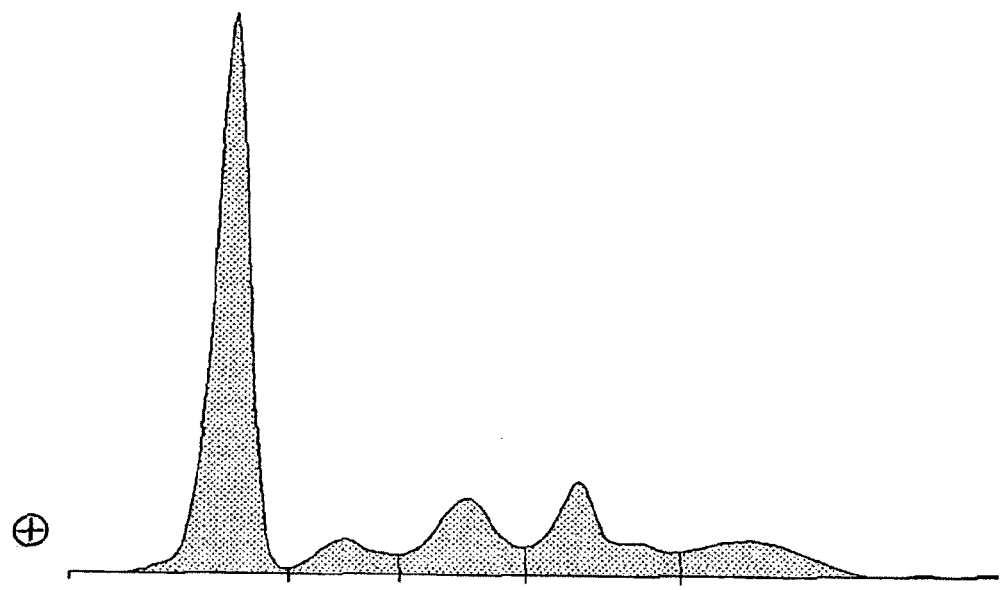
Fig. 25h: 5 mM vanco in P-Pool
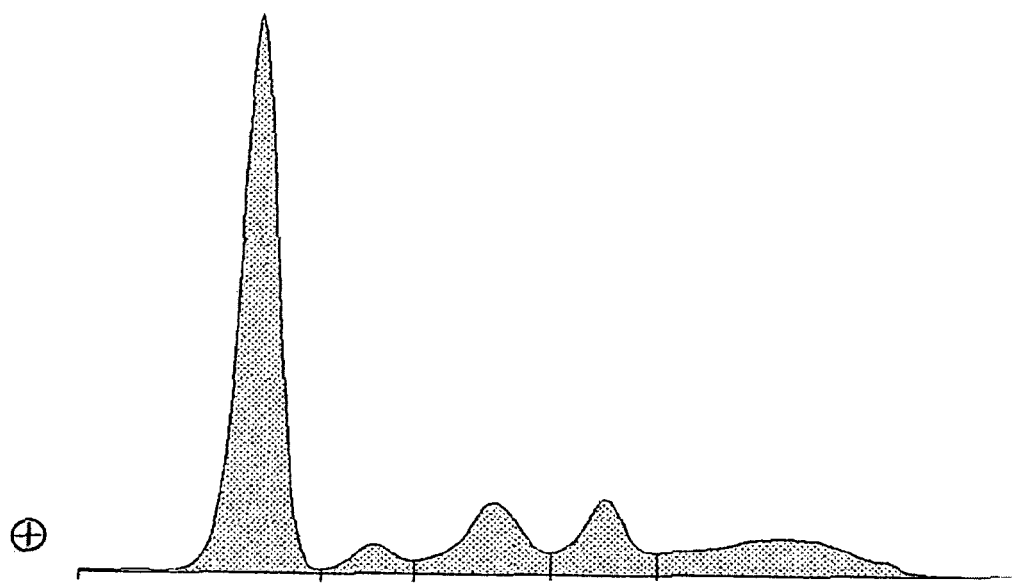

Fig. 25i: 10 mM vanco in P-Pool
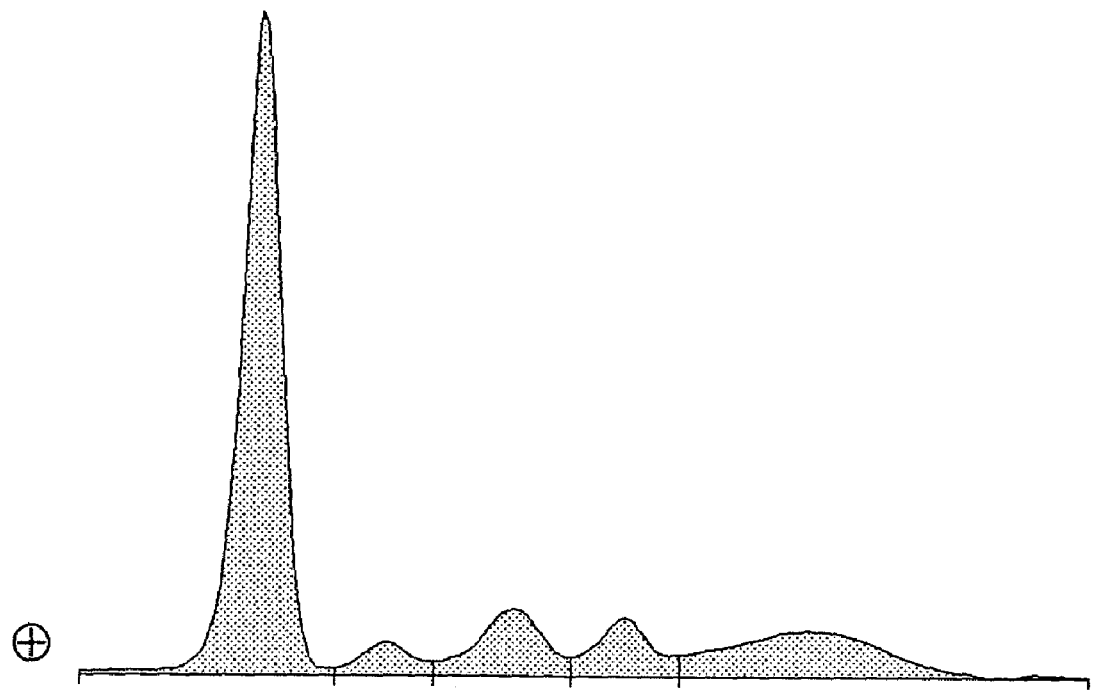

Fig. 25j: Resolubilized unwashed precipitate
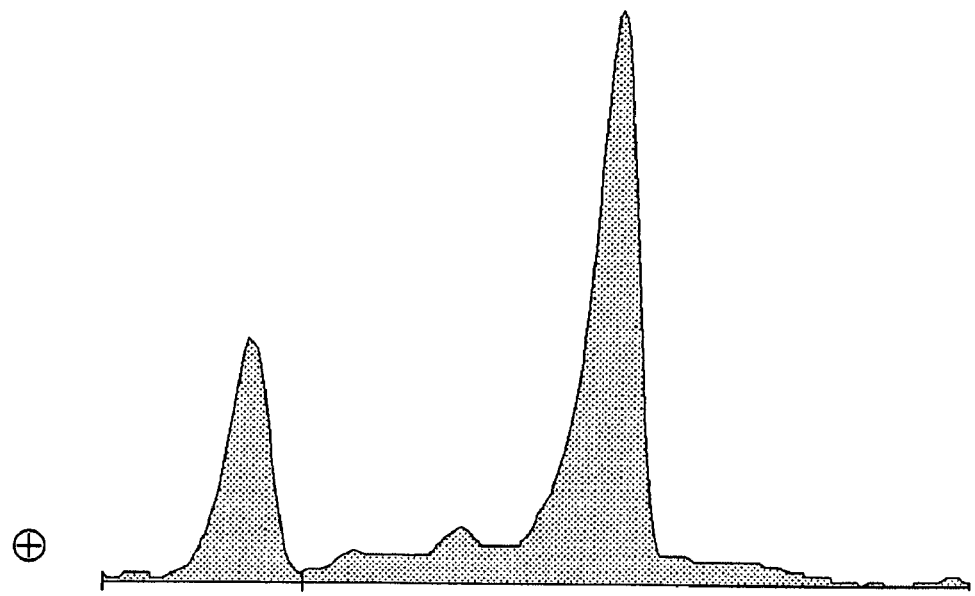
Fig 25k: 3x washed precipitate of Fig. 25j
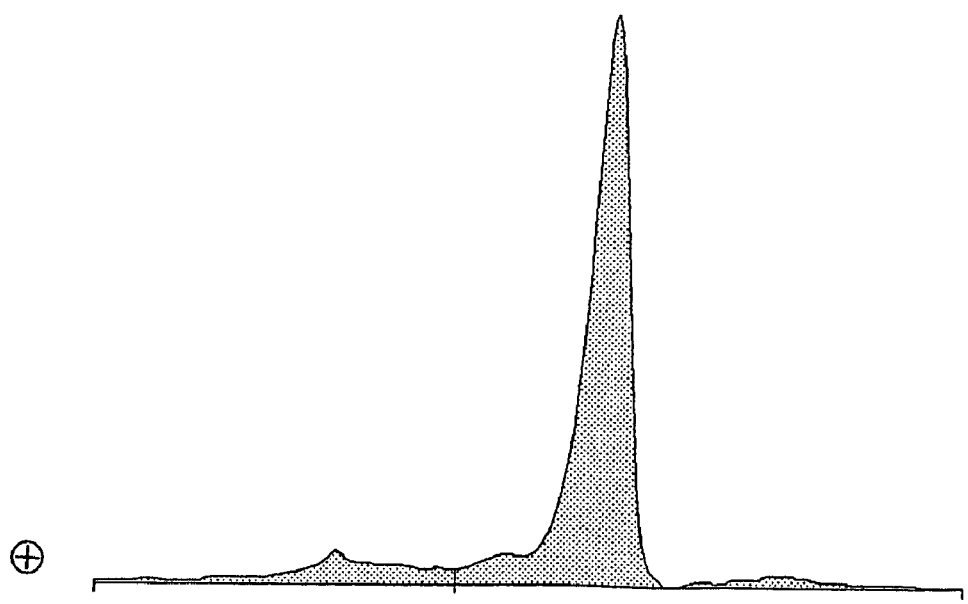

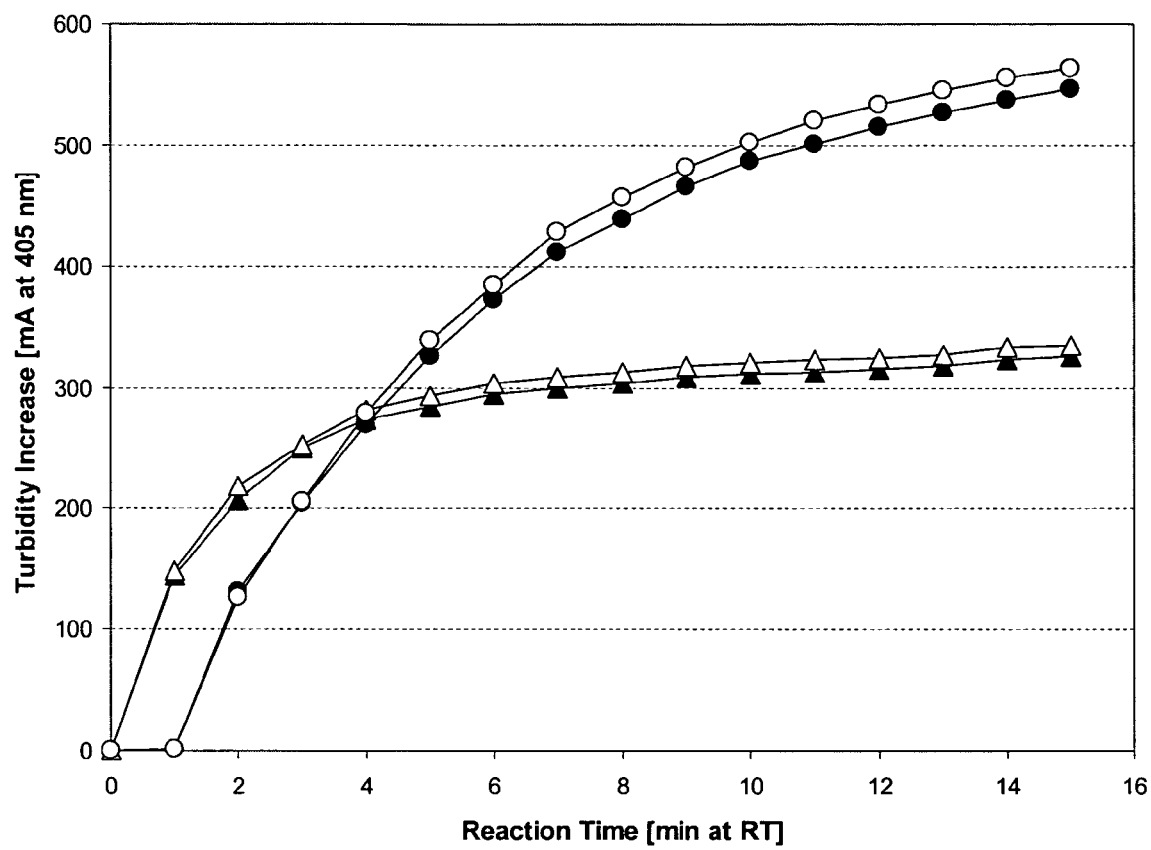
Fig. 26a: Fibrinogen reactivity in vancomycin-precipitated plasma

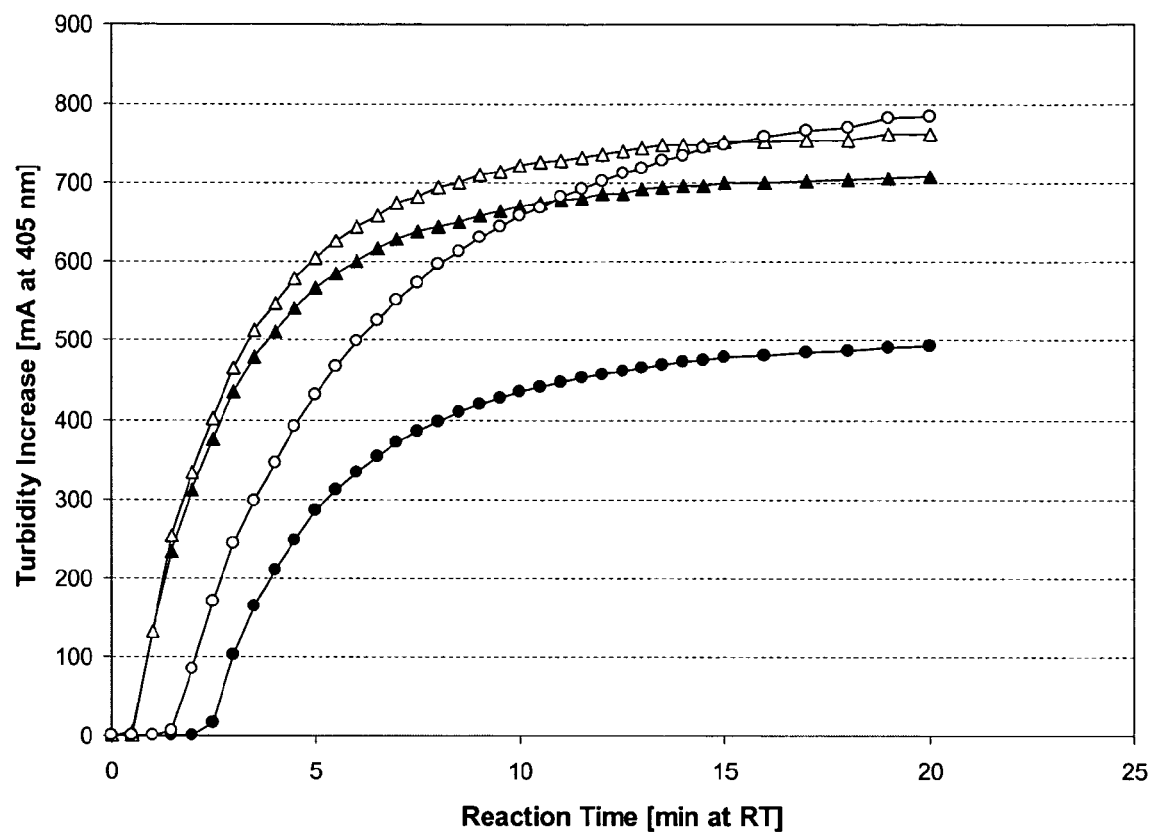
Fig. 26b: Fibrinogen reactivity in vancomycin- precipitated plasma

Fig. 26c: Fibrinogen reactivity in vancomycin-precipitated plasma
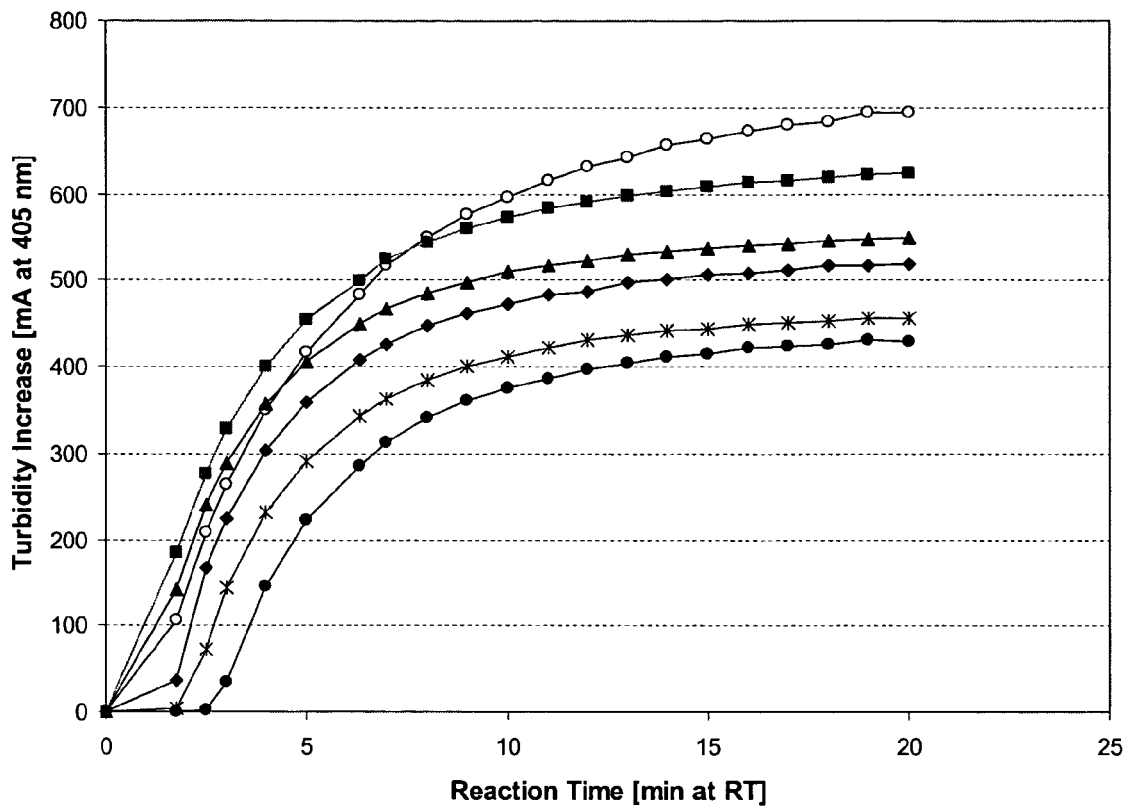
Fig. 27a: Stimulation of t-PA by vancomycin-precipitated fibrinogen
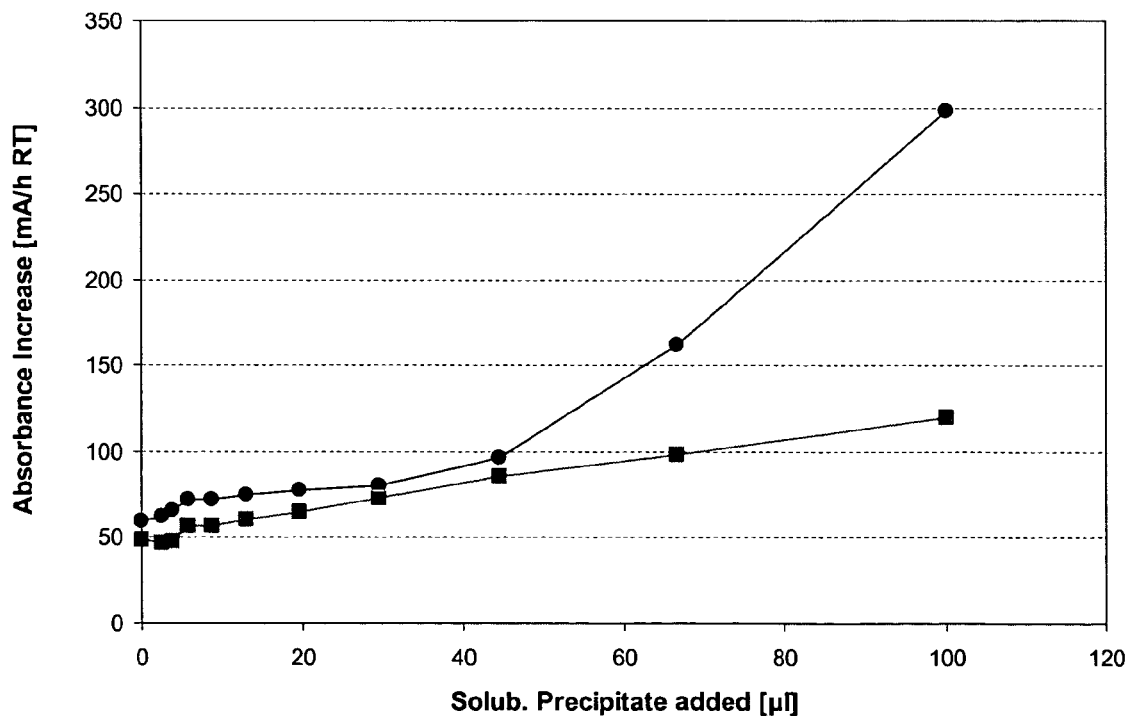

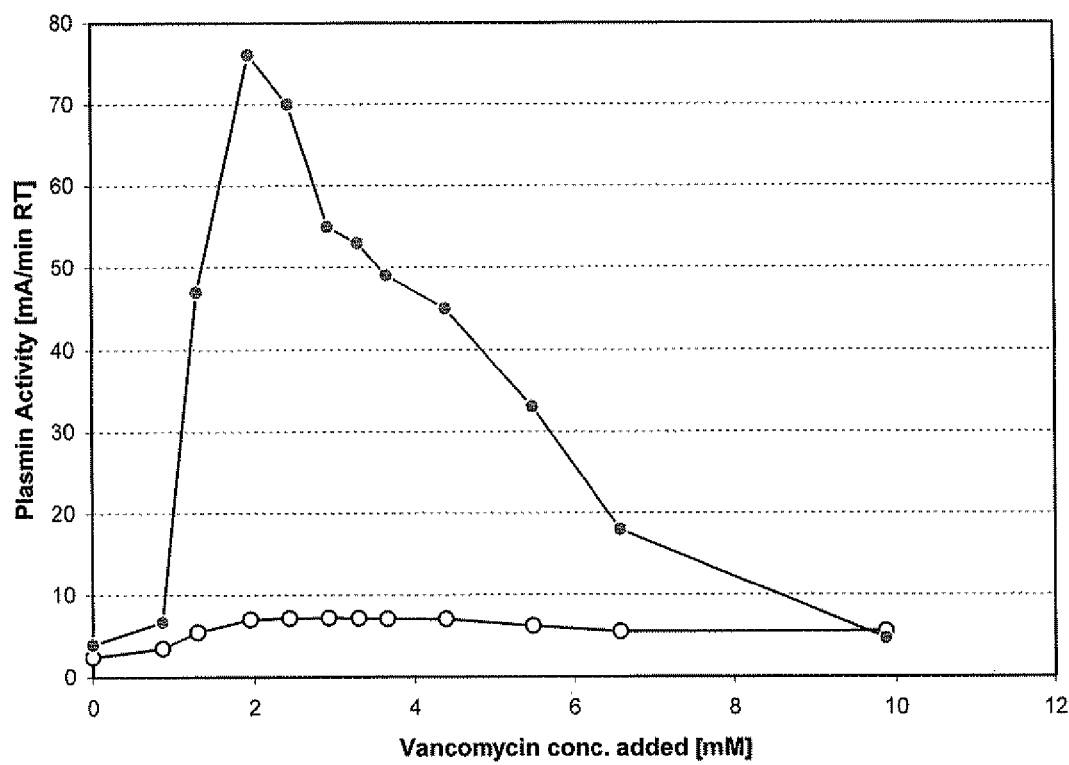
Fig. 27b: Stimulation of t-PA by vancomycin-precipitated plasma

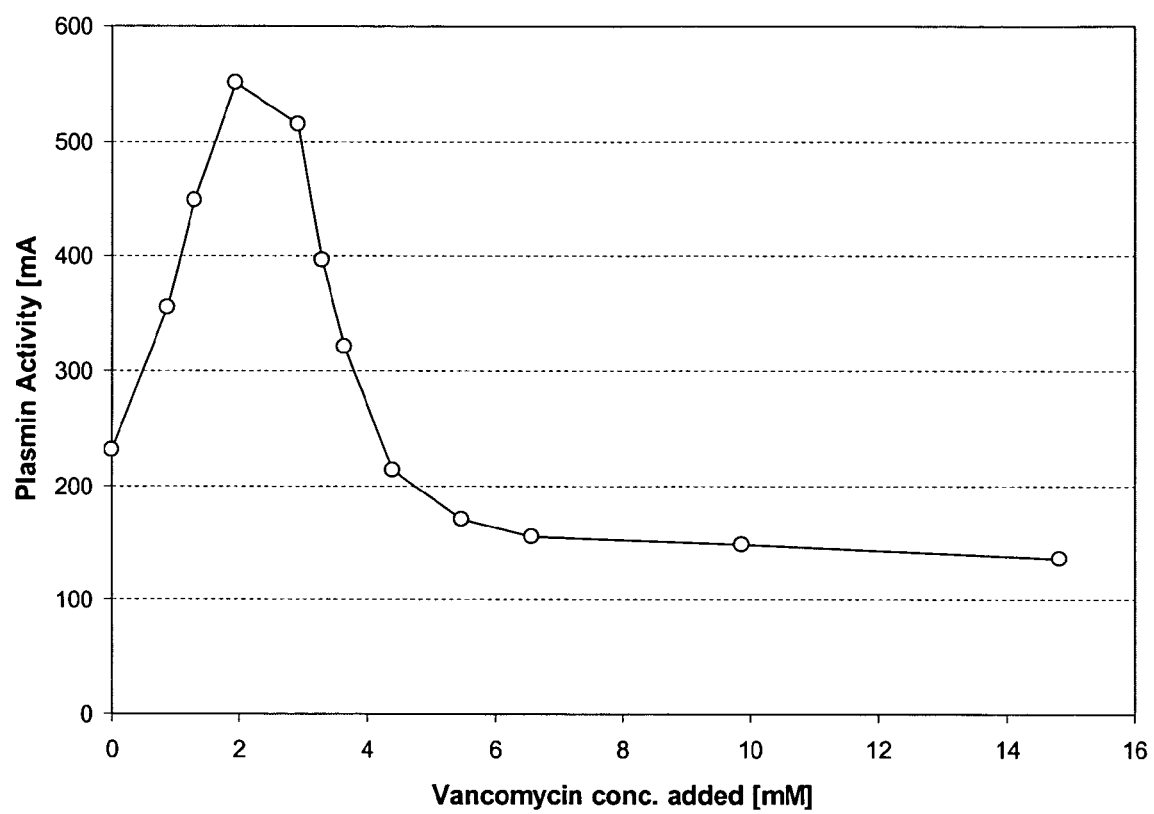
Fig. 27c: Stimulation of t-PA by vancomycin-precipitated plasma

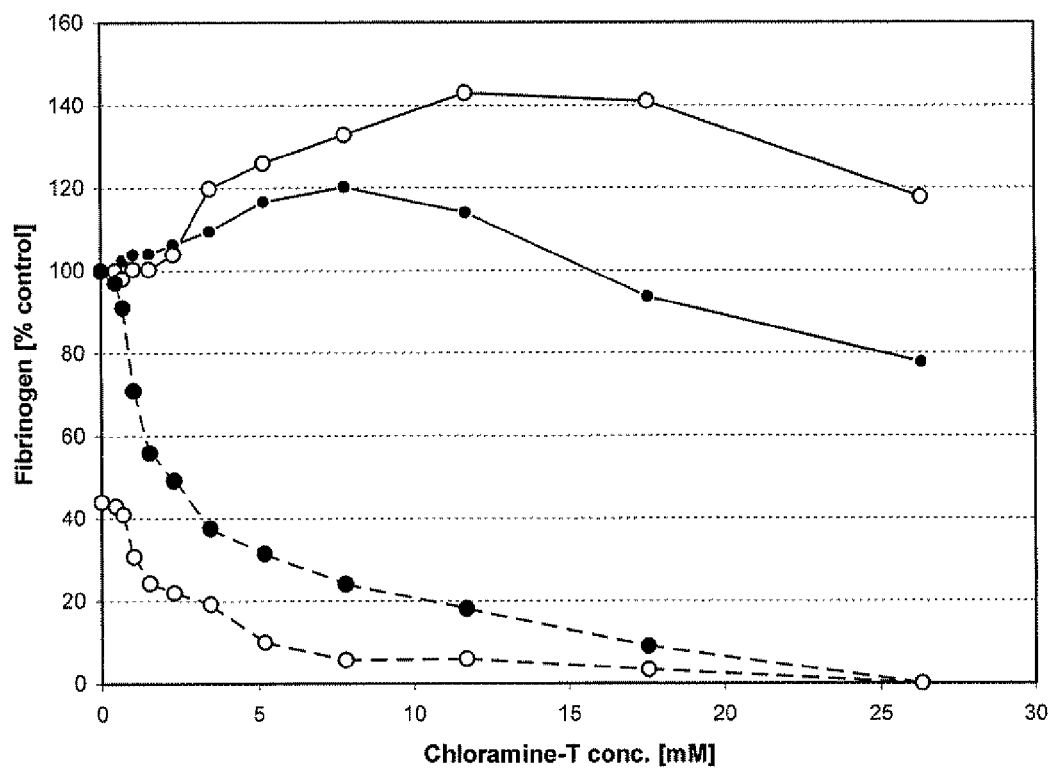
Fig. 28: Vancomycin reactivity with oxidized plasma

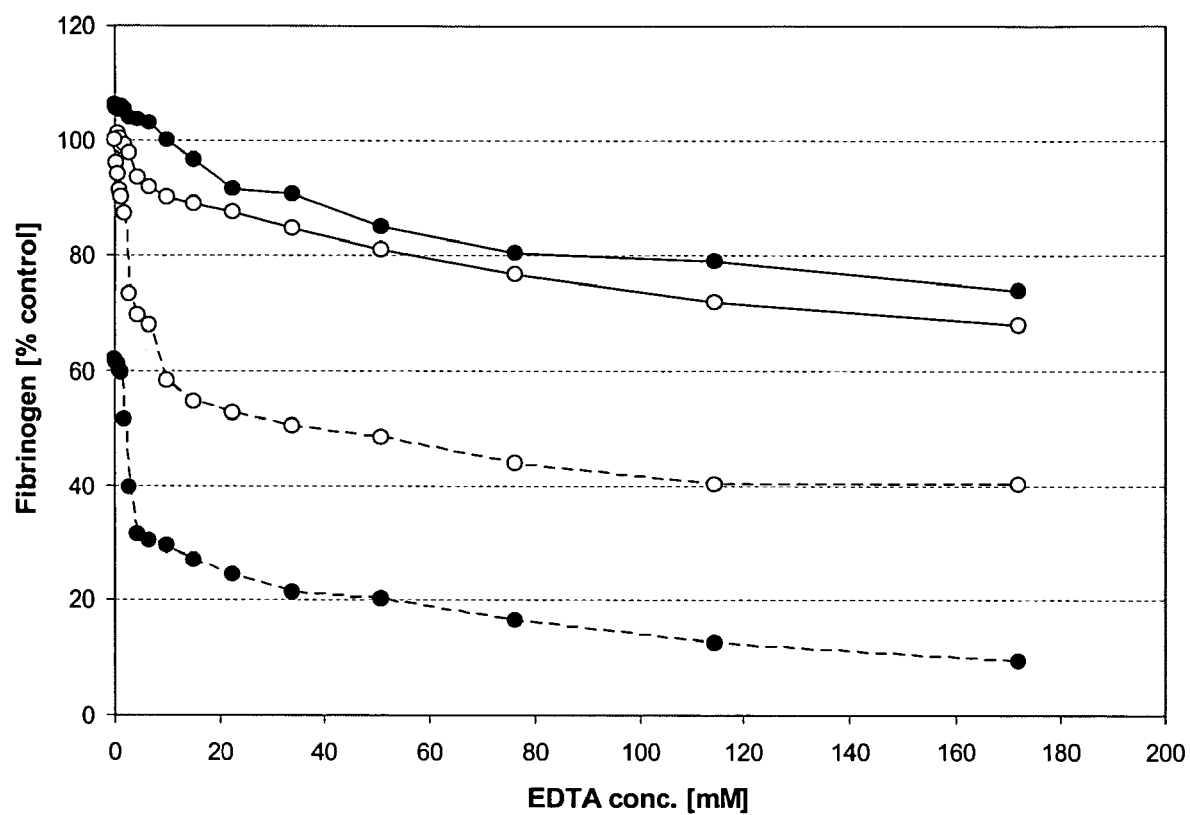
Fig. 29: Vancomycin reactivity in EDTA plasma

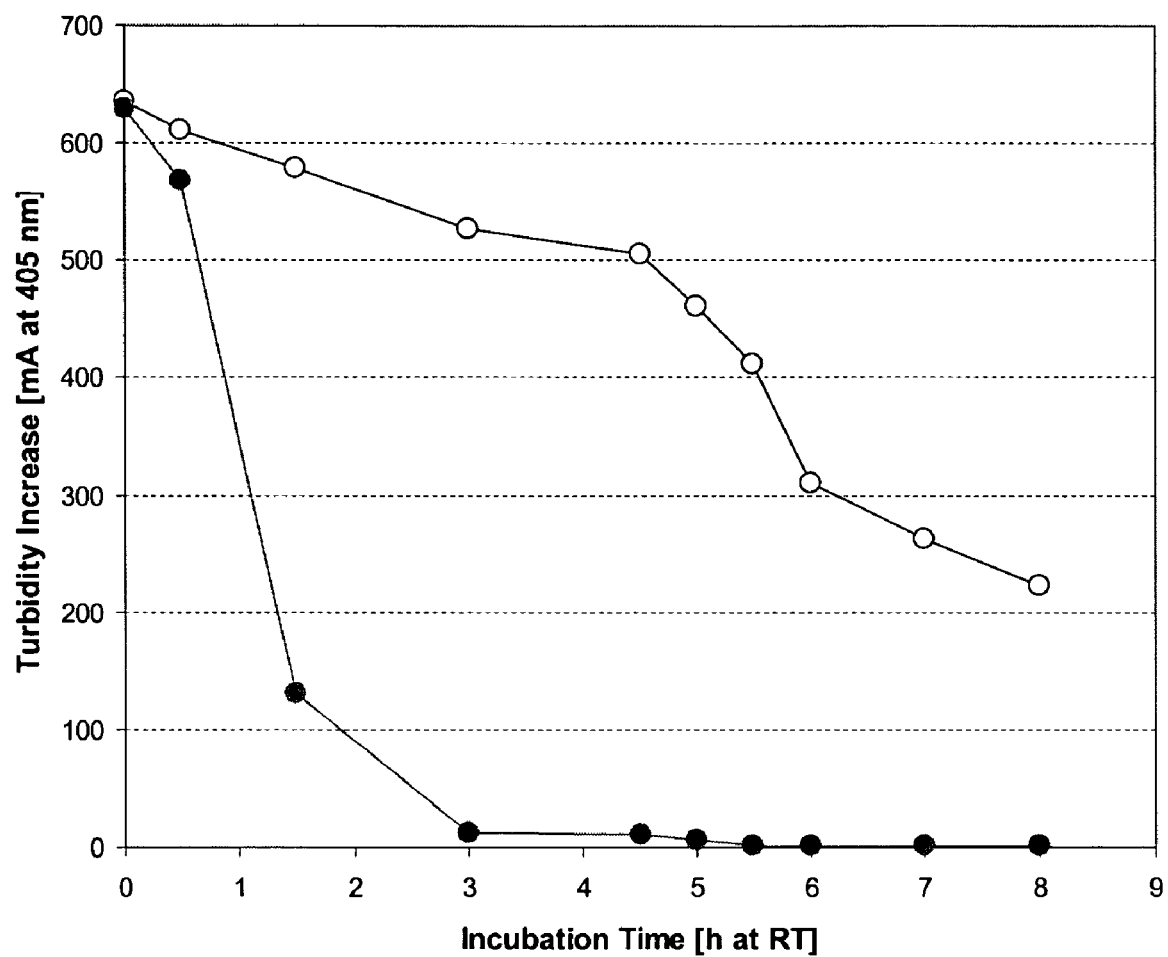
Fig. 30: Vancomycin-reactivity with t-PA incubated plasma

DETECTION PROCEDURES FOR FIBRINOGEN AND/OR FIBRINOGEN DERIVATIVES

The present invention concerns detection procedures for fibrinogen and/or fibrinogen derivatives that are based on a measurement of turbidity.

The determination of the activity and/or concentration of fibrinogen and/or of fibrinogen-derivatives in blood and/or plasma of blood is of high clinical importance. According to the invention fibrinogen-derivatives are derivatives of fibrinogen as they are generated especially by the action of enzymes, particularly thrombin and/or plasmin, or by oxidation of fibrinogen; e.g. fibrin and/or fibrin-or fibrinogen-split products or oxidized fibrinogen are derivatives of fibrinogen.

The in the state of the art known tests for determination of fibrinogen and/or fibrinogen derivatives are quite complex and/or the test conditions often are not physiological, e.g. by addition of high concentrations of thrombin (EP-B-0137269, DE-A-4133946, U.S. Pat. No. 6,448,024), resulting into unreliable test results of fibrinogen-activity and/or concentration of fibrinogen derivatives, as they occur in the blood of the patient.

As nearest state of the art is considered the functional determination of fibrinogen according to the modified Clauss-method (DE-A-4133946) and the so-called PT-Fg-method (from prothrombin time derived fibrinogen; e.g. Thromborel-S®, DadeBehring, Marburg, Germany).

In the method according to Clauss the plasma sample is 10fold diluted, thrombin is added, and the time point of clotting onset (=clotting time) is measured. This clotting time correlates indirectly with the concentration of active fibrinogen in the sample. In a modified Clauss-approach according to DE-A-4133946 to 100 µl sample 200 µl 50 IU/ml bovine thrombin, 0.15 g/l polymerization inhibitor Gly-Pro-Arg-Pro-Ala-amide, 1.5 g/l $CaCl_2$, 15 µg/ml Polybrene®, 0.8 g/l Polyethylenglycol 6000, 6.4 g/l NaCl, 50 mM Tris, 1% bovine albumin are added and the time point of onset of clotting (=clotting time) is determined turbidimetrically.

In the so-called prothrombin-time-derived fibrinogen concentration (PT-Fbgen) the fibrinogen content of the sample is deduced from the turbidity of the generated clot (Thromborel-S®, DadeBehring). Problematic is here the uncertain thrombin-activity, that varies from patient to patient, that causes in the PT the clotting of the fibrinogen; therefore the clinical reliability of this assay is doubtful (Mackie et al., Thromb Haemost, 2002; 87: 997-1005; s. example 1.1.3).

As well as 10fold dilution of the sample according to Clauss as usage of a polymerization inhibitor in the modified Clauss-method and/or extremely high thrombin-concentrations (EP-B-0137269, DE-A-4133946, U.S. Pat. No. 6,448, 024) are unphyiological. In all these tests it is not considered that fibrinogen can react unphysiologically in unphysiological matrix—matrix is defined as the fluid with all its components in which the substance to be tested for is embedded in (i.e. the surrounding of the analyte)—and/or at unphysiologically high thrombin-activities, as demonstrated according to the present invention (s. FIG. 1a-d, 6a,b).

Aim of the present invention was therefore, to make available a method for the determination of fibrinogen-activity and/or a method for the determination of the fibrinogen-concentration and/or for the determination of the concentration of fibrinogen-derivatives, that is as simple as possible in the application, that detects as precise as possible the true activities and/or concentrations, and that can be accomplished as fast as possible and that does not depend on the addition of unphysiologically high concentrations of thrombin.

This task is solved by turbidimetric matrix-independent methods, i.e. by procedures that measure the fibrinogen-activity and/or fibrinogen- and/or fibrinogen-derivatives-concentration by means of increase in turbidity of the solution to be analyzed. These procedures are named in the following Fibrinogen Functional Turbidimetric Assay (FIFTA) and Fibrinogen Antigenic Turbidimetric Assay (FIATA).

FIFTA is a procedure of determination of fibrinogen and/or fibrinogen-derivatives and particularly of determination of fibrinogen-activity, that comprises the following steps:

a) to a solution to be analyzed for fibrinogen and/or fibrinogen-derivatives albumin and/or thrombin in dissolved form is added, resulting in final concentrations of less than 2 IU/ml, preferably less than 1.5 or 1 IU/ml, and/or less than 150 mIU or 100 mIU per 50 µl sample, especially less than 0.8 or 0.5 IU/ml and/or less than 80 or 50 mIU thrombin per 50 µl sample, and/or 1.7-10% (w/v), preferably more than 2.5% (w/v), especially more than 4% (w/v) albumin.

b) the increase in absorbance of the so obtained mixture is determined.

The FIFTA imitates the physiological conversion of fibrinogen to fibrin, as it occurs in plasma. The FIFTA can be performed quite simply, even at room temperature. Concerning machine equipment, a simple photometer is sufficient, particularly a microtiterplate photometer, special coagulometers or clotting-detecting-systems, i.e. systems that detect clotting times, are not necessary.

In a preferred form the procedure is characterized thereby, that it can be performed without addition of a polymerization inhibitor.

The solution to be analyzed is preferably blood or plasma of blood, to which preferably citrate, EDTA, heparin and/or a guanidine-compound as e.g. arginine was added. The solution can be used e.g. in a volume between 0.1 and 100 µl, preferably between 5 and 50 µl, especially in a volume of 25-50 µl.

Albumin and thrombin preferably are together in dissolved form in a fluid, before they are added to the to be analyzed solution. The volume-volume ratio between the solution to be analyzed and solution to be added containing albumin- and/or thrombin is preferably between 1:1 and 1:5, particularly preferred about 1:2.

Accordingly, the thrombin- and/or albumin-containing solution (FIFTA-reagent) can be used e.g. in a volume between 0.2 and 200 µl, preferably in a volume between 10 and 100 µl, especially in a volume of about 50-100 µl.

The optimal thrombin-concentration in the FIFTA-reagent is between 50 and 1000 mIU/ml (addition of 5-100 mIU thrombin per 50 µl sample), preferably between 100 and 500 mIU/ml, particularly preferred between 200 and 400 mIU/ml, especially at about 300 mIU/ml, above all if it is used in a relation 2:1 to the solution to be analyzed. Thrombin-concentrations in the FIFTA-reagent of 200-450 mIU/ml result into a ΔA/5 min (RT) of about 170-250 mA for pooled normal plasma (100% of norm functional fibrinogen=2.8 g/l active fibrinogen) and into 250-350 mA/5 min (RT) for pooled patient plasma with 144% of norm functional fibrinogen, if the thrombin-reagent is used in the relation 2:1 to the solution to be analyzed. Alternatively, fibrinogen can be converted by another protein and/or mixture of proteins, as e.g. reptilase or staphylocoagulase. If appropriate, the FIFTA-reagent can contain calcium-ions, especially 10-15 mM if the relation FIFTA-reagent: sample=2:1.

The optimal albumin-concentration in the FIFTA-reagent is 2 to 20%, especially 4 to 8%, preferably about 6%, above all if it is used in relation of 2:1 to the solution to be analyzed. Especially preferred is the usage of bovine serum albumin (BSA) or human albumin. Alternatively, compounds that can substitute albumin, that are known to the specialist, e.g. proteins or degradation products of proteins as gelatine, can be used. The addition of albumin prevents a falsification of the measurement result by hypoproteinemic plasmas, that would result into an appararent increase of the fibrinogen-value (FIG. 6a,b).

Preferably also Polybrene® is added to the FIFTA-reagent. The optimal polybrene-concentration in the FIFTA-reagent is between 0 and 30000 µg/ml, particularly preferred between 0 and 1000 µg/ml, especially preferred between 200 and 800 µg/ml, especially at about 400 µg/ml, above all if the FIFTA-reagent is used in the relation 2:1 to the solution to be analyzed, and/or addition of 0-100 µg polybrene per 50 µl sample, especially preferred 20-80 µg per 50 µl sample, particularly about 40 µg polybrene per 50 µl sample.

For analysis of heparin-plasmas (plasmas with up to 100 IU/ml heparin) the polybrene-concentration in the FIFTA-reagent might be 1000-30000 µg/ml, if appropriate, and/or the polybrene-amount to be added 100-3000 µg per 50 µl sample.

Alternatively, a heparin-neutralising agent as e.g. polybrene or heparinase can first be added and then the thrombin reaction can be started. Herefore, heparin-plasmas can be first mixed with 25 µl 4-200 mg/ml, preferred 10-100 mg/ml, especially about 50 mg/ml Polybrene® in 40 mM citrate, pH 7.4, per 50 µl plasma, i.e. addition of 100-5000 µg, preferred 250-2500 µg, especially about 1250 µg polybrene per 50 µl sample (s. FIG. 3).

Using 400 µg/ml Polybrene®, up to 20 IU/ml heparin in plasma is neutralized. Normal heparin-concentrations in blood are up to 0.2 IU/ml. In e.g. cardiac surgery-patients the heparin-concentration can be elevated up to 10 IU/ml plasma. However, the fibrinogen-determination just in these patients is very important since just in these patients the risk to develop a pathologic disseminated intravascular coagulation is very high. The high heparin-concentration would strongly disturb the fibrinogen-determination; therefore the addition of polybrene to neutralize the heparin is necessary to obtain reliable assay-results; e.g. if the FIFTA-reagent would lack polybrene, plasmatic heparin-concentrations ≧0.63 IU/ml would completely inhibit the added thrombin in the test system described in Table 1. The inhibitory concentration 50% would then be 0.1 IU/ml heparin.

The obove mentioned components of the FIFTA-reagent are preferably dissolved in a buffer, especially preferred in a phosphate-buffered NaCl (PBS solution; 10 mM $Na_2HPO_4$, 138 mM NaCl, 2.7 mM KCl, pH 7.4).

The FIFTA is accomplished preferably at a temperature between 0° C. and 42° C., especially preferred at about 37° C. or at room temperature, because the latter temperature is the easiest to handle. The reaction time is preferably between 20 seconds and 60 minutes.

The optimal reaction time for the FIFTA is 1 to 20 min at room temperature, especially preferred 2 to 10 min, above all 3 to 7 min, especially about 5 min. The according times for 37° C. result by division of the before indicated times with the factor 2.5.

The measurement of the turbidity is done preferably by spectrometric measurement of the absorbance at a wave length between 280 and 650 nm, especially preferred at about 405 nm.

The measurement is standardized by comparison with a solution of a known concentration of functional fibrinogen, preferably by comparison with an aliquote of a pooled normal plasma, that corresponds to 100% of norm (mean value (MV) of the normal range=2.8 g/l).

According to the invention the FIFTA is a procedure that can detect both very high and very low fibrinogen-activities very exactly. Thus, concentrations of more than 200%, preferably more than 220%, particularly more than 240% of norm and values less than 50%, preferably less than 40%, particularly less than 30% of norm can be detected by the FIFTA. In a preferred form the lower detection limit can be decreased to 10% of norm.

After about 15 min incubation at room temperature the assay approaches asymptotically maximal absorbance values (for 100% of norm plasma=about 420 mA). The halfmaximal absorbance increase at room temperature occurs after 4 min. About 60% of the turbidity maximum results after about 5 min (RT). The FIFTA in optimal performance is linear up to a fibrinogen-activity of about 250% of norm. The lower detection limit in the 5 min incubation (RT) version of FIFTA is 25% of norm. The lower detection limit decreases to 7% of norm (0.2 g/l), if the turbidity increase/15 min (RT; or ΔA/5-6 min 37° C.) is determined.

The intra- and inter-assay coefficients of variation (CV)-values are less than 4%. The normal range of functional fibrinogen, measured by FIFTA, is 100% ±20% (mean value ±1 standard deviation (SD)). The FIFTA correlates with the modified Clauss-Method for n=334 patients with r=0.843.

The FIFTA is preferably used for diagnostic purposes, especially in the pathologic disseminated intravascular coagulation and to assess the patient-risk for atherothrombotic diseases as myocardial or cerebral ischemia/infarction.

Subject of the present invention is therefore also a diagnostic for fibrinogen, containing thrombin and/or albumin and if appropriate polybrene. The components might hereby exist in already dissolved form, as previously described, or exist in dry form, whereby the components have to be transformed into the dissolved form during the assay. Preferred, according to the invention, are concentrations and solutions as previously described. The present invention is preferably a diagnostic one for diagnosis of pathologic disseminated intravascular coagulation and/or a diagnostic to assess the patient-risk for atherothrombotic diseases as myocardial or cerebral ischemia/infarction. According to the invention preferred for the usage are hereby concentrations and solutions as described before.

Subject of the present invention is also a test system or kit to measure fibrinogen and/or fibrinogen-derivatives, characterized thereby that it comprises a solution containing thrombin and/or a solution containing albumin and if appropriate a solution containing polybrene, whereby thrombin, albumin and/or polybrene might be in the same or in different solutions. According to the invention preferred for the usage are hereby concentrations and solutions as described before.

Subject of the present invention is furthermore the usage of a diagnostic, a test system, or a kit for the determination of the fibrinogen- and/or fibrinogen-derivate concentration and/or activity.

Surprisingly, furthermore it was found, that the commercially available antibiotic vancomycin interacts with fibrinogen and/or fibrinogen-derivatives in such a way, which can be used in a turbidimetric assay to determine their concentration. Here the soluble fibrinogen and/or fibrinogen derivative after binding to vancomycin is converted into a unsoluble form. This insoluble fibrinogen- and/or fibrinogen-derivative-form precipitates. The thereby generated turbidity is a direct measure for the fibrinogen- and/or fibrinogen-derivative-concentration of the sample.

This reaction is the basis for a simple standardized antigen-test for fibrinogen and/or fibrinogen-derivatives, the Fibrinogen Antigenic Turbidimetric Assay (FIATA).

FIATA is a procedure to determine fibrinogen and/or fibrinogen-derivatives, comprising the following steps:
a) to a solution to be analyzed another solution containing vancomycin is added, preferably in such a way that 0.05-1 µmol, especially preferred 0.1-0.5 µmol, above all 0.15-0.3 µmol, particularly about 0.22 µmol vancomycin per 25 µl plasma are added,
b) the increase in absorbance is measured.

The solution to be analyzed is preferably blood or plasma of blood, particularly citrate-, heparin-, EDTA and/or guanidine-compound-plasma as e.g. arginine-plasma (e.g. addition of 9 parts blood to 1 part 106 mM citrate, 15 IU heparin/ml blood, 1.6 Kalium-EDTA/ml blood, and/or 50-1000 mM arginine (pH 8.7)/ml blood). Also here a simple photometer, especially a microtiterplate photometer, is sufficient.

In the FIATA preferably to one part of sample with a volume of 0.1-100 µl, particularly preferred with a volume of 5-50 µl, above all with a volume of about 25 µl, are added two parts of PBS-buffer (phosphate buffered NaCl, if appropriate containing albumin, especially 6% albumin) accordingly with a volume of 0.2-200 µl, particularly preferred with a volume of 10-100 µl, above all with a volume of about 50 µl, to generate the solution to be measured. Instead of PBS-buffer also another solution (e.g. 0.9% NaCl or $H_2O$) can be used to dilute the sample. This dilution facilitates to detect the subsequent increase in turbidity. If the photometer exaxtly measures small volumes, this dilution step maybe omitted.

The vancomycin-containing solution (FIATA-reagent) is added to the solution to be analyzed preferably in a volume relation of about 2:3, accordingly, respective the obove mentioned volumes, in a volume of 0.2-200 µl, particularly preferred in a volume of 10-100 µl, above all in a volume of about 50 µl.

The vancomycin-concentration in the FIATA-reagent is preferably so chosen, that after addition of the FIATA-reagent to the turbidity measured solution it results a final vancomycin-concentration of 0.4-20 mM, particularly preferred 0.8-4 mM, above all 1-3 mM, especially about 1.76 mM, i.e. especially addition of about 0.22 µmoles vancomycin per 25 µl plasma. In general the vancomycin concentration in the FIATA-reagent accordingly is between 1 and 20 mM, in a preferred performance-form 2 and 7 mM, particularly about 4.4 mM, resulting after dilution into the before-mentioned concentrations. The vancomycin is preferably dissolved in PBS (phosphate-buffered NaCl solution, if appropriate containing albumin, especially 6% albumin). Alternatively, also other to the specialist known buffers can be used for the production of the FIATA-reagent.

The vancomycin-containing solution can be stabilized by a detergent such as Triton-X100®, particularly 0.1% (w/v), and/or a protein such as albumin, particularly 1-7% (w/v).

The FIATA is preferably performed at a temperature of 0-42° C., particularly preferred at about 37° C. or, since most easiest to handle, at room temperature. The optimal reaction time for the FIATA at room temperature is 2 seconds to 10 minutes, preferred 5 seconds to 5 minutes, particularly preferred 10 seconds to 3 minutes, above all 1 to 3 minutes. For 37° C. the reaction times are halved.

The turbidity is determined preferably by spectrophotometric measurement at a wave length of 280-650 nm, particularly preferred at a wave length of about 405 nm.

The measurement is standardized by comparison with a solution of known concentration of fibrinogen, preferably by comparison with an aliquote of a pooled normal plasma, that corresponds to 100% of norm (MV of normal range=2.8 g/l).

The FIATA has a upper limit of linearity of more than 100% of norm, particularly preferred more than 120% of norm, above all more than 140% of norm and/or a lower detection limit of less than 20% of norm, particularly preferred less than 10% of norm, above all less than 5% of norm.

The FIATA is in a preferred performance-form approximately linear up to a fibrinogen concentration of about 150% of norm (4.2 g/l), resulting into a ΔA of 400-800 mA, especially about 600 mA. The lower detection limit is 4% of norm (0.1 g/l).

The intra- and inter-assay CV-values are under 4%. The normal range of the FIATA is 100% ±20% (MV ±1 SD). In n=321 or n=344 patient-plasmas the FIATA (MV=130%; SD=52% or 43%, respectively) correlated with the functional fibrinogen tests a) modified Clauss-method (MV=4.1 g/l; SD=1.7 g/l) with r=0.755 and b) FIFTA (MV=124%; SD=40%) with r=0.813.

The FIATA is suitable not only to measure fibrinogen, but also to measure soluble fibrin and/or denatured fibrinogen-molecules. Therefore, the FIATA is also suitable as a screening-test for dysfibrinogens or unfunctional fibrinogen. To determine the total concentration of fibrinogen and/or fibrinogen derivatives the fibrinogen does not have to be converted into fibrin; therefore the addition of thrombin can be omitted.

The FIATA is so simple that the determination of the fibrinogen- and/or fibrinogen-derivatives-concentration can be performed within seconds even outside a hospital. Therefore the FIATA can contribute to examine patients outside a hospital and to assess their risk for myocardial and/or cerebral ischemia/infarction.

Subject of the present invention is therefore a diagnostic containing vancomycin. The vancomycin might hereby exist in already dissolved form, as previously described, or exist in dry form, whereby it has to be transformed into the dissolved form during the assay. Preferred, according to the invention, are concentrations and solutions as previously described. The present invention is preferably a diagnostic one for diagnosis of pathologic disseminated intravascular coagulation and/or a diagnostic to assess the risk of patients for atherothrombotic diseases as myocardial or cerebral ischemia/infarction. According to the invention preferred for the usage are hereby concentrations and solutions as described before. Particularly the calculation of the FIATA/FIFTA ratio can contribute to diagnose an activation of hemostasis (as e.g. in a DIC) and/or a dysfibrinogenemia. Values ≦1.1, particularly values ≦1.3, are indicative for a DIC and/or a dysfibrinogenemia.

Subject of the present invention is also a test system or kit to measure fibrinogen and/or fibrinogen-derivatives, characterized thereby that it comprises a solution containing vancomycin. According to the invention preferred for the usage are hereby concentrations and solutions as described before.

Subject of the present invention is furthermore the usage of a diagnostic, a test system, or a kit for the determination of the fibrinogen- and/or fibrinogen-derivate concentration.

Tab. 1 and 2 show optimized performance forms for the FIATA and the FIFTA.

TABLE 1

Optimized parameters to perform the FIFTA

50 µl Plasma or Standard (e.g. 100% standard = pooled normal plasma)
100 µl 300 mIU/ml Thrombin, 6% Albumin-PBS,
400 µg/ml Polybrene ® in PBS
A (405 nm)
5 min (RT) or 2 min (37° C.)
ΔA (405 nm)

The optimized FIFTA is performed as follows:

To 50 µl citrated plasma (addition of 9 parts blood to 1 part 106 mM citrate) 100 µl FIFTA-reagent are added, that contain 300 mIU/ml thrombin, 6% albumin-PBS, 400 µg/ml Polybrene® in PBS. The absorption at 405 nm is immediately measured (base value) and exactly after 5 min, if the reaction is performed at room temperature (23° C.). If the reaction is performed at 37° C., the second value is measured after 2 min. A microtiterplate reader (Milenia, DPC, Los Angeles, USA) is used. The increase in absorption (ΔA) is determined and the results are standardized against a pooled plasma of known, preferably of 100% of norm, fibrinogen-activity (Table 1).

TABLE 2

Optimized parameters to perform the FIATA

25 µl Plasma or Standard
(e.g. 100% standard = pooled normal plasma)
50 µl PBS
A (405 nm)
50 µl 4.4 mM vancomycin in PBS
2 min (RT) or 1 min (37° C.)
ΔA (405 nm)

The optimized FIATA is performed as follows:

To 25 µl plasma 50 µl PBS are added and the absorbance (405 nm) is determined (base value). Then 50 µl 4.4 mM vancomycin in PBS are added. The absorbance at 405 nm is determined after 2 min, if the reaction is performed at room temperature (23° C.). If the reaction is performed at 37° C., the second value is determined after 1 min. A microtiterplate reader (Milenia, DPC, Los Angeles, USA) is used. The increase in absorption (ΔA) is determined and the results are standardized against a pooled plasma of known, preferably of 100% of norm, fibrinogen-concentration, and against 0.9% NaCl (zero-value of turbidity) (Table 2).

EXAMPLES

1. FIFTA 1.1. Test-Optimization 1.1.1. Thrombin Concentration

The thrombin concentration in the assay should be as physiologic as possible; neither excessive thrombin nor too low levels of thrombin are suitable for an ideal functional assay for fibrinogen. 50 µl patient-pool (P-Pool; 144% of norm=4.04 g/l active fibrinogen) and 1:2 with 6% bovine serum-albumin phosphate-buffered physiol. NaCl (BSA-PBS) diluted P-Pool were incubated with 100 µl 0-1519 mIU/ml thrombin for 0-15 min (RT) in microtiterplates with wells with flat bottom and the increase in turbidity at 405 nm was determined.

Within the first 5 min reaction time at RT the turbidity increase for P-Pool and for P-Pool diluted 1:2 is nearly linear, if a thrombin reagent with 200-450 mIU/ml thrombin is used (FIG. 1a,b). The correct ratio of 0.5 between absorbance increases for diluted P-Pool and for P-Pool is obtained by 200-450 mIU/ml thrombin (FIG. 1c). The maximal turbidity increase for P-Pool is about 450 mA; about 70% of the maximal turbidity increase is reached using 300 mIU/ml thrombin and 5 min reaction time at RT (FIG. 1d). Therefore, the optimal thrombin concentration in the FIFTA-reagent is 200-450 mIU/ml, resulting into a ΔA/5 min (RT) of 250-350 mA/5 min for P-Pool. 300 mIU/ml was chosen as optimal thrombin concentration in the FIFTA-reagent, i.e. 200 mIU/ml final IIa concentration, resulting into a ΔA/5 min of about 300 mA for P-Pool. The basal absorbance of 100% Pool-Plasma is about 150 mA, addition of 100 µl 6% BSA-PBS increases the absorbance by about 100 mA.

1.1.2. Polybrene Concentration

P-Pool supplemented with 0-80 IU/ml heparin was analyzed in the FIFTA. The FIFTA-reagent contained 200 mIU/ml thrombin, 6% BSA-PBS and 0, 50, 100, 200, 400, 800, or 1600 µg/ml Polybrene® (PB, hexadimethrinebromide).

FIGS. 2a-g demonstrate the neutralization (inhibition) of heparin by polybrene®. If the FIFTA-reagent contains 400 µg/ml polybrene®, plasmatic heparin concentrations up to 20 IU/ml are neutralized.

Polybrene® Addition to Heparinized Plasma

25 µl 0-75 mg/ml Polybrene® in aqua dest. were added to 50 µl P-Pool or to 50 µl P-Pool, that had been supplemented with 100 IU/ml heparin. Then 100 µl 200 mIU/ml thrombin in 6% BSA-PBS, 400 µg/ml PB were added and the increase in absorbance at 405 nm was determined.

Addition of 25 µl≧50 mg/ml PB completely antagonizes 100 IU/ml heparin in 50 µl plasma (FIG. 3). The FIFTA-reagent contains 400 µg/ml polybrene® (PB); therefore, for neutralization of 1 part of 100 IU/ml heparinized plasma 1 part of 26 mg/ml PB is needed. PB-heparin complexes in plasma do not alter the fibrinogen/thrombin turbidity kinetic (FIG. 4).

Turbidity Increase by Heparin/Polybrene® Complexes

50 µl P-Pool with 0-80 IU/ml heparin were incubated with 100 µl FIFTA-reagent without thrombin, that contained 0, 400, 800, or 1600 µg/ml PB. The increase in absorbance at 405 nm was determined.

The basal turbidity increase in heparinized plasma depends on the heparin concentration of the plasma and on PB concentration in the FIFTA-reagent (FIG. 5). The basal turbidity increase by 25 µl 50 mg/ml PB given to 50 µl P-Pool is about 200 mA (FIG. 4).

1.1.3. Albumin Concentration

P-Pool or P-Pool 1:2 diluted wit PBS or 6% BSA-PBS were analyzed in the FIFTA, using the 200 mIU/ml thrombin-reagent without albumin.

Turbidity based functional fibrinogen determinations depend on the albumin concentration of the sample. In contrast, the FIFTA does not depend on the albumin concentration of the sample. However, without albumin in the FIFTA-reagent the FIFTA would depend on the albumin concentration of the sample: if the P-Pool is 1:2 diluted with PBS, the measured fibrinogen in the diluted P-Pool is about 70% of the undiluted plasma instead of 50%; this means that in patients with blood concentrations of albumin of about 50% of norm the turbidimetrically determined functional albumin is about 40% falsely elevated. If the P-Pool is 1:2 diluted with 6% BSA-PBS, the measured fibrinogen in the diluted pool is really 50% of the undiluted pool (FIGS. 6a,b).

Addition of 6% albumin to the FIFTA-reagent results into the correct 50% result in all diluted plasmas, either diluted with PBS or with 6% albumin.

Comparison of the assay-methods for fibrinogen according to the invention with the state of the art For comparison, pooled patient plasma (P-Pool, n=32 single plasmas; normal prothrombin time and activated partial thromboplastin time) as well as 1:2, 1:4 and 1:8 dilutions of the P-Pool with 0.9% NaCl was tested with the following methods for fibrinogen:
A) FIFTA (Tab. 1)
B) FIATA (Tab. 2)
C) Modified Clauss (DadeBehring, conditions page 1, lines 31-38)
D) PT-Fbgen (DadeBehring, conditions page 1, lines 40-42)
Result:

| Method | Plasma 1:1 | Plasma 1:2 | Plasma 1:4 | Plasma 1:8 | Plasma 1:16 |
|---|---|---|---|---|---|
| A) | 128% | 64% | 32% | 16% | 8% |
| B) | 129% | 65% | 32% | 16% | 8% |
| C) | 3.7 g/l | 2.0 g/l | 0.6 g/l | n.m. | n.m. |
| D) | 3.5 g/l | 2.1 g/l | 1.3 g/l | 0.8 g/l | n.m. | n.m. = not measurable

One recognizes, that the fibrinogen concentration in the FIFTA and FIATA is correctly determined. In contrast, the fibrinogen-value in the modified Clauss-method for the 1:2 diluted plasma is 8% too high and the fibrinogen-value for the 1:4 diluted plasma is 35% too low compared to the value which can be expected. In the PT-Fbgen method the fibrinogen-values are for the 1:2 diluted plasma 20% too high, for the 1:4 diluted plasma 49% too high, and for the 1:8 diluted plasma 83% too high compared to the the value which can be expected.

Some patients, especially intensive care patients, have plasmatic albumin concentrations of about 10 g/l, i.e. less than 25% of norm. This can result into strongly falsified fibrinogen values, such plasmas are analyzed for fibrinogen by means of methods according to the state of the art.

1.1.4. Reaction Kinetic

The FIFTA was performed with P-Pool and with 6% BSA-PBS dilutions of P-Pool. The increase in absorbance was determined after 0-15 min and after 25 min, 75 min, 17 h at RT. Furthermore, the FIFTA was performed with a 100% normal plasma pool and a 200% fibrinogen-plasma pool (256% Fbgen-Pool-Plasma diluted with 100% normal pooled plasma).

The 256% Fbgen-Pool-Plasma, the 256% Fbgen-Pool-Plasma, that had been diluted with 6% BSA-PBS to 120% or to 63% were analyzed in the FIFTA with 0-17 min reaction time (RT). The 120%/256% and the 63%/256% turbidity ratios were calculated. A 300% Fbgen-Pool-Plasma, generated by addition of purified active fibrinogen to the 256% Fbgen-Pool-Plasma, and the 1:2 diluted (with 6% BSA-PBS) 300% Fbgen-Pool-Plasma were analyzed in the FIFTA.

FIGS. 7a,b show the reaction kinetic of the FIFTA. At about 15 min RT reaction time the assay reaches asymptotically its maximal value. At about 5 min RT reaction time about 60% of the maximal value has been reached. FIG. 7b shows the linearity of the calibration curves in FIFTA. There appears a linear relationship between active fibrinogen and turbidity increase at reaction times $\geq$5 min RT and active fibrinogen <150% of norm.

FIG. 7c demonstrates the reaction of 200% and 100% Pool. The 100%/200% turbidity ratio is stable at 0.5 at a reaction time >4 min RT.

FIG. 7d shows the reaction of 256% Fbgen-Pool-Plasma, 120% plasma and 63% plasma.

Halfmaximal turbidity increase is reached at 4 min (RT), at 5 min incubation 60% of the maximal $\Delta A$ appears. The 120%/256% or the 63%/256% ratio reaches the correct value of 0.47 or 0.25, respectively, at about 5 min reaction time, reaction times >8 min (RT) result into falsely elevated ratios, indicating loss of linearity of the FIFTA (FIG. 7e).

FIGS. 7f,g demonstrate the reactions of 300% Fbgen-Pool-Plasma and of 1:2 diluted (with BSA-PBS) Fbgen-Pool-Plasma. The 150%/300% turbidity-increase ratio reaches the correct value of 0.5 only at about 2 min reaction time at RT. At $\geq$5 min (RT) the ratio increases to values $\geq$0.7. This means, that active fibrinogen levels >250% of norm can be measured linearly by decreasing the reaction time (2 min RT or 50 s 37° C.) or by prior 1:2 dilution of the sample.

Reaction Kinetic at 37° C.

The FIFTA was performed with 256% Fbgen-Pool-Plasma and with 256% Fbgen-Pool-Plsma that had been diluted 1:2 with 6% BSA-PBS. After reaction times of 30-370 seconds in 10 seconds-intervals and after 20 and 60 min in a 37° C. water bath the increase in turbidity at 405 nm was determined. The 128%/256% turbidity ratio was calculated for each reaction time.

FIG. 8a shows the turbidity increase in dependence of the reaction time at 37° C. The halfmaximal turbidity increase occurs at a reaction time of 100 seconds (37° C.) for the 256% Fbgen-Pool-Plasma and at a reaction time of 190 seconds (37° C.) for the 128% dilution of the Fbgen-Pool-Plasma. The 128%/256% absorbance-increase ratio reaches the correct value of 0.5 at a reaction time of 24 min (37° C.) (FIG. 8b). Therefore, the optimal FIFTA reaction time is 5 min at RT or 2 min at 37° C.

1.1.5. Optimization of Absorbance Wavelength for Turbidity

The FIFTA was performed with P-Pool and with 256% Fbgen-Plasma-Pool; reaction time=30 min at RT. The resulting absorbance was determined at 405 nm, 450 nm, 595 nm, and 650 nm by microtiterplate reader.

Turbidity is best followed at 405 nm. Increasing the wave length results into a decrease in turbidity (FIG. 9).

1.2. Calibration with Purified Fibrinogen 250 mg lyophilized purified human fibrinogen (Haemochrom-Enzyme Res., Essen, Germany) were reconstituted with 12.5 ml either 6% BSA-PBS or P-Pool (containing 4.04 g/l Fibrinogen). The obtained supplemented fibrinogen samples were 1:2, 1:4, 1:8, 1:16, 1:32, 1:64, 1:128 diluted either with 6% BSA-PBS or P-Pool, respectively, and the FIFTA was performed. The result of this addition-calibration was, that only 46% of the purified fibrinogen is functionally active; therefore samples with 0-9.3 g/l active fibrinogen in 6% BSA-PBS or samples with 4.04-13.3 g/l fibrinogen in P-Pool were generated.

FIGS. 10a,b show the reaction kinetic of purified fibrinogen in BSA-PBS in the FIFTA in dependence of reaction time at RT or in dependence of the active fibrinogen concentration, respectively. At 15 min RT about 75% of maximal turbidity is achieved. There appears no further increase, if the reaction time is prolongated from 48 min to 158 min or 18 h.

FIGS. 10c,d demonstrate the reaction kinetic of P-Pool, that was supplemented with purified fibrinogen, in dependence of reaction time at RT or in dependence of the resulting active fibrinogen concentration, respectively. At 15 min RT about 80% of maximal turbidity is reached. Prolonging the reaction time from 48 min to 158 min or 18 h results into a 5-10% decrease in final turbidity. FIG. 10e shows the comparison between fibrinogen in BSA and fibrinogen in plasma.

1.3. Linearity

256% Fbgen-Plasma-Pool and 256% Fbgen-Plasma-Pool supplemented with purified active fibrinogen to 277% or to 300% of norm were analyzed in the FIFTA and in a FIFTA-version with halved test-volumes.

225% Fbgen-Plasma-Pool was supplemented with active fibrinogen to 300% Fbgen-Plasma-Pool and diluted with physiol. NaCl. These plasma-samples with 0-300% fibrinogen were measured in the FIFTA.

The FIFTA is nearly linear in the fibrinogen activity range of about 25-250% of the normal mean value (0). 100% of norm fibrinogen plasma results into a $\Delta A$ of about 250 mA (FIGS. 11a-c). The FIFTA can also be performed with 25 µl plasma and 50 µl reagent, resulting into a $\Delta A$ about 125 mA in the microtiter plate (FIG. 11a).

Variation of Test Volumes

256% Fbgen-Pool-Plasma and 256% Fbgen-Pool-Plasma, diluted 1:2 with 6% BSA-PBS, were analyzed in the FIFTA (50 µl sample +100 µl thrombin reagent). 67 µl 256% Fbgen-Pool-Plasma or 1:2 diluted Fbgen-Pool-Plasma were incubated with 83 µl thrombin-reagent. 100 µl 256% Fbgen-Pool-Plasma or 1:2 diluted Fbgen-Pool-Plasma were incubated with 50 µl thrombin-reagent, containing 600 mIU/ml thrombin; the absorptions-ratios 128%/256% were calculated.

FIGS. 12a,b demonstrate that only the 50 µl+100 µl FIFTA version—in contrast to a 67 µl+83 µl or to a 100 µl+50 µl assay version—results into the correct 128%/256% absorbance-increase ratio of 0.5 at 5 min RT.

1.4. Sensitivity

To determine the lower detection limit of the FIFTA, 6% BSA-PBS or pooled normal serum (0% of norm fibrinogen) was analyzed tenfold, and the standard deviation (SD) was determined. The lower detection limit was defined as 3fold the SD of the 0-value.

The lower detection limit of the FIFTA is 25% of norm (0.7 g/l) if the reaction time is 5 min (RT); increasing the reaction time to 15 min (RT) the lower detection limit decreases to 7% of norm (0.2 g/l).

1.5. Precision

The 144% P-Pool was tenfold analyzed intra-assay and inter-assay. The mean values were determined and the coefficients of variation (CV) were calculated.

For the 144% standard (P-Pool) an intra-assay CV of 1.8% and an inter-assay CV of 3.4% was determined.

1.6. Normal Range n=39 normal citrated plasma samples were analyzed in the FIFTA to obtain mean value (0) and standard deviation (SD), giving the normal range (0±1 SD) of fibrinogen function in plasma. The assay was calibrated against pooled normal plasmas and against commercially available deep-frozen 100% normal plasma that contained 2.8 g/l active fibrinogen (Haemochrom, Essen, Germany).

The normal range of FIFTA is 100% ±20% (0±1 SD); 100%=2.8 g/l.

1.7. Correlation with Clauss-Method

In=334 unselected patient plasmas (≦6 h old; at the time point of the usual discarding the samples) the FIFTA was performed and compared to the routinely measured fibrinogen concentrations (modified Clauss-Method (Multifibren U®) on a Behring Coagulation Timer, DadeBehring, Marburg, Germany: 100 µl sample+200 µl 50 IU/ml bovine thrombin, 0.15 g/l gly-pro-arg-pro-ala-amide, 1.5 g/l $CaCl_2$, 15 µg/ml polybrene®, 0.8 g/l polyethylene glycol 6000, 6.4 g/l NaCl, 50 mM Tris, 1% bovine albumin; turbidimetric determination of coagulation time).

In n=334 unselected patient plasmas the FIFTA (0=132%, SD=41%) was performed and compared to the modified Clauss-Method (0=4.18 g/l, SD=1.65 g/l); the correlation factor r=0.843; y=20.9 x+44.528 (FIG. 13a). The FIFTA results of the patients distribute with a normal Gaussian distribution (FIG. 13b).

1.8. Inhibition of Fibrin Generation by Heparin 1.8.1. Inhibitory concentration 50% (IC50) of Heparin Against Thrombin 50 µl 100% Pool were added to 10 µl 0-160 IU/ml heparin. 100 µl 200 mIU/ml thrombin in 6% BSA-PBS (without polybrene®) were added and the increase in absorbance at 405 nm was followed.

Heparin dose-dependently inhibits the turbidity increase (FIG. 14a). Heparin concentrations ≧0.63 IU/ml completely inhibit thrombin in the assay system described. The IC50 is approx. 0.1 IU/ml heparin (FIG. 14b).

1.8.2. Inhibitory Time Point 50% (ITP50) of 10 IU/ml Heparin-thrombin Interaction 50 µl P-Pool were incubated with 100 µl 200 mIU/ml thrombin in 6% BSA-PBS (without polybrene®). At 0 min (prior to thrombin addition) and 0.5-11 min reaction time (at RT) 10 µl 160 IU/ml heparin in 6% BSA-PBS was added (final heparin conc. in plasma+thrombin reagent=10 IU/ml; this heparin conc. increased the absorbance by 20 mA; all test results were corrected by this heparin induced turbidity increase). The turbidity increase at 405 nm was determined immediately after each heparin addition step and as a function of incubation time.

To determine the heparin addition time point (at RT) that is needed to decrease the 5 min, 10 min, 15 min or 20 min turbidity increase by 50% (inhibitory time point 50%=ITP), 50 µl P-Pool were incubated with 100 µl 200 mIU/ml thrombin in 6% BSA-PBS (without polybrene®)). After 0 s (prior to thrombin addition) and 10-140 s (in 10 s intervals) 10 µl 160 IU/ml heparin in 6% BSA-PBS were added. The turbidity increase at 405 nm as a function of incubation time (3-20 min) was determined.

Heparin can only inhibit fibrin generation within the first 2 min (RT) (FIGS. 15a-c). Inspite of addition of 10 IU/ml final conc. heparin at 30 seconds incubation time (RT) there is still about 50% of fibrinogen→fibrin conversion; i.e. 133 mIU/ml thrombin convert about 50% of plasmatic fibrinogen within approximately 30 seconds. The 15 min fibrin turbidity is >80% of maximal turbidity as observed previously. However, the turbidity increase in presence of 10 IU/ml heparin within the first 5 min reaction time is superior to that in absence of heparin. Thus, the time point of heparin addition that results into a 50% decrease of $\Delta A$ (ITP50) at 5-20 min incubation time (RT) is approximately 30 s.

1.9. Inhibition of Fibrin Generation by Arginine a) 10 ml FIFTA-reagent were added to 5 ml P-Pool, the mixture was drawn into a multipipette, and 100 µl of this mixture were immediately pipetted into a microtiterplate, which had been prepared with 200 µl 0-1500 mM arginine, pH 8.7, per well, resulting in final arginine conc. of 0, 16, 31, 62.5, 125, 250, 500, 1000 mM. The turbidity increase at 405 nm was monitored as a function of incubation time at RT.

b) 10 ml FIFTA-reagent were added to 5 ml P-Pool, the mixture was drawn into a multipipette, and after 0-4 min (RT), 100 µl thereof mixture were pipetted into a microtiter-plate, which had been prepared with 200 µl 0-1500 mM arginine, pH 8.7, per well. The turbidity at 405 nm was immediately measured after each addition step of the reaction mixture to the arginine in the plate. The control basal absorbance was determined by addition of FIFTA-reagent without thrombin to plasma and pipetting the mixture to 0-1500 mM arginine. The turbidity increase was calculated by subtracting the basal absorbance from the absorbance generated by thrombin (addition of 100 µl FIFTA-reagent without thrombin results into an approximate increase of absorbance of 100 mA compared to the absorbance of 50 µl sample).

c) 50 µl P-Pool were incubated with 100 µl FIFTA-reagent. After 0-30 min (RT) 0-70 µl 1.5 M arginine, pH 8.7, were added and after the last time point (30 min) the final turbidity increase was determined at 405 nm.

A final arginine conc. ≧125 mM completely inhibit turbidity increase, if the arginine acts since the begin of thrombin action (FIGS. 16a-c). Halfmaximal turbidity increase occurs at 62.5 mM arginine. 16 mM arginine increases the turbidity increase by about 20%. Final arginine conc. ≧250 mM completely inhibit turbidity increase, if arginine acts in the first 4 min (RT) of the thrombin/fibrinogen interaction. 125 mM arginine can only inhibit turbidity increase, if it acts in the first 100 seconds (RT) of thrombin/fibrinogen interaction. Addition of arginine at 2.5 min thrombin/fibrinogen reaction time results into a decrease of ΔA, which is dependent on the arginine concentration. Since a big clot is generated in the multipipette syringe, the values at >3 min (RT) reaction time are not valid. FIG. 16d shows that final arginine conc. ≧250 mM can only inhibit turbidity increase, if they are added in the first 3 min (RT) of the thrombin/fibrinogen interaction. Halfmaximal turbidity increases at the 7 min or the 15 min reaction time point result by 94 mM or 477 mM arginine, respectively.

1.10. Fibrin Dissolution by Arginine

50 µl P-Pool were incubated with 100 µl FIFTA-reagent. After 30 min (RT) 10 µl or 70 µl 1.5 M arginine, pH 8.7 (final arginine conc. 94 mM or 477 mM) were added and the final turbidity increase was determined at 405 nm after 0-132 min (RT).

Final arginine conc. of 477 mM added at the 12 min or 30 min thrombin/fibrinogen reaction time point decreases ΔA in a function of incubatin time: halfmaximal decrease occurs after additionly 30 min (RT) (FIG. 17). Increasing the arginine incubation to >100 min demonstrates that about 30% of once generated maximal ΔA remains refractory to clearing.

2. FIATA 2.1. Inactivation of Fibrinogen by Vancomycin

200 µl of 256% of norm active fibrinogen in P-Pool were incubated with 25 µl 0-100 mM vancomycin or 0-100 mM chloramine-T® in aqua dest. for 15 min (37° C.). 50 µl samples of these reaction mixtures were withdrawn and incubated with 100 µl 200 mIU/ml thrombin, 400 µg/ml polybrene®, 6% BSA-PBS. The results were standardized by simultaneous analysis of 144% of norm active fibrinogen in P-Pool.

Vancomycin concentration-dependently inactivates plasmatic fibrinogen: approximately 1 mM vancomycin inactivates 50% of fibrinogen in human plasma (IC50=1 mM). For comparison, the IC50 of chloramine T® against plasmatic fibrinogen is about 2 mM (FIG. 18).

2.2. Do Antioxidants Quenching the Reaction Between Vancomycin and Plasmatic Fibrinogen?

750 µl 256% active fibrinogen in P-Plasma was supplemented with 250 µl of a) the $^1O_2$ quenchers methionine (200 mM) or sodium ascorbate (200 mM), b) the —OH radical quencher mannitol (200 mM), or c) $H_2O$. 25 µl samples thereof were incubated with 25 µl 0-2.5 mM vancomycin or 0-5 mM chloramine-T® in PBS for 15 min at 37° C. Then 100 µl 200 mIU/ml thrombin, 400 µg/ml polybrene® in 6% BSA-PBS were added and the mixture was incubated for 3, 5, 9, and 17 min (RT). The respective fibrinogen activities at the 5 min incubation time point were calculated against the 100% of norm control-pool (0 mM vancomycin or chloramine-T®).

The vancomycin-interaction with fibrinogen in plasma cannot be quenched by methionine, ascorbate, or mannitol (FIG. 19a). The 100% control of methionine or $H_2O$ had a turbidity increase/5 min (RT) of 386±11 mA, that of ascorbate was 360±14 mA and that of mannitol was 435±12 mA. The control experiment with chloramine-T® instead of vancomycin showed that the chloramine reaction with plasmatic fibrinogen can be quenched by methionine or by ascorbate (FIG. 19b). Thus, the reaction mechanism of the vancomycin interaction with fibrinogen—in contrast to that between chloramines and fibrinogen—seems not to involve reactive oxygen species of the type of singlet oxygen.

2.3. FIATA Optimization

Vancomycin Concentration

50 µl P-Pool or 1:2 or 1:4 diluted (in 6% BSA-PBS) P-Pool were incubated with 50 µl 0-6.8 mM vancomycin in PBS. The turbidity increase at 405 nm was determined after 1 min (RT). 25 µl Fbgen-Pool (300% of norm; 8.4 g/l) were incubated with 125 µl 0.55 mM, 1.1 mM, or 2.2 mM vancomycin in PBS for 1 min (RT). Then the turbidity increase at 405 nm was determined.

Increasing concentrations of vancomycin result into increasing turbidity of the reaction mixture. This proportional increase can be observed in P-Pool and in the 1:2 diluted or 1:4 diluted P-Pool. The own turbidity of 4.4 mM vancomycin in PBS (0% fibrinogen standard in BSA) is <50 mA at 405 nm (FIG. 20a). This turbidity increase occurs within seconds and is stable for at least 10 min.

FIG. 20b demonstrates that 68.8 µmoles of vancomycin given to 25 µl 300% Fbgen-Pool results into a saturation of turbidity increase at about 4 g/l fibrinogen. Using 137.5-275 µmoles of vancomycin this saturation occurs at 6-8 g/l fibrinogen. The optimal vancomycin concentration in the vancomycin reagent of the FIATA is 3-6 mM.

2.4. FIATA Calibration with Purified Fibrinogen 250 mg lyophilized purified fibrinogen were reconstituted with 12.5 ml of either 6% BSA-PBS or P-Pool. The so obtained supplemented fibrinogen samples were 1:2, 1:4, 1:8, 1:16, 1:32, 1:64, 1:128 diluted with either BSA-PBS or P-Pool, respectively, resulting into samples containing either 0-20 g/l fibrinogen in BSA-PBS or samples containing 4-24 g/l fibrinogen in P-Pool.

FIG. 21 shows the reaction of purified fibrinogen in the FIATA. A fibrinogen concentration of 10 g/l results into a ΔA of about 1000 mA, both for fibrinogen in 6% albumin and for fibrinogen in P-Pool. The FIATA is linear up to about 8 g/l (286% of norm) fibrinogen in the sample, resulting into a ΔA of about 800 mA.

2.5. FIATA Linearity 0-55 µl 300% of norm (8.4 g/l) plasma-pool were incubated (Table 1) with a) 50 µl PBS and 50 µl 4.4 mM vancomycin in PBS or b) 100 µl PBS and 100 µl 4.4 mM vancomycin in PBS. 0-35 µl 300% pool were incubated with 35-0 µl PBS (for volume compensation) and a) 50 µl PBS and 50 µl 4.4 mM vancomycin in PBS or b) 100 µl PBS and 100 µl 4.4 mM vancomycin in PBS.

The FIATA is nearly linear up to a fibrinogen concentration of about 150% of norm (4.2 g/l)

(FIG. 22a,b). Doubling the assay-volumina results into doubling of the absorbance at 405 nm (FIG. 22c). Since the own turbidity of 50 μl plasma might be >500 mA (hypertryglyceridemic or hyperbilirubinemic patients), the 25 μl/50 μl/50 μl FIATA-version is the preferred one (FIG. 22d). A modified FIATA with 50 μl sample and 50 μl reagent is linear only up to about 100% of norm fibrinogen (FIG. 22e).

2.6. FIATA Sensitivity

To determine the lower detection limit of the FIATA, pooled normal serum (0% of norm fibrinogen) was analyzed tenfold, and the standard deviation (SD) was determined. The lower detection limit was defined as 3*SD of the 0-value.

The lower detection limit of the FIATA—as defined as threefold the SD of the 0% value—is 4% of norm (0.1 g/l).

2.7. FIATA Precision

The P-Pool (143% of norm=4.0 g/l fibrinogen) was tenfold analyzed intra-assay and inter-assay. The mean values were determined and the coefficients of variation (CV) were calculated.

For the 143% standard (P-Pool) an intra-assay CV of 1.9% and an inter-assay CV of 3.5% was determined.

2.8. FIATA Normal Range n=39 normal citrated plasma samples were analyzed in the FIATA to obtain mean value (0) and standard deviation (SD), giving the normal range (0±1 SD) of plasmatic fibrinogen measured by the FIATA. The assay was calibrated with pooled normal student plasmas and with 100% normal plasma, containing 2.8 g/l fibrinogen, deep frozen without lyophilization additives (Haemochrom, Essen, Germany).

The normal range of FIATA is 100% ±20% (0±1 SD), 100% of norm=2.8 g/l.

2.9. FIATA Correlation with Functional Fibrinogen Determinations

In n=321 unselected patient plasmas (≦6 h old; at the time point of the usual discarding the samples) the FIATA was performed and compared to the routinely measured fibrinogen concentrations (modified Clauss-Method (Multifibren U®) on a Behring Coagulation Timer, DadeBehring, Marburg, Germany). In n=344 unselected patient samples the FIATA was compared to a new turbidimetric functional fibrinogen assay, the FIFTA: 50 μl plasma +100 μl 300 mIU/ml IIa, 400 μg/ml polybrene®, 6% BSA, PBS; determination of ΔA/5 min (RT).

In n=321 unselected patient plasmas the FIATA (0=130±52%) correlated to a modified Clauss-Method (0=4.1±1.7 g/l) with r=0.755; y=19.521x+49.165 (FIG. 23a). In n=344 unselected patient plasmas the FIATA (0=130±43%) correlated to the functional fibrinogen determination in the FIFTA (0=124±40%) with r=0.813; y=0.861x+22.993 (FIG. 23b). The FIATA-results of the patients (n=344) are normally distributed with a Gauss-distribution (FIG. 23c).

2.10. Precipitation of Plasmatic Fibrinogen by Vancomycin

25 μl of 143% (4.0 g/l) P-Pool were incubated with 25 μl 0-50 mM vancomycin in PBS, 50 μl PBS, 0.1% Triton X 100® and 50 μl 850 mM KCl in $H_2O$ for 1 min (RT). The turbidity at 405 nm was determined. To reverse precipitation 0-110 μl 1 M $NaHCO_3$, pH 8.6, or $H_2O$ were added to 50 μl P-Pool that had been reacted with 50 μl 4.4 mM vancomycin in PBS for 1 min (RT). For pH-studies 5 ml P-Pool were mixed with 5 ml PBS and 0-1750 μl 1 M $NaHCO_3$, pH 8.6.

5 ml P-Pool were incubated with 5 ml 4.4 mM vancomycin in PBS for 3 min (RT). Then the reaction mixture was centrifuged at 2500 g (4000 rpm) for 10 min. The supernatant was separated from the precipitate. The precipitate was not washed or was washed 3× with dest. $H_2O$ (resuspension, centrifugation, resuspension, . . . ). The unwashed precipitate was solubilized by addition of 500 μl 1 M $NaHCO_3$, pH 8.6, and 4500 μl PBS; the washed precipitate was solubilized by addition of 300 μl 1 M $NaHCO_3$ to 1700 μl in dest. $H_2O$ resuspended precipitate. 3 preparations of washed precipitate were also dried at room temperature and the dried precipitates were weighed. The solubilized precipitate and the supernatant were functionally analyzed for fibrinogen. 100 μl 1 M $NaHCO_3$, pH 8.6 were added to 400 μl of the solubilized unwashed precipitate and this solution, the solubilized washed precipitate and the supernatant were analyzed for total protein, albumin concentration, and pseudocholinesterase activity in a Hitachi 917 analyzer, Roche, Basel, Switzerland and for vancomycin in an Integra 800 (Fluorescence Polarisation Immuno Assay); electrophoreses were performed in an agarose gel-based Hydrasis LC-Electrophoresis system (Sebia, Fulda, Germany). For control, 1 ml pooled serum was incubated with 1 ml 4.4 mM vancomycin in PBS, and the vancomycin conc. was determined.

Vancomycin dose-dependently increases the turbidity of citrated plasma. The turbidity increases up to about 20fold (FIG. 24a). This precipitation can be reversed by $NaHCO_3$; 30 μl 1 M $NaHCO_3$, pH 8.6, decrease the resulting turbidity to the PBS control value (without vancomycin). Addition of $H_2O$ instead of $NaHCO_3$ does not change the turbidity that had been generated by the vancomycin/plasma reaction (FIG. 24b). The generated turbidity decreases also by addition of arginine, pH 7.5, but not by PBS and only slightly by 20fold concentrated PBS (FIG. 24c). Addition of ≧10 μl 1 M $NaHCO_3$, pH 8.6, to 50 μl plasma and 50 μl PBS results into a pH-value of ≧8.5 (FIG. 24d).

2.11. Electrophoresis of Plasma that had been Incubated with Vancomycin

950 μl P-Pool were incubated with 50 μl 0-200 mM (0-10 mM final conc.) vancomycin for 5 min (RT). Then electrophoreses of the samples and of the solubilized precipitate of 2.10. were performed and the total protein concentrations in the treated samples were determined.

Fibrinogen runs in the β2 fraction of plasma electrophoresis. Increasing the vancomycin concentration in plasma results into a proportional decrease of the β2 fraction (FIG. 25.1-9.).

At 5 mM vancomycin in plasma selectively the β2 peak disappears completely. The total protein concentrations were: 59.0, 59.1, 58.6, 59.1, 58.4, 57.0, 57.8, 56.1, 55.7, 49.4 g/l for 0, 0.29, 0.44, 0.66, 0.99, 1.48, 2.22, 5, 10 mM vancomycin, respectively. The control electrophoresis (0 mM vancomycin) had the following protein peaks: 52.8% albumin, 3.4% α1, 12.0% α2, 10.2% β1, 10.9% β2, and 10.7% γ. The β2 fractions of the vancomycin-treated plasmas were 10.9%, 10.6%, 10.4%, 8.0%, 6.4%, 5.2%, 5.5%, 0%, 0% for 0 mM, 0.29 mM, 0.44 mM, 0.66 mM, 0.99 mM, 1.48 mM, 2.22 mM, 5 mM, 10 mM vancomycin, respectively.

The fibrinogen conc. in the supernatant of 1 part plasma and 1 part 4.4 mM vancomycin in PBS, was 0.32 g/l, i.e. 0.64 g/l fibrinogen remained of initial 4.0 g/l. Thus, 16% of fibrinogen remained in the plasma, whereas 84% of fibrinogen was precipitated by 4.4 mM vancomycin. FIG. 25.10 shows the electrophoresis of the solubilized unwashed supernatant. 77% of the protein is found in the β fraction of the electrophoresis, about 23% is albumin. The total protein conc. was 6.1 g/l, the albumin conc. 0.82 g/l, and the PCHE activity 136 U/l. The P-Pool had an albumin conc. of 27 g/l and a PCHE of 3340 U/l.

After washing the precipitate 3× with aqua dest. >95% of the protein in the precipitate runs in the β fraction of the electrophoresis as one single peak (FIG. 25.11). The protein conc. in this 2 ml-fraction was 7 g/l (=2.8 g/l in 5 ml), albumin was undetectable, PCHE activity was 13 U/l and the vancomycin concentration was 583 mg/l (0.4 mM), i.e. of 2.2 mM vancomycin in the plasma/vancomycin reaction mixture 80 μM attached to 5 μM precipitating fibrinogen (16 vancomycin molecules/fibrinogen molecule). Pooled serum contained after 1+1 incubation with 4.4 mM vancomycin in PBS 2.1 mM vancomycin, the supernatant of pooled plasma contained 0.17 mM vancomycin. The dried precipitate weighed 13±2 mg, i.e. about 2.6 g/l (76%) of the 3.4 g/l precipitated plasma fibrinogen was purified, about 24% of the fibrinogen was lost during the washing process.

2.12. Fbgen Reactivity in Vancomycin-precipitated and Resolubilized Fibrinogen

50 μl P-Pool or 50 μl 300% Fbgen-Pool-Plasma were incubated with 50 μl 4.4 mM vancomycin in PBS for 1 min (RT). Then 20 μl or 40 μl 1 M NaHCO$_3$, pH 8.6 and 200 μl 300 mIU/ml IIa, 400 μg/ml polybrene®, 6% BSA-PBS (FIFTA-reagent) were added and the turbidity increase at 405 nm was determined. Control 1 consisted in addition of the vancomycin after (instead of before) the NaHCO$_3$. Control 2 consisted in replacing the vancomycin of control 1 by PBS. Control 3 consisted in replacing vancomycin and NaHCO$_3$ of control 1 by PBS. A control experiment consisted in incubating 50 μl P-Pool with 0-50 μl 1 M NaHCO$_3$, pH 8.6, 50 μl PBS and 200 μl FIFTA-reagent.

The vancomycin-precipitated and resolubilized fibrinogen regains activity (FIGS. 26*a,b*). It seems to be even more reactive than normal fibrinogen: the half-maximal turbidity increase of vancomycin-reacted fibrinogen is reached after 2 min RT, whereas that of normal fibrinogen needs about 4 min RT. The maximal turbidity increase in control 1 and control 3 is slightly higher. Control 2 shows that the FIFTA at physiologic pH results into nearly twofold higher turbidity increase than at pH 8.6. The NaHCO$_3$-control experiment demonstrates a decrease in maximal turbidity increase by increasing the NaHCO$_3$-buffer amount. Addition of 10-20 μl NaHCO$_3$-buffer seems to result into an acceleration of fibrin generation within the first 5 min RT (FIG. 26*c*).

2.13. Stimulation of t-PA by Vancomycin-precipitated Fibrinogen

Purified System 0-100 μl of the solubilized (in 500 μl 1 M NaHCO$_3$, pH 8.6, +4500 μl PBS, pH 7.4) precipitate of 2.4. and 100-0 μl PBS (volume compensation) were incubated with 50 μl 0.1 mg/ml Glu-plasminogen in PBS, 1% BSA, 50 μl 0.6 M sodium phosphate buffer, pH 7.4, or 50 μl 1 M NaHCO$_3$, pH 8.6, and 50 μl 1000 IU/ml t-PA in PBS, 0.1% Triton X 100® for 30 min (RT). Then 25 μl 2.7 mM Val-Leu-Lys-pNA, 1.7 M KCl were added and the increase in absorbance at 405 nm/h RT recorded, using a microtiterplate reader.

Plasma System

25 μl P-Pool were incubated with 25 μl 0-50 mM vancomycin in PBS and 50 μl 1000 IU/ml t-PA in PBS, 0.1% Triton X 100® and 25 μl 0 mM or 15 mM chloramine-T® for 30 min (RT). Then 25 μl 2.7 mM Val-Leu-Lys-pNA, 1.7 M KCl were added and the resulting plasmin activity was determined by measuring linear absorbance increase/min RT in a microtiterplate reader.

At pH 7.4 the solubilized precipitate dose-dependently stimulates t-PA. 100 μl solubilized precipitate stimulates t-PA about 6fold even in presence of abnormal high ionic strength (>600 mM Na$^+$); at pH 8.6 this stimulation is only 2.5fold (FIG. 27*a*). In the plasma system maximal plasmin activities are measured after incubation of 1 part plasma with 1 part 1.5-5 mM vancomycin in PBS and oxidation of the mixtures with 1 part 15 mM chloramine-T®; t-PA in this assay version is stimulated up to about 20fold (FIG. 27*b*). Without oxidation, the t-PA activity increases 2.5fold after incubation of the sample with 2 mM if the final incubation time is increased to 158 min (RT) and the sample is incubated with 2 mM Vancomycin in PBS (FIG. 27*c*).

2.14. Vancomycin-reactivity with Plasmatic Soluble Fibrin Polymers (SFP) or Serum 1 ml normal plasma pool was supplemented with 50 μl 100 mg/ml purified fibrinogen (Haemocomplettan®), resulting in 260% SFP in the plasma. 50 μl samples of the SFP-supplemented and unsupplemented plasma were analyzed in the FIFTA and the FIATA. Pooled serum was also analyzed in the FIFTA and the FIATA.

Normal plasma supplemented to 260% of norm SFP gives a FIATA-result of 271% of norm and a FIFTA-result of 171% of norm. Pooled patient serum results into 0% FIATA.

2.15. Vancomycin Reactivity with Oxidized Plasma

25 μl P-Pool or P-Pool supplemented with 8.6 mM (3.2 g/l) EDTA were incubated with 25 μl 0-89 mM chloramine-T® in PBS for 60 min at RT. Then the FIATA and the FIFTA were performed. For the FIATA, 25 μl PBS were added and the absorbance at 405 nm was determined (base value). 50 μl 4.4 mM vancomycin in PBS were added and after 1 min (RT) the absorbance at 405 nm was determined again (Table 1). For the FIFTA, 100 μl FIFTA-reagent were added and the turbidity increase at 405 nm was determined. 100% control=P-Pool without oxidant.

Both citrated and EDTA-supplemented citrated plasma react with vancomycin. The reactivity increases by 40% of the citrate control value, if the EDTA-plasmas have previously been oxidized at 10-20 mM chloramine-T® (FIG. 28). In contrast, chloramine-T® inactivates fibrinogen in the FIFTA: 2 mM chloramine-T® inactivates 50% of fibrinogen. This inactivation occurs in both, P-Pool and EDTA supplemented P-Pool. Addition of 8.6 mM EDTA results into about 50% FIFTA decrease, independent of oxidant concentration.

2.16. Vancomycin-reactivity with EDTA-supplemented Plasma

25 μl P-Pool was incubated with 25 μl PBS or with 25 μl 2 mM CT in PBS. After 60 min RT, 25 μl 0-172 mM EDTA in PBS was added. After 5 min RT the FIATA and the FIFTA were performed as indicated in 2.7.

Addition of EDTA at concentrations of 50-100 mM decreases the FIATA result by only 10-20%. In contrast, EDTA at concentrations >5 mmol/l result into a decrease of FIFTA activity of about 50%, in both, 0 mM or 2 mM oxidized samples (FIG. 29).

2.17. Vancomycin-reactivity with Fibrinogen Split Products or BrCN-cleaved Fibrinogen 25 μl P-Pool were incubated with 25 μl 0 mM or 15 mM CT in PBS for 60 min (RT). Then 50 μl 1000 IU/ml t-PA, 0.1% Triton X 100® in PBS were added. After 0-8 h RT 25 μl 4.4 mM vancomycin in PBS were added and the turbidity increase at 405 nm was determined. In addition, 10 mg/ml BrCN-cleaved fibrinogen in 6% BSA-PBS or in pooled serum were assayed in the FIATA.

Addition of t-PA decreases the reactivity of citrated plasma with vancomycin. A 3 h incubation of 25 μl 15 mM CT-oxidized citrated plasma with 50 μl 1000 IU/ml t-PA results into a complete loss of vancomycin reactivity, a 50% loss of reactivity occurs within about 1 h, whereas in unoxidized plasma 6 h are needed for a 50% loss of vancomycin reactivity; this is due to the absence of functional α2-antiplasmin in 15 mM CT-oxidized plasma (FIG. 30). BrCN-cleaved fibrinogen does not react in the FIATA.

FIGURES

FIGS. 1a-d: Optimization of thrombin concentration

50 µl P-Pool (FIG. 1a) or P-Pool diluted 1:2 with 6% BSA-PBS (FIG. 1b) were incubated with 100 µl 0-1519 mIU/ml bovine thrombin for 0-15 min (RT) and the turbidity increase (ΔA) at 405 nm was determined; thrombin concentrations in the thrombin-reagent: 0 mIU/ml (O), 26 mIU/ml (■), 39 mIU/ml (–), 59 mIU/ml (X), 89 mIU/ml (*), 133 mIU/ml ( ), 200 mIU/ml (+), 300 mIU/ml (●), 450 mIU/ml (◇), 675 mIU/ml (♦), 1013 mIU/ml (Δ), 1519 mIU/ml (▲). ΔA-ratios diluted P-Pool/P-Pool (FIG. 1c). Incubation times (RT) for P-Pool: 2.5 min (♦), 5 min (●), 10 min (▲), 15 min (■); incubation times (RT) for 1:2 diluted P-Pool: 2.5 min (◇), 5 min (O), 10 min (Δ), 15 min ( ) (FIG. 1d).

FIGS. 2a-d: Optimization of polybrene® (PB) concentration

P-Pool supplemented with 0-35 IU/ml heparin was analyzed in the FIFTA. The FIFTA-reagent contained 200 mIU/ml thrombin, 6% BSA-PBS and 0 µg/ml polybrene® (PB; FIG. 2a), 50 µg/ml PB (FIG. 2b), 100 µg/ml PB (FIG. 2c), 200 µg/ml PB (FIG. 2d); heparin concentrations in the sample: 0 IU/ml (♦), 0.14 IU/ml (■), 0.27 IU/ml (▲), 0.55 IU/ml (X), 1.09 IU/ml (*), 2.19 IU/ml (●), 4.38 IU/ml (+), 8.75 IU/ml (Δ), 17.5 IU/ml (O), 35 IU/ml ( ).

FIGS. 2e-g: Optimization of polybrene® concentration

P-Pool supplemented with 0-100 IU/ml heparin was analyzed in the FIFTA. The FIFTA-reagent contained 200 mIU/ml thrombin, 6% BSA-PBS and 400 µg/ml PB (FIG. 2e), 800 µg/ml PB (FIG. 2f), 1600 µg/ml PB (FIG. 2g); heparin concentrations in the sample: 0 IU/ml (♦), 11 IU/ml (■), 13 IU/ml (▲), 17 IU/ml (X), 21 IU/ml (*), 26 IU/ml (●), 33 IU/ml (+), 41 IU/ml (Δ), 51 IU/ml (◇), 64 IU/ml (O), 80 IU/ml ( ), 100 IU/ml (–).

FIG. 3: Neutralization of 100 IU/ml heparin in plasma by polybrene®

25 µl 0-75 mg/ml polybrene® in aqua dest. were added to 50 µl P-Pool (●) or to 50 µl P-Pool supplemented with 100 IU/ml heparin (■). Then 100 µl 200 mIU/ml thrombin in 6% BSA-PBS, 400 µg/ml PB were added and ΔA at 405 nm was determined.

FIG. 4: FIFTA for polybrene®-neutralized heparinized plasma

25 µl 0-75 mg/ml polybrene® in aqua dest. were added to 50 µl P-Pool (●) or to 50 µl P-Pool supplemented with 100 IU/ml heparin (■). Then 100 µl 200 mIU/ml thrombin, 400 µg/ml PB, 6% BSA-PBS were added and ΔA at 405 nm was followed.

FIG. 5: Turbidity increase by heparin/polybrene® complexes

50 µl plasma with 0-80 IU/ml heparin were incubated with 100 µl FIFTA-reagent without thrombin, containing 0 µg/ml (O), 400 µg/ml (■), 800 µg/ml (▲), or 1600 µg/ml (●) PB. ΔA at 405 nm was determined.

FIGS. 6a,b: Albumin-dependence of turbidity increase

P-Pool (●), P-Pool diluted 1:2 with PBS (■) or with 6% BSA-PBS (O) and analyzed in the FIFTA, using the 200 mIU/ml thrombin reagent without albumin (FIG. 6a). The ΔA ratios diluted/undiluted were calculated (FIG. 6b).

FIGS. 7a,b: Reaction kinetic of FIFTA

The FIFTA was performed with P-Pool and with 6% albumin-PBS dilutions of P-Pool. ΔA was determined after 0-15 min and after 25 min, 75 min, 17 h (RT); fibrinogen activity [% of norm] in sample: 0% (O), 2.5% ( ), 3.9% (–), 5.7% (◇), 8.6 % (●), 19% (+), 29% (Δ), 43% (*), 65% (♦), 98% (■), 146% (▲) (FIG. 7a). ΔA after 2 min (♦), 5 min (■), 10 min (▲), 15 min ( ), 25 min (*), 75 min (●), 17 h (O) (FIG. 7b).

FIGS. 7c-e: Reaction kinetic of FIFTA

The FIFTA was performed with 100% Normal-Pool (●), 200% Pool-Plasma (■) (FIG. 7c), 256% Plasma-Pool (■), 120% Plasma-Pool (●), and 63% Plasma-Pool (▲) (FIG. 7d); ΔA-ratios 120%/256% (●) und 63%/256% (▲) (FIG. 7e).

FIGS. 7f,g: Reaction kinetic of FIFTA

The FIFTA was performed with 300% Fbgen-Pool (●), 1:2 with 6% BSA-PBS diluted 300% Fbgen Pool (●), and 120% Standard-Pool-Plasma (Δ) (FIG. 7f); ΔA-ratios 150%/300% (FIG. 7g).

FIGS. 8a,b: Reaction kinetic at 37° C.

The FIFTA was performed with 256% Fbgen-Pool (●) and with 256% Fbgen-Pool that had been diluted 1:2 with 6% BSA-PBS (●). After reaction times of 30-370 seconds in 10 seconds intervals and after 20 and 60 min in a 37° C. water bath the turbidity increase at 405 nm was determined (FIG. 8a). The 125%/250% ΔA-ratios were calculated (FIG. 8b).

FIG. 9a: Assay Linearity

The FIFTA was performed with 300% Fbgen-Pool and dilutions thereof (with 6% BSA-PBS); 50 µl+100 µl assay version (●), 25 µl +50 µl assay version (O).

FIGS. 9b,c: Assay Linearity

The FIFTA was performed with 300% Fbgen-Pool and dilutions (physiol. NaCl) thereof; fibrinogen activity in samples: 0% (–), 17% ( ), 23% (Δ), 30% (◇), 40% (*), 53% (●), 71% (+), 95% (X), 127% (O), 169% (●), 225% (▲), 300% (♦) turbidity increase in dependence of reaction time (FIG. 9b); ΔA in dependence of fibrinogen activity (FIG. 9c): incubation times at RT: 2.5 min (O), 5 min (●), 10 min (■), 15 min (▲).

FIGS. 10a,b: Variation of assay volumina

250% Fbgen-Pool (●) and a 250% Fbgen-Pool that had been diluted 1:2 with 6% BSA-PBS (O) was assayed in the FIATA (50 µl sample+100 µl thrombin reagent). 67 µl 250% Fbgen-Pool (■) or 1:2 diluted Fbgen-Pool ( ) were incubated with 83 µl thrombin reagent. 100 µl 250% Fbgen-Pool (▲) or 1:2 diluted Fbgen-Pool (Δ) was incubated with 50 µl thrombin reagent, containing 600 mIU/ml thrombin (FIG. 10a); ΔA-ratios 125%/250% (FIG. 10b).

FIG. 11: Absorbance wavelength for turbidity

The FIFTA was performed for P-Pool and for 256% Fbgen-Pool. Reaction time=30 min RT. The final absorbance was determined at 405 nm, 450 nm, 595 nm, and 650 nm by a microtiter plate reader.

FIG. 12a-e: FIFTA addition-calibration with purified fibrinogen

6% BSA-PBS (FIG. 12a,b) or P-Pool (containing 144% of norm fibrinogen activity) (FIG. 12c) was supplemented with purified fibrinogen by 20 g/l (Δ), 10 g/l ( ), 5 g/l (◇), 2.5 g/l (*), 1.25 g/l (X), 0.63 g/l (▲), 0.31 g/l (■), 0 g/l (♦). The FIFTA was performed; turbidity increase after incubations (RT) of 2.5 min (Δ), 5 min ( ), 10 min (*), 15 min (O), 48 min (▲), 158 min (■), 18 h (●) (FIGS. 12b,d). From FIG. 12c it resulted that 46% of the purified fibrinogen was clottable; 6% BSA-PBS (●) or P-Pool (■) (FIG. 12e).

FIG. 13a,b: Correlation with Clauss-method

In n=334 unselected patient plasmas (≦6 h old; at the time point of the usual discarding the samples) the FIFTA (0=132%, SD=41%) was performed and compared to the modified Clauss-method (0=4.18 g/l, SD=1.65 g/l) (FIG. 13a). The FIFTA results of the patients distribute with a normal Gaussian distribution (FIG. 13b).

FIG. 14a,b: IC50 of heparin in the FIFTA

50 µl P-Pool were added to 10 µl 0-160 IU/ml heparin. 100 µl 200 mIU/ml thrombin in 6% BSA-PBS (without polybrene®) were added and ΔA at 405 nm was followed; heparin concentrations: 0 IU/ml (●), 0.04 IU/ml (■), 0.08 IU/ml (▲), 0.16 IU/ml (Δ), 0.31 IU/ml ( ), 0.63 IU/ml (O) (FIG. 14a). ΔA after incubations of 5 min (●), 10 min (■), 15 min (▲), 20 min (Δ) (RT) (FIG. 14b).

FIG. 15a: Inhibitory time point 50% of 10 IU/ml heparin in the FIFTA

50 μl P-Pool were incubated with 100 μl 200 mIU/ml thrombin in 6% BSA-PBS (without polybrene®). At the incubation time points of 0 min (prior to thrombin addition) (O), 0.5 min (■), 1 min (▲), 1.5 min (♦), 2 min (*), 2.5 min (●), 3 min (+), 3.5 min (Δ), 4 min (X), 5 min (-Δ-), 6 min (-■-), 7 min (–), 8 min (-*-), 9 min (-X-), 10 min (◇), 11 min (- -) 10 μl 160 IU/ml heparin in 6% BSA-PBS were added (final heparin conc. in plasma +thrombin reagent =10 IU/ml) and ΔA at 405 nm was determined.

FIG. 15b,c: Inhibitory time point 50% of 10 IU/ml heparin in the FIFTA

50 μl P-Pool were incubated with 100 μl 200 mIU/ml thrombin in 6% BSA-PBS (without polybrene®). After incubation times of 10 s (♦), 20 s (■), 30 s (▲), 40 s (X), 50 s (*), 60 s (●), 70 s (+), 80 s (◇), 90 s (–), 100 s (-♦-), 110s ( ), 120 s (-▲-), 130 s (-x-), 140 s (-*-) at RT 10 μl 160 IU/ml heparin in 6% BSA-PBS were added; control: addition of 10 μl 0 IU/ml heparin (Δ). ΔA at 405 nm was determined. The turbidity increase at 405 nm was determined (FIG. 15b). ΔA after incubations of 5 min (●), 10 min (■), 15 min (▲), 20 min (Δ) (RT) (FIG. 15c).

FIG. 16a,b: Inhibition of fibrin generation by arginine 10 ml FIFTA-reagent were added to 5 ml P-Pool, and 100 μl of this mixture were immediately pipetted into a microtiterplate, which had been prefilled with 200 μl 0-1500 mM arginine, pH 8.7, per well, resulting in final arginine conc. of 0 mM (●), 16 mM (■), 31 mM (▲), 62.5 mM (O), 125 mM (*), 250 mM (◇), 500 mM (+), 1000 mM ( ). ΔA during the first 9 min (RT) (FIG. 16a) or 75 min (RT) (FIG. 16b) was monitored.

FIG. 16c: Inhibition of fibrin generation by arginine 10 ml FIFTA-reagent were added to 5 ml P-Pool, and after 0-4 min (RT) 100 μl of this mixture were pipetted into a microtiterplate, which had been prefilled with 200 μl 0-1500 mM arginine, pH 8.7, per well. ΔA at 405 nm was determined; the final arginine conc. were: 0 mM (●), 16 mM (■), 31 mM (▲), 62.5 mM (O), 125 mM (*), 250 mM (◇), 500 mM (+), 1000 mM ( ).

FIG. 16d: Inhibition of fibrin generation by arginine

50 μl P-Pool were incubated with 100 μl FIFTA-reagent. After 0-30 min (RT) 0-70 μl 1.5 M arginine, pH 8.7, were added and after the last time point (30 min) the final ΔA was determined at 405 nm; the final arginine conc. were: 0 mM (●), 94 mM (■), 176 mM (▲), 250 mM (O), 316 mM (*), 375 mM (◇), 429 mM (+), 477 mM ( ).

FIG. 17: Fibrin dissolution by arginine

50 μl P-pool were incubated with 100 μl FIFTA-reagent. After 30 min (RT) 10 μl or 70 μl 1.5 M arginine, pH 8.7 (final arginine conc. 94 mM (■) or 477 mM (●)) were added and the final ΔA was determined at 405 nm after 0-132 min (RT).

FIG. 18: Inactivation of fibrinogen by vancomycin

200 μl of 300% (8.4 g/l) Fbgen-Pool were incubated with 25 μl 0-100 mM vancomycin (■) or 0-100 mM chloramine-T® (●) for 15 min (37° C.). 50 μl samples of these reaction mixtures were withdrawn and incubated with 100 μl 200 mIU/ml thrombin, 400 μg/ml polybrene®, 6% BSA-PBS. ΔA at 405 nm was determined.

FIG. 19a,b: Is the reaction between vancomycin and plasmatic fibrinogen quenchable by antioxidants?

750 μl 300% (8.4 g/l) Fbgen-Plasma-Pool were supplemented with 250 μl 200 mM of a) the $^1O_2$ quenchers methionine (▲) or sodium ascorbate (■), b) the —OH radical quencher mannitol (●), or c) $H_2O$ (O). 25 μl samples thereof were incubated with 25 μl 0-2.5 mM vancomycin (FIG. 7a) or 0-5 mM chloramine-T® (FIG. 7b) in PBS for 15 min at 37° C. Then 100 μl 200 mIU/ml thrombin, 400 μg/ml polybrene® in 6% BSA-PBS were added and ΔA/5 min (RT) were compared against that of the 100% control (0 mM vancomycin or chloramine-T®).

FIG. 20a: ΔA in dependence of vancomycin-concentration

50 μl Patient-Pool (●) or 1:2 (▲) or 1:4 (■) diluted Patient-Pool, or 6% BSA-PBS (O) were incubated with 50 μl 0-6.8 mM vancomycin in PBS. ΔA at 405 nm was determined after 1 min (RT).

FIG. 20b: ΔA in dependence of fibrinogen-concentration

25 μl 300% Fbgen-Pool were incubated with 125 μl 0.55 mM (▲), 1.1 mM (■), or 2.2 mM (●) vancomycin in PBS for 1 min (RT). Then ΔA at 405 nm was determined.

FIG. 21: FIATA calibration with purified fibrinogen 250 mg lyophilized purified fibrinogen were reconstituted with 12.5 ml of either 6% BSA-PBS (●) or P-Pool (■). The obtained supplemented fibrinogen samples were 1:2, 1:4, 1:8, 1:16, 1:32, 1:64, 1:128 diluted with either BSA-PBS or P-Pool, resulting into samples containing either 0-20 g/l fibrinogen in BSA-PBS or samples containing 4-24 g/l fibrinogen in P-Pool. The FIATA was performed.

FIG. 22a-e: FIATA Linearity

250% Fbgen-Pool was diluted with 6% BSA-PBS and assayed in the FIATA (FIG. 22a). 300% Fbgen-Pool was diluted with normal serum and assayed in the FIATA (FIG. 22b). The assay volumina of FIG. 10b were doubled and the FIATA was performed (FIG. 22c). 0-55 μl 250% Fbgen-Pool were incubated with a) 50 μl PBS and 50 μl 4.4 mM vancomycin in PBS. ΔA at 405 nm was determined (FIG. 22d). The FIATA was performed with 50 μl sample (0-300% of norm) and 50 μl 4.4 mM vancomycin in PBS (FIG. 22e).

FIG. 23a-c: FIATA correlation with functional fibrinogen determinations

In n=321 unselected patient plasmas the FIATA was performed and compared to the modified Clauss-Method (Multifibren U®; Behring Coagulation Timer), r=0.755; y=19.521x+49.165 (FIG. 23a). In n=344 unselected patient plasmas the FIATA was performed and compared to the functional fibrinogen determination in the FIFTA, r=0.813; y=0.861x+22.993 (FIG. 23b), the FIATA results distribute with a normal Gauss-distribution (FIG. 23c).

FIG. 24a: Precipitation of plasmatic fibrinogen by vancomycin

25 μl of 143% (4.0 g/l) P-Pool were incubated with 25 μl 0-50 mM vancomycin in PBS, 50 μl PBS, 0.1% Triton X 100® and 50 μl 850 mM KCl in $H_2O$ for 1 min (RT). ΔA at 405 nm was determined.

FIG. 24b: Reversal of vancomycin induced fibrinogen precipitation by $NaHCO_3$

50 μl P-Pool reacted with 50 μl 4.4 mM vancomycin in PBS for 1 min (RT). To reverse vancomycin induced fibrinogen precipitation 0-55 μl 1 M $NaHCO_3$, pH 8.6 (■), or $H_2O$ (●) were added. The absorbance at 405 nm was determined after 1 min (RT). Absorbance control (O) without vancomycin, with $NaHCO_3$.

FIG. 24c: Determination of assay pH of FIG. 12b 5 ml P-Plasma were mixed with 5 ml PBS and 0-1750 μl 1 M $NaHCO_3$, pH 8.6 and the pH was determined.

FIG. 24d: Reversal of vancomycin induced fibrinogen precipitation by arginine

50 μl P-Pool reacted with 50 μl 4.4 mM vancomycin in PBS for 1 min (RT). To reverse vancomycin induced fibrinogen precipitation 0-55 μl PBS (▲), 20fold concentrated PBS (♦), or 1 M arginine, pH 7.5 (●) were added. The absorbance at 405 nm was determined after 1 min (RT).

FIG. 25: Electrophoresis of plasma that had been incubated with vancomycin

Patient-Pool plasma was incubated with 0-10 mM (final conc.) vancomycin for 5 min (RT). Then electrophoreses system (⊕=anode to the left of the figure) of the samples were performed Lane 1: 0 mM vancomycin in 143% of norm of antigenic fibrinogen in P-Pool (FIG. 25a)
Lane 2: 0.29 mM vanco in P-Pool (FIG. 25b)
Lane 3: 0.44 mM vanco in P-Pool (FIG. 25c)
Lane 4: 0.66 mM vanco in P-Pool (FIG. 25d)
Lane 5: 0.99 mM vanco in P-Pool (FIG. 25e)
Lane 6: 1.48 mM vanco in P-Pool (FIG. 25f)
Lane 7: 2.22 mM vanco in P-Pool (FIG. 25g)
Lane 8: 5 mM vanco in P-Pool (FIG. 25h)
Lane 9: 10 mM vanco in P-Pool (FIG. 25i)
Lane 10: Resolubilized unwashed precipitate between 5 ml plasma and 5 ml 4.4 mM vancomycin in PBS (FIG. 25j)
Lane 11: 3× washed precipitate of FIG. 25j(FIG. 25k)

FIG. 26a-c: Fibrinogen reactivity in vancomycin-precipitated plasma

50 µl Patient-Pool or 300% Fbgen-Pool were incubated with 50 µl 4.4 mM vancomycin in PBS for 1 min (RT). Then 20 µl 1 M $NaHCO_3$, pH 8.6, and 200 µl 300 mIU/ml Thrombin, 400 µg/ml polybrene®, 6% BSA-PBS (FIFTA-reagent) were added and ΔA at 405 nm was determined (Plasma/Vanco/$NaHCO_3$=▲). Control 1 consisted in addition of the vancomycin after the $NaHCO_3$ (Plasma/$NaHCO_3$Vanco=Δ). Control 2 consisted in replacing the vancomycin of control 1 by PBS (Plasma/PBS/$NaHCO_3$=●). Control 3 consisted in replacing vancomycin and $NaHCO_3$ of control 1 by PBS (Plasma/PBS/PBS=O) (FIG. 26a); instead of 20 µl $NaHCO_3$ 40 µl $NaHCO_3$ were used (FIG. 26b). 50 µl P-Pool were incubated with 0-50 µl 1 M $NaHCO_3$, pH 8.6, 50 µl PBS and 200 µl FIFTA-reagent, ΔA at 405 nm was determined: 0 µl (O), 10 µl (■), 20 µl (▲), 30 µl (♦), 40 µl (*), 50 µl (●) (FIG. 26c).

FIG. 27a: Stimulation of t-PA by vancomycin-precipitated fibrinogen 0-100 µl of the solubilized precipitate of FIG. 13 and 100-0 µl PBS (for volume compensation) were incubated with 50 µl 0.1 mg/ml Glu-plasminogen in PBS, 1% BSA, 50 µl 0.6 M $PO_4^{3-}$ buffer, pH 7.4 (●), or 50 µl 1 M $NaHCO_3$, pH 8.6 (■), and 50 µl 1000 IU/ml t-PA in PBS, 0.1% Triton X 100® for 30 min (RT). Then 25 µl 2.7 mM Val-Leu-Lys-pNA, 1.7 M KCl were added and ΔA at 405 nm/h RT was recorded.

FIG. 27b,c: Stimulation of t-PA by vancomycin-precipitated plasma

25 µl P-Pool were incubated with 25 µl 0-22 mM vancomycin in PBS and 50 µl 1000 IU/ml t-PA in PBS, 0.1% Triton X 100® and 25 µl 0 mM (O) or 15 mM chloramine-T® (●) for 30 min at RT. Then 25 µl 2.7 mM Val-Leu-Lys-pNA, 1.7 M KCl were added and the resulting plasmin activity was determined by measuring ΔA/min RT (FIG. 27b). Prolongation of the final incubation time to 158 min (RT) for unoxidized sample (FIG. 27c).

FIG. 28: Vancomycin reactivity with oxidized plasma

25 µl P-Pool, unsupplemented (●) or supplemented with 8.6 mM (3.2 g/l) EDTA (O), were incubated with 25 µl 0-89 mM chloramine-T® in PBS for 60 min at RT. Then the FIATA (—) or the FIFTA (- - -) were performed.

FIG. 29: Vancomycin-reactivity with EDTA-supplemented plasma

25 µl P-Pool were incubated with 25 µl PBS (O) or with 25 µl 2 mM chloramine-T® in PBS (●). After 60 min (RT) 25 µl 0-172 mM EDTA in PBS were added. After 5 min (RT) the FIATA (—) and the FIFTA (- - -) were performed.

FIG. 30: Vancomycin-reactivity with t-PA incubated plasma

25 µl 300% Fbgen-Pool were incubated with 25 µl PBS (O) or 15 mM chloramine-T®, PBS (●) for 60 min (RT). Then 50 µl 1000 IU/ml t-PA, 0.1% Triton X 100®, PBS were added. After 0-8 h (RT) 25 µl 4.4 mM vancomycin, PBS were added and ΔA at 405 nm was determined.

The invention claimed is:

1. A method to determine fibrinogen and/or derivatives of fibrinogen in a solution to be analyzed, comprising (a) adding thrombin in dissolved form to the solution such that the final concentration of thrombin in the solution is less than 2 IU/ml and adding albumin in dissolved form to the solution such that the final concentration of albumin in the solution is more than 1.7% (w/v), thereby preparing a mixture and (b) measuring the increase in turbidity of the mixture, wherein the method is independent of matrix and/or independent of time of coagulation.

2. A method according to claim 1, wherein the final concentration of albumin in the solution is 1.7-10% (w/v) and the increase in turbidity is measured by measuring the increase in absorbance of the mixture.

3. A method according to claim 2, whereby a comparison-determination with a known standard, containing fibrinogen and/or fibrinogen-derivatives is performed.

4. A method according to claim 2, whereby the solution to be analyzed is blood or plasma of blood.

5. A method according to claim 4, whereby the plasma of blood is selected from the group consisting of citrate-plasma, EDTA-plasma, heparin-plasma and guanidine compound-plasma.

6. A method according to claim 2, whereby the thrombin concentration in the thrombin- and albumin containing solution is 50-1000 mIU/ml, and/or the thrombin amount to be added is 5-100 mIU per 50 µl plasma.

7. A method according to claim 2, whereby thrombin and/or albumin are/is dissolved in a buffered solution.

8. A method according to claim 7, whereby the buffer is phosphate-buffered sodium chloride (PBS).

9. A method according to claim 2, whereby the thrombin and albumin-containing solution additionally contains polybrene.

10. A method according to claim 9, whereby the polybrene-concentration is up to 1000 µg/ml and/or the polybrene amount to be added is up to 100 µg per 50 µl plasma.

11. A method according to claim 9, whereby for the analysis of heparin-plasmas the polybrene-concentration is 1000-30000 µg/ml and/or the polybrene amount to be added is 100-3000 µg per 50 µl plasma.

12. A method according to claim 2, whereby the method is performed at a temperature of 0-42° C.

13. A method according to claim 2, whereby the time between the addition of thrombin and albumin to the solution to form the mixture and the measurement of the increase of turbidity is between 20 seconds and 60 minutes.

14. A method according to claim 1, whereby the albumin-concentration in the thrombin- and albumin-containing solution is 2-20% (w/v).

15. A method to diagnose pathologic disseminated intravascular coagulation and/or to assess patient risk for athero-thrombotic disease comprising obtaining a blood or plasma sample from a patient and determining the content of fibrinogen and/or fibrinogen derivatives in the sample according to the method of claim 1.

16. The method of claim 15, wherein the final concentration of thrombin in solution is up to 200 mIU thrombin per 50 µl plasma, and/or the final concentration of albumin in solution is 2-20% (w/v) albumin.

* * * * *